(12) United States Patent
Arslan et al.

(10) Patent No.: US 12,313,627 B2
(45) Date of Patent: May 27, 2025

(54) MULTIVALENT BINDING COMPOSITION FOR NUCLEIC ACID ANALYSIS

(71) Applicant: Element Biosciences, Inc., San Diego, CA (US)

(72) Inventors: Sinan Arslan, San Diego, CA (US); Molly He, San Dieg, CA (US); Michael Previte, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 18/431,748

(22) Filed: Feb. 2, 2024

(65) Prior Publication Data

US 2024/0230631 A1    Jul. 11, 2024

Related U.S. Application Data

(63) Continuation-in-part of application No. 16/936,121, filed on Jul. 22, 2020, now Pat. No. 12,117,438, which is a continuation of application No. 16/579,794, filed on Sep. 23, 2019, now Pat. No. 10,768,173, application No. 18/431,748, filed on Feb. 2, 2024 is a continuation-in-part of application No. 18/415,517, filed on Jan. 17, 2024, which is a continuation of application No. 17/373,655, filed on Jul. 12, 2021, now abandoned, which is a continuation-in-part of application No. PCT/US2020/031161, filed on May 1, 2020, which is a continuation-in-part of application No. 16/543,351, filed on Aug. 16, 2019, now abandoned.

(60) Provisional application No. 62/897,172, filed on Sep. 6, 2019, provisional application No. 62/841,541, filed on May 1, 2019.

(51) Int. Cl.
*G01N 33/53* (2006.01)
*C12Q 1/6874* (2018.01)
*G01N 33/58* (2006.01)

(52) U.S. Cl.
CPC ....... *G01N 33/5308* (2013.01); *C12Q 1/6874* (2013.01); *G01N 33/582* (2013.01)

(58) Field of Classification Search
CPC ............. G01N 33/5308; G01N 33/582; C12Q 1/6874; C12Q 1/6869; C12Q 2521/101; C12Q 2525/186; C12Q 2537/143; C12Q 2563/107
See application file for complete search history.

(56) References Cited

U.S. PATENT DOCUMENTS

| | | |
|---|---|---|
| 4,083,057 A | 4/1978 | Quinn |
| 5,512,436 A | 4/1996 | Stone |
| 5,547,839 A | 8/1996 | Dower et al. |
| 5,578,832 A | 11/1996 | Trulson et al. |
| 5,622,872 A | 4/1997 | Ribi |
| 5,624,711 A | 4/1997 | Sundberg et al. |
| 5,834,758 A | 11/1998 | Trulson et al. |
| 5,859,336 A | 1/1999 | Koziel et al. |
| 6,115,192 A | 9/2000 | McDonald |
| 6,558,928 B1 | 5/2003 | Landegren |
| 6,720,143 B2 | 4/2004 | Juncosa et al. |
| 6,829,051 B2 | 12/2004 | Abe et al. |
| 7,101,668 B2 | 9/2006 | Ng |
| 8,039,817 B2 | 10/2011 | Feng et al. |
| 8,071,962 B1 | 12/2011 | Feng et al. |
| 8,143,599 B2 | 3/2012 | Feng et al. |
| 8,242,463 B2 | 8/2012 | Feng et al. |
| 8,278,630 B1 | 10/2012 | Feng et al. |
| 8,399,196 B2 | 3/2013 | Hoser |
| 8,546,772 B2 | 10/2013 | Feng et al. |
| 8,586,947 B1 | 11/2013 | Feng et al. |
| 8,698,102 B2 | 4/2014 | Feng et al. |
| 9,068,220 B2 | 6/2015 | Feng et al. |
| 9,193,998 B2 | 11/2015 | Khurana et al. |
| 9,217,178 B2 | 12/2015 | Fedurco et al. |
| 9,222,132 B2 | 12/2015 | Drmanac |
| 9,303,287 B2 | 4/2016 | Matthiesen |
| 9,303,290 B2 | 4/2016 | Fedurco et al. |
| 9,365,898 B2 | 6/2016 | Feng et al. |
| 9,587,268 B2 | 3/2017 | Borns |
| 9,944,924 B2 | 4/2018 | Rigatti et al. |

(Continued)

FOREIGN PATENT DOCUMENTS

DE    10014204 A1    10/2001
WO    WO-9508000 A2    3/1995

(Continued)

OTHER PUBLICATIONS

Co-pending U.S. Appl. No. 18/424,394, inventors Chen; Steve Xiangling et al., filed Jan. 26, 2024.

(Continued)

*Primary Examiner* — Narayan K Bhat
(74) *Attorney, Agent, or Firm* — WILSON SONSINI GOODRICH & ROSATI

(57) ABSTRACT

Multivalent binding compositions including a particle-nucleotide conjugate having a plurality of copies of a nucleotide attached to the particle are described. The multivalent binding compositions allow one to localize detectable signals to active regions of biochemical interaction, e.g., sites of protein-protein interaction, protein-nucleic acid interaction, nucleic acid hybridization, or enzymatic reaction, and can be used to identify sites of base incorporation in elongating nucleic acid chains during polymerase reactions and to provide improved base discrimination for sequencing and array based applications.

21 Claims, 14 Drawing Sheets

Specification includes a Sequence Listing.

(56) References Cited

U.S. PATENT DOCUMENTS

| | | |
|---|---|---|
| 9,944,975 B2 | 4/2018 | Wilber-Mader |
| 9,970,055 B2 | 5/2018 | Fedurco et al. |
| 10,093,962 B2 | 10/2018 | Borns |
| 10,202,638 B2 | 2/2019 | Matthiesen |
| 10,233,490 B2 | 3/2019 | Stapleton et al. |
| 10,656,368 B1 | 5/2020 | Rosenberry et al. |
| 10,662,473 B2 | 5/2020 | Drmanac |
| 10,704,094 B1 | 7/2020 | Arslan et al. |
| 10,876,148 B2 | 12/2020 | Zhou et al. |
| 10,919,033 B2 | 2/2021 | Ren et al. |
| 10,982,280 B2 | 4/2021 | Arslan et al. |
| 11,053,540 B1 | 7/2021 | Chen et al. |
| 11,060,138 B1 | 7/2021 | Chen et al. |
| 11,118,214 B2 | 9/2021 | Matthiesen et al. |
| 11,198,121 B1 | 12/2021 | Guo et al. |
| 11,200,446 B1 | 12/2021 | Zhou et al. |
| 11,220,707 B1 | 1/2022 | Arslan et al. |
| 11,236,388 B1 | 2/2022 | Arslan et al. |
| 11,261,489 B2 | 3/2022 | Chen et al. |
| 11,287,422 B2 | 3/2022 | Previte et al. |
| 11,339,433 B2 | 5/2022 | Chen et al. |
| 11,365,444 B2 | 6/2022 | Chen et al. |
| 11,408,032 B2 | 8/2022 | Chen et al. |
| 11,426,732 B2 | 8/2022 | Guo et al. |
| 11,427,855 B1 | 8/2022 | Arslan et al. |
| 11,447,582 B2 | 9/2022 | Brown et al. |
| 11,459,608 B2 | 10/2022 | Chen et al. |
| 11,535,892 B1 | 12/2022 | Arslan et al. |
| 11,781,185 B2 | 10/2023 | Arslan et al. |
| 11,795,504 B2 | 10/2023 | Chen et al. |
| 12,134,766 B2 | 11/2024 | Kellinger et al. |
| 12,146,190 B2 | 11/2024 | Ghorbani et al. |
| 2002/0106789 A1 | 8/2002 | Antoniou et al. |
| 2003/0017461 A1 | 1/2003 | Singh et al. |
| 2003/0061628 A1 | 3/2003 | Antoniou et al. |
| 2003/0181383 A1 | 9/2003 | Podolsky |
| 2004/0054160 A1 | 3/2004 | Pal |
| 2004/0241742 A1 | 12/2004 | Peck et al. |
| 2004/0248287 A1 | 12/2004 | Hu et al. |
| 2005/0100951 A1 | 5/2005 | Pircher |
| 2005/0287560 A1 | 12/2005 | Garimella et al. |
| 2007/0298006 A1 | 12/2007 | Tomalia et al. |
| 2008/0030721 A1 | 2/2008 | Kepler et al. |
| 2008/0242560 A1 | 10/2008 | Gunderson et al. |
| 2008/0274905 A1 | 11/2008 | Greene |
| 2009/0103792 A1 | 4/2009 | Rahn et al. |
| 2009/0186775 A1 | 7/2009 | Nowak et al. |
| 2010/0075332 A1 | 3/2010 | Patel et al. |
| 2010/0282617 A1 | 11/2010 | Rothberg et al. |
| 2010/0298171 A1 | 11/2010 | Shirazi et al. |
| 2010/0321786 A1 | 12/2010 | Rahn et al. |
| 2011/0220775 A1 | 9/2011 | Triener et al. |
| 2012/0046176 A1 | 2/2012 | Su et al. |
| 2012/0105858 A1 | 5/2012 | Popescu et al. |
| 2013/0004949 A1 | 1/2013 | Rearick |
| 2013/0165350 A1 | 6/2013 | Kuimelis et al. |
| 2013/0338044 A1 | 12/2013 | Liao et al. |
| 2014/0011703 A1 | 1/2014 | Ye et al. |
| 2014/0287945 A1 | 9/2014 | Lau et al. |
| 2015/0023840 A1 | 1/2015 | Kinz-Thompson et al. |
| 2016/0041095 A1 | 2/2016 | Rothberg et al. |
| 2016/0076023 A1 | 3/2016 | Quake et al. |
| 2016/0287152 A1 | 10/2016 | Schwartz et al. |
| 2016/0304945 A1 | 10/2016 | Matthiesen |
| 2016/0357173 A1 | 12/2016 | Foschini et al. |
| 2017/0128380 A1 | 5/2017 | Wang |
| 2017/0136433 A1 | 5/2017 | Sun et al. |
| 2017/0198341 A1 | 7/2017 | Abravaya et al. |
| 2019/0219835 A1 | 7/2019 | Skinner et al. |
| 2019/0276884 A1 | 9/2019 | Stapleton et al. |
| 2019/0276886 A1 | 9/2019 | Skinner et al. |
| 2020/0129974 A1 | 4/2020 | Ren et al. |
| 2020/0149095 A1* | 5/2020 | Arslan ............... C12Q 1/6844 |
| 2020/0179921 A1 | 6/2020 | Arslan et al. |
| 2020/0182866 A1 | 6/2020 | Arslan et al. |
| 2020/0347443 A1 | 11/2020 | Arslan et al. |
| 2020/0370113 A1 | 11/2020 | Kellinger et al. |
| 2021/0040534 A1 | 2/2021 | Zhou et al. |
| 2021/0072234 A1 | 3/2021 | Arslan et al. |
| 2021/0123098 A1 | 4/2021 | Previte et al. |
| 2021/0123911 A1 | 4/2021 | Arslan et al. |
| 2021/0139884 A1 | 5/2021 | Kellinger et al. |
| 2021/0139981 A1 | 5/2021 | Arslan et al. |
| 2021/0247389 A1 | 8/2021 | Arslan et al. |
| 2021/0269793 A1 | 9/2021 | Kellinger et al. |
| 2021/0318295 A1 | 10/2021 | Arslan et al. |
| 2021/0332430 A1 | 10/2021 | Arslan et al. |
| 2021/0373000 A1 | 12/2021 | Arslan et al. |
| 2021/0387184 A1 | 12/2021 | Guo et al. |
| 2022/0136047 A1 | 5/2022 | Chen et al. |
| 2022/0170919 A1 | 6/2022 | Previte et al. |
| 2022/0186310 A1 | 6/2022 | Arslan et al. |
| 2022/0251643 A1 | 8/2022 | Chen et al. |
| 2022/0251644 A1 | 8/2022 | Chen et al. |
| 2022/0267842 A1 | 8/2022 | Chen et al. |
| 2022/0275437 A1 | 9/2022 | Stapleton et al. |
| 2022/0389408 A1 | 12/2022 | Ben-Yehezkel |
| 2023/0167434 A1 | 6/2023 | Kellinger et al. |
| 2023/0235392 A1 | 7/2023 | Arslan et al. |
| 2023/0295692 A1 | 9/2023 | Berti et al. |
| 2023/0296592 A1 | 9/2023 | Previte et al. |
| 2023/0296593 A1 | 9/2023 | Previte et al. |
| 2023/0323450 A1 | 10/2023 | Arslan et al. |
| 2024/0117428 A1 | 4/2024 | Previte et al. |
| 2024/0200133 A1 | 6/2024 | Ghorbani et al. |
| 2024/0201088 A1 | 6/2024 | Ghorbani et al. |
| 2024/0382956 A1 | 11/2024 | Guo et al. |

FOREIGN PATENT DOCUMENTS

| | | |
|---|---|---|
| WO | WO-0018957 A1 | 4/2000 |
| WO | WO-0109606 A1 | 2/2001 |
| WO | WO-0216023 A2 | 2/2002 |
| WO | WO-0243855 A1 | 6/2002 |
| WO | WO-03048723 A2 | 6/2003 |
| WO | WO-2007070542 A2 | 6/2007 |
| WO | WO-2008058282 A2 | 5/2008 |
| WO | WO-2010016937 A2 | 2/2010 |
| WO | WO-2010097655 A1 | 9/2010 |
| WO | WO-2012129242 A2 | 9/2012 |
| WO | WO-2014142981 A1 | 9/2014 |
| WO | WO-2014171898 A2 | 10/2014 |
| WO | WO-2015061362 A1 | 4/2015 |
| WO | WO-2015085268 A1 | 6/2015 |
| WO | WO-2015085274 A1 | 6/2015 |
| WO | WO-2016154345 A1 | 9/2016 |
| WO | WO-2017190012 A1 | 11/2017 |
| WO | WO-2017223517 A1 | 12/2017 |
| WO | WO-2018045109 A1 | 3/2018 |
| WO | WO-2019033062 A2 | 2/2019 |
| WO | WO-2019241305 A1 | 12/2019 |
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021146597 A1 | 7/2021 |
| WO | WO-2021236792 A1 | 11/2021 |
| WO | WO-2021252671 A2 | 12/2021 |
| WO | WO-2022026891 A1 | 2/2022 |
| WO | WO-2022094332 A1 | 5/2022 |
| WO | WO-2022266462 A2 | 12/2022 |
| WO | WO-2022266470 A1 | 12/2022 |
| WO | WO-2023004014 A1 | 1/2023 |
| WO | WO-2023107719 A2 | 6/2023 |
| WO | WO-2023196924 A2 | 10/2023 |
| WO | WO-2023205707 A2 | 10/2023 |
| WO | WO-2024118641 A1 | 6/2024 |
| WO | WO-2024151556 A1 | 7/2024 |
| WO | WO-2024158927 A2 | 8/2024 |
| WO | WO-2024173403 A2 | 8/2024 |

(56) References Cited

FOREIGN PATENT DOCUMENTS

OTHER PUBLICATIONS

Co-pending U.S. Appl. No. 18/426,101, inventors Arslan; Sinan et al., filed Jan. 29, 2024.
Co-pending U.S. Appl. No. 18/524,563, inventors Chen; Steve Xiangling et al., filed Nov. 30, 2023.
Co-pending U.S. Appl. No. 18/587,574, inventors Chen; Steve Xiangling et al., filed Feb. 26, 2024.
Co-pending U.S. Appl. No. 18/590,101, inventors Chen; Steve Xiangling et al., filed Feb. 28, 2024.
Co-pending U.S. Appl. No. 18/610,613, inventors Chen; Steve Xiangling et al., filed Mar. 20, 2024.
Co-pending U.S. Appl. No. 18/646,248, inventors Arslan; Sinan et al., filed Apr. 25, 2024.
Co-pending U.S. Appl. No. 18/680,203, inventors Guo; Minghao et al., filed May 31, 2024.
Co-pending U.S. Appl. No. 18/749,409, inventors Chen; Steve Xiangling et al., filed Jun. 20, 2024.
Co-pending U.S. Appl. No. 18/766,232, inventors Kellinger; Matthew et al., filed Jul. 8, 2024.
Adomas et al. Comparative analysis of transcript abundance in Pinus sylvestris after challenge with a saprotrophic, pathogenic or mutualistic fungus. Tree Physiol. 28:885-897 (2008).
Bharti et al.: A voltammetric hybridization assay for microRNA-21 using carboxylated graphene oxide decorated with gold-platinum bimetallic nanoparticles. Mikrochim Acta. 186(3):185, pp. 1-11 doi:10.1007/s00604-019-3302-3 (2019).
Cook et al. Solvent Effects on Hydrogen Bonding Angew. Chem. Int. Ed. 46:3706-3709 (2007).
Dave et al. Fast molecular beacon hybridization in organic solvents with improved target specificity. J. Phys. Chem. B 114:15694-15699 (2010).
"Dielectric Constants of Common Materials" provided by kabusa.com; [retrieved on Jan. 31, 2020]. Retrieved from the Internet: URL: kabusa.com/Dielectric-constants.pdf.
Fakruddin et al., Nucleic Acid Amplification: Alternative Methods of Polymerase Chain Reaction. J Pharm Bioallied Sci 5(4) :245-252 (2013).
Feng et al. Hydrophobic catalysis and a potential biological role of DNA unstacking induced by environment effect. PNAS USA 116(35)17169-17174 (2019).
Garibyan et al. Research Techniques Made Simple: Polymerase Chain Reaction (PCR). J. Invest. Dermatol. 133:e6 (2013).
Guttenberg et al. Planar chip device for PCR and hybridization with surface acoustic wave pump. Lab on a Chip 5(3):308-317 (2005).
Hacia et al. Determination of ancestral alleles for human single-nucleotide polymorphisms using high-density oligonucleotide arrays. Nat. Genet. 22:164-167 (1999).
Han. Improvement of the Speed and Sensitivity of DNA Hybridization Using Isotachophoresis, Stanford Thesis (139 pgs) (2015).
Heather et al. The Sequence of Sequencers: The History of Sequencing DNA. Genomics 107:1-8 (2016).
Heller. DNA microarray technology: devices, systems, and applications. Annu. Rev. Biomed. Eng. 4:129-53 (2002).
Huffman et al.: Effect of polar protic and polar aprotic solvents on negative-ion electrospray ionization and chromatographic separation of small acidic molecules. Anal Chem. 84(22):9942-9950 doi:10.1021/ac302397b (2012).
Kuhn et al. Hybridization of DNA and PNA molecular beacons to single-stranded and double-stranded DNA targets. J Am Chem Soc. 124(6):1097-103 (2002).
Lorenz: Polymerase chain reaction: basic protocol plus troubleshooting and optimization strategies. J Vis Exp. 63):e3998:1-14 doi:10.3791/3998 (2012).
Marx. Medicine. DNA arrays reveal cancer in its many forms. Science 289:1670-1672 (2000).

Monserud et al., Mechanisms of Surface-Mediated DNA Hybridization. ACS Nano 8(5):4488-4499 (2014).
Oldenbourg et al., Methods in Molecular Medicine: Analysis of Microtubule Dynamics by Polarized Light. Methods Mol Med 137: 111-123 (2007).
Palanisamy et al. Considerations of solid-phase DNA amplification. Bioconjug chem 21(4):690-695 (2010).
PCT/US2020/031161 International Search Report and Written Opinion dated Sep. 4, 2020.
Petracone et al. Studying the effect of crowding and dehydration on DNA G-quadruplexes. Methods 57(1):76-83 (2012).
Rosly et al.: Patterned Array of Poly(ethylene glycol) Silane Monolayer for Label-Free Detection of Dengue. Sensors (Basel) 16(9):1365, pp. 1-11 doi:10.3390/s16091365 (2016).
Ross et al. Systematic variation in gene expression patterns in human cancer cell lines. Nat Genet 24:227-235 (Mar. 2000).
Rychlik et al. Optimization of the annealing temperature for DNA amplification in vitro. Nucleic Acids Res. 18:6409-6412 (1990).
Schena et al. Quantitative monitoring of gene expression patterns with a complementary DNA microarray. Science 270:467-470 (1995).
Schlapak et al., Selective protein and DNA adsorption on PLL-PEG films modulated by ionic strength. Soft Matter. 5:613-621 (2009).
Sigma.com Product Information Formamide:F4761 and F7503 [retrieved on Feb. 9, 2021]. Retrieved from the Internet: URL: https://www.sigmaaldrich.com/content/dam/sigma-aldrich/docs/Sigald/Product_Information_Sheet/1/f7503pis.pdf (2021).
Snyder. Classification of the solvent properties of common liquids. Journal of Chromatography A 92(2):223-30 (1974).
Straus et al. Temperature dependence of RNA-DNA hybridization kinetics. Biochim. Biophys. Acta. 277:87-95 (1972).
Tyagi et al. Molecular Beacons: Probes that Fluoresce Upon Hybridization. Nature Biotechnology 14(3):303-308 (Mar. 1996).
U.S. Appl. No. 17/063,608 Non-Final Office Action dated Feb. 12, 2021.
U.S. Appl. No. 17/373,655 Final Office Action dated Jul. 18, 2023.
U.S. Appl. No. 17/373,655 Final Office Action dated Sep. 16, 2022.
U.S. Appl. No. 17/373,655 Non-Final Office Action dated Mar. 21, 2023.
U.S. Appl. No. 17/373,655 Non-Final Office Action dated Mar. 4, 2022.
U.S. Appl. No. 16/543,351 Final Office Action dated Jun. 24, 2020.
U.S. Appl. No. 16/543,351 Non-Final Office Action dated Feb. 6, 2020.
Watson. Molecular structure of nucleic acids. A structure for deoxyribose nucleic acid. 1953. JAMA 269:1966 (1993).
Wei et al. Recognition of single nucleotide polymorphisms using scanning potential hairpin denaturation. J. Am. Chem. Soc. 127:5306-5307 (2005).
Wetmur. Acceleration of DNA renaturation rates Biopolymers 14:2517-2524 (1975).
Wieder et al. One hundred-fold acceleration of DNA renaturation rates in solution. Biopolymers 20:1537-1547 (1981).
Wikipedia: List of water-miscible solvents [retrieved on Jul. 13, 2023]Retrieved from the Internet: URL:en.wikipedia.org/wiki/List_of_water-miscible_solvents (3 pages).
Wikipedia: MOPS [retrieved on Jul. 13, 2023]. Retrieved from the Internet: URL:en.wikipedia.org/wiki/MOPS (4 pages).
Xiao et al. Cell-specific internalization study of an aptamer from whole cell selection. Chemistry 14:1769-75 (2008).
Zanoli et al. Isothermal Amplification Methods for the Detection of Nucleic Acids in Microfluidic Devices. Biosensors 3:18-43 (2013).
Zhang et al., Effects of polyethylene glycol on DNA adsorption and hybridization on gold nanoparticles and graphene oxide. Langmuir. 28(40):14330-14337 (2012).
Zhang et al. Optimizing the specificity of nucleic acid hybridization. Nat. Chem. 4:208-14 (2012).
Co-pending U.S. Appl. No. 18/815,564, inventors Arslan; Sinan et al., filed Aug. 26, 2024.
Co-pending U.S. Appl. No. 18/919,127, inventors Liu; Tsung-Li et al., filed Oct. 17, 2024.

* cited by examiner

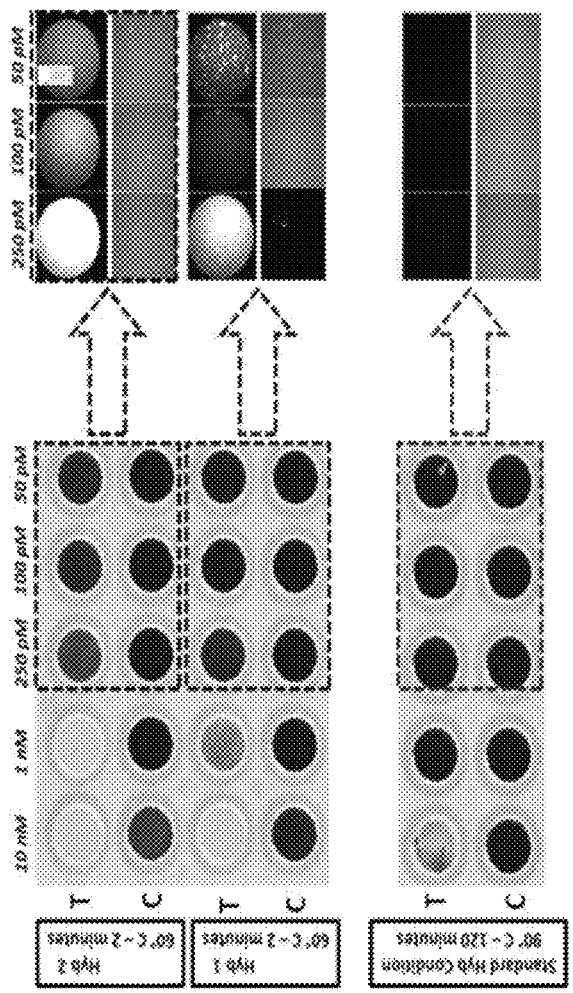
FIG. 3A
FIG. 3B
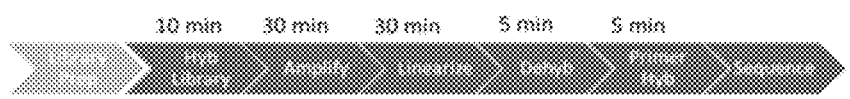
FIG. 4

MULTIVALENT BINDING COMPOSITION FOR NUCLEIC ACID ANALYSIS

CROSS REFERENCE

This application is a continuation-in-part of U.S. patent application Ser. No. 16/936,121 filed Jul. 22, 2020, now U.S. Pat. No. 12,117,438, which is a continuation of U.S. patent application Ser. No. 16/579,794 filed Sep. 23, 2019, now U.S. Pat. No. 10,768,173, which claims the benefit of U.S. Provisional Application No. 62/897,172 filed Sep. 6, 2019, each of which is incorporated herein by reference in its entirety. This application is also a continuation-in-part of U.S. patent application Ser. No. 18/415,517 filed Jan. 17, 2024, which is a continuation of U.S. patent application Ser. No. 17/373,655 filed Jul. 12, 2021, now abandoned, which is a continuation-in-part of International Patent Application No. PCT/US2020/031161 filed May 1, 2020, which is a continuation-in-part of U.S. patent application Ser. No. 16/543,351 filed Aug. 16, 2019, now abandoned, which claims the benefit of U.S. Provisional Application No. 62/841,541 filed May 1, 2019, each of which is incorporated herein by reference in its entirety.

FIELD

The present invention relates generally to multivalent binding compositions and their use in analyzing nucleic acid molecules. In particular, the invention relates to a multivalent binding composition having multiple copies of a nucleotide attached to a particle which effectively increases the local concentration of the nucleotide and enhances the binding signals. The multivalent binding composition can be applied, for example, in the field of sequencing and biosensor microarrays.

BACKGROUND

Nucleic acid sequencing can be used to obtain information in a wide variety of biomedical contexts, including diagnostics, prognostics, biotechnology, and forensic biology. Various sequencing methods have been developed including Maxam-Gilbert sequencing and chain-termination methods, or de novo sequencing methods including shotgun sequencing and bridge PCR, or next-generation methods including polony sequencing, 454 pyrosequencing, Illumina sequencing, SOLID sequencing, Ion Torrent semiconductor sequencing, HeliScope single molecule sequencing, SMRT® sequencing, and others. Despite advances in DNA sequencing, many challenges still remain unaddressed. The present disclosure provides novel solutions and approaches to addressing many of the shortcomings of existing technologies.

In typical fluorescence-based genomic testing assays, e.g., genotyping or nucleic acid sequencing (using either real time, cyclic, or stepwise reaction schemes), dye molecules that are attached to nucleic acid molecules tethered on a substrate are excited using an excitation light source, a fluorescence photon signal is generated in one or more spatially-localized positions on the substrate, and the fluorescence is subsequently imaged through an optical system onto an image sensor. An analysis process is then used to analyze the images, find the positions of labeled molecules (or clonally amplified clusters of molecules) on the substrate, and quantify the fluorescence photon signal in terms of wavelength and spatial coordinates, which may then be correlated with the degree to which a specific chemical reaction, e.g., a hybridization event or base addition event, occurred in the specified locations on the substrate. Imaging-based methods provide large scale parallelism and multiplexing capabilities, which help to drive down the cost and accessibility of such technologies. However, detection errors that arise from, for example, overly dense packing of labeled molecules (or clonally-amplified clusters of molecules) within a small region of the substrate surface, or due to low contrast-to-noise ratio (CNR) in the image, may lead to errors in attributing the fluorescence signal to the correct molecules (or clonally amplified clusters of molecules).

This disclosure herein also relates to the field of molecular biology, such as compositions, methods, and systems for nucleic acid hybridization. In particular, it relates to hybridization compositions and methods for nucleic acid that is attached to a surface.

Nucleic acid hybridization protocols constitute an important part of many different nucleic acid amplification and analysis techniques. The limited specificity and reaction rates achieved through the use of existing nucleic acid hybridization protocols can have detrimental effects on the throughput and accuracy of downstream nucleic acid analysis methods. Methods of stringency control often involve conditions causing a significant decrease in the number of hybridized complexes. Therefore, there is a need for an improved method to achieve a high stringency of hybridization during the sequencing analysis.

INCORPORATION BY REFERENCE OF SEQUENCE LISTING

The present application is being filed along with a Sequence Listing in electronic format. The Sequence Listing is provided as a file entitled 52933-723_502SL.XML, created Feb. 2, 2024, which is 2,622 bytes in size. The information in the electronic format of the Sequence Listing is incorporated by reference in its entirety.

SUMMARY

In some embodiments the present disclosure provides a method of determining the identity of a nucleotide in a target nucleic acid comprising the steps, without regard to any particular order of operations, 1) providing a composition comprising: a target nucleic acid; a primer nucleic acid complementary to one or more regions of said target nucleic acid; and a polymerase molecule; 2) contacting said composition with a binding composition comprising a polymer-nucleotide conjugate under conditions sufficient to allow a binding complex to be formed between said polymer-nucleotide conjugate and the composition of step (a), wherein the polymer-nucleotide conjugate comprises a nucleotide and optionally one or more detectable labels; and 3) detecting said binding complex, thereby establishing the identity of said nucleotide in the target nucleic acid polymer. In some further embodiments, the present disclosure provides said method, wherein the target nucleic acid is DNA, and/or wherein the target nucleic acid has been replicated, such as by any commonly practiced method of DNA replication or amplification, such as rolling circle amplification, bridge amplification, helicase dependent amplification, isothermal bridge amplification, rolling circle multiple displacement amplification (RCA/MDA) and/or recombinase based methods of replication or amplification. In some further embodiments, the present disclosure provides said method, wherein the detectable label is a fluorescent label and/or wherein detecting the binding complex comprises a fluorescence measurement. In some further embodiments, the present disclosure provides said method wherein the binding composition comprises one type of polymer-nucleotide conjugate, wherein the multivalent binding composition comprises two or more types of polymer-nucleotide conjugates, and/or wherein each type of the two or more types of polymer-nucleotide conjugates comprises a different type of nucleotide. In some embodiments, the present disclosure provides said method wherein the binding complex further comprises a blocked nucleotide, especially wherein the blocked nucleotide is a 3'-O-azidomethyl, a 3'-O-alkyl hydroxylamino or 3'-O-methyl nucleotide. In some further embodiments, the present disclosure provides said method wherein the contacting is done in the presence of strontium ions, magnesium ions, and/or calcium ions. In some embodiments, the present disclosure provides said method wherein the polymerase molecule is catalytically inactive, such as where the polymerase molecule been rendered catalytically inactive by mutation, by chemical modification, or by the absence of a necessary ion or cofactor. In some embodiments, the present disclosure also provides said method wherein the polymerase molecule is catalytically active, and/or wherein the binding complex does not comprise a blocked nucleotide. In some embodiments, the present disclosure provides said method wherein the binding complex has a persistence time of greater than 2 seconds and/or wherein the method is or may be carried out at a temperature of at or above 15° C., at or above 20° C., at or above 25° C., at or above 35° C., at or above 37° C., at or above 42° C. at or above 55° C. at or above 60° C., or at or above 72° C., or within a range defined by any of the foregoing. In some embodiments, the present disclosure provides said method wherein the binding complex is deposited on, attached to, or hybridized to, a surface showing a contrast to noise ratio in the detecting step of greater than 20. In some embodiments, the present disclosure provides said method wherein the composition is deposited under buffer conditions incorporating a polar aprotic solvent. In some embodiments, the present disclosure provides said method wherein the contacting is performed under a condition that stabilizes said binding complex when said nucleotide is complementary to a next base of said target nucleic acid, and destabilizes said binding complex when said nucleotide is not complementary to said next base of said target nucleic acid. In some embodiments, the present disclosure provides said method wherein said polymer-nucleotide conjugate comprises a polymer having a plurality of branches and said plurality of copies of said first nucleotide are attached to said branches, especially wherein said first polymer has a star, comb, cross-linked, bottle brush, or dendrimer configuration. In some embodiments, the present disclosure provides said method wherein said polymer-nucleotide conjugate comprises one or more binding groups selected from the group consisting of avidin, biotin, affinity tag, and combinations thereof. In some embodiments, the present disclosure provides said method further comprising a dissociation step that destabilizes said binding complex formed between the composition of (a) and the polymer-nucleotide conjugate to remove said polymer-nucleotide conjugate. In some embodiments, the present disclosure provides said method further comprising an extension step to incorporate into said primer nucleic acid a nucleotide that is complementary to said next base of the target nucleic acid, and optionally wherein the extension step occurs currently as or after said dissociation step.

In some embodiments the present disclosure provides a method for attaching a target nucleic acid molecule to a surface, the method comprising: bringing a mixture comprising said target nucleic acid molecule at a concentration of 1 nanomolar or less in contact with a hydrophilic surface comprising a capture probe coupled thereto under conditions sufficient for said target nucleic acid molecule to be captured by said capture probe in a time period of less than 30 minutes. In some embodiments, said mixture comprises a polar aprotic solvent. In some embodiments, said capture probe is a nucleic acid molecule. In some embodiments, said concentration is 0.50 nanomolar or less. In some embodiments, said concentration is 250 picomolar or less. In some embodiments, said concentration is 100 picomolar or less. In some embodiments, said time period is less than or equal to 20 minutes. In some embodiments, said time period is less than or equal to 15 minutes. In some embodiments, said time period is less than or equal to 10 minutes. In some embodiments, said time period is less than or equal to 5 minutes.

In some embodiments, said hydrophilic surface is maintained at a temperature of about 30 degrees Celsius to about 70 degrees Celsius. In some embodiments, said hydrophilic surface is maintained at a substantially constant temperature. In some embodiments, methods further comprise hybridizing the target nucleic acid molecule to the capture probe at a hybridization efficiency that is increased as compared to a comparable hybridization reaction performed for 120 minutes at 90 degrees Celsius for 5 minutes followed by cooling for 120 minutes to reach a final temperature of 37 degrees Celsius in a buffer composition comprising saline-sodium citrate. In some embodiments, methods further comprise hybridizing the target nucleic acid molecule to the capture probe with a hybridization stringency of at least 80%.

In some embodiments, the hydrophilic surface exhibits a level of non-specific Cyanine 3 dye absorption of less than about 0.25 molecules per square micrometer. In some embodiments, the mixture further comprises a pH buffer comprising 2-(N-morpholino)ethanesulfonic acid, acetonitrile, 3-(N-morpholino)propanesulfonic acid, methanol, or a combination thereof. In some embodiments, the mixture further comprises a crowding agent selected from the group consisting of polyethylene glycol, dextran, hydroxypropyl methyl cellulose, hydroxyethyl methyl cellulose, hydroxybutyl methyl cellulose, hydroxypropyl cellulose, methyl cellulose, and hydroxyl methyl cellulose, and any combination thereof. In some embodiments, the hydrophilic surface comprises one or more hydrophilic polymer layers. In some embodiments, the one or more hydrophilic polymer layers comprises a molecule selected from the group consisting of polyethylene glycol (PEG), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(2-hydroxyethyl methacrylate) (PHEMA), poly(oligo (ethylene glycol) methyl ether methacrylate) (POEGMA), polyglutamic acid (PGA), poly-lysine, poly-glucoside, streptavidin, and dextran. In some embodiments, the one or more hydrophilic polymer layers comprises at least one dendrimer.

Provided herein are methods for hybridizing a target nucleic acid molecule to a nucleic acid molecule coupled to a hydrophilic polymer surface, the method comprising: (a) providing at least one nucleic acid molecule that is coupled to a hydrophilic polymer surface; and (b) bringing the at least one nucleic acid molecule coupled to the polymer surface into contact with a hybridizing composition comprising a target nucleic acid molecule at a concentration of 1 nanomolar or less under conditions sufficient for said target nucleic acid molecule to hybridize to the at least one nucleic acid molecule coupled to the polymer surface in 30 minutes or less. In some embodiments, said conditions are maintained at a substantially constant temperature.

In some embodiments, the hydrophilic polymer surface has a water contact angle of less than 45 degrees. In some embodiments, the target nucleic acid molecule is present in the hybridizing composition at a concentration of 0.50 nanomolar or less. In some embodiments, the target nucleic acid molecule is present in the hybridizing composition at a concentration of 250 picomolar or less. In some embodiments, the target nucleic acid molecule is present in the hybridizing composition at a concentration of 100 picomolar or less. In some embodiments, bringing the at least one nucleic acid molecule coupled to the polymer surface into contact with the hybridization composition is performed for a time period of less than 30 minutes. In some embodiments, the time period is less than 20 minutes. In some embodiments, the time period is less than 15 minutes. In some embodiments, the time period is less than 10 minutes. In some embodiments, the time period is less than 5 minutes.

In some embodiments, methods further comprise hybridizing the target nucleic acid molecule to the at least one nucleic molecule coupled to the polymer surface at a hybridization efficiency that is increased as compared to a comparable hybridization reaction performed for 120 minutes at 90 degrees Celsius for 5 minutes followed by cooling for 120 minutes to reach a final temperature of 37 degrees Celsius in a buffer comprising saline-sodium citrate. In some embodiments, the temperature is from about 30 degrees Celsius to 70 degrees Celsius. In some embodiments, the temperature is about 50 degrees Celsius. In some embodiments, methods further comprise hybridizing the target nucleic acid molecule to the at least one nucleic acid molecule with a hybridization stringency of at least 80%. In some embodiments, the hydrophilic polymer surface exhibits a level of non-specific Cyanine 3 dye absorption of less than about 0.25 molecules per square micrometer.

In some embodiments, the hybridization composition further comprises: (a) at least one organic solvent having a dielectric constant of no greater than about 115 as measured at 68 degrees Fahrenheit; and (b) a pH buffer. In some embodiments, the hybridization composition further comprises: (a) at least one organic solvent that is polar and aprotic; and (b) a pH buffer. In some embodiments, the at least one organic solvent comprises at least one functional group selected from hydroxy, nitrile, lactone, sulfone, sulfite, and carbonate. In some embodiments, the at least one organic solvent comprises formamide. In some embodiments, the at least one organic solvent is miscible with water. In some embodiments, the at least one organic solvent is at least about 5% by volume based on the total volume of the hybridizing composition. In some embodiments, the at least one organic solvent is at most about 95% by volume based on the total volume of the hybridizing composition.

In some embodiments, the pH buffer is at most about 90% by volume of the total volume of the hybridizing composition. In some embodiments, the pH buffer comprises 2-(N-morpholino)ethanesulfonic acid, acetonitrile, 3-(N-morpholino)propanesulfonic acid, methanol, or a combination thereof. In some embodiments, the pH buffer further comprises a second organic solvent. In some embodiments, the pH buffer is present in the hybridizing composition in an amount that is effective to maintain the pH of the hybridizing composition in a range of about 3 to about 10.

In some embodiments, the hybridizing composition further comprises a molecular crowding agent. In some embodiments, the molecular crowding agent is selected from the group consisting of polyethylene glycol, dextran, hydroxypropyl methyl cellulose, hydroxyethyl methyl cellulose, hydroxybutyl methyl cellulose, hydroxypropyl cellulose, methyl cellulose, and hydroxyl methyl cellulose, and any combination thereof. In some embodiments, the molecular crowding agent is polyethylene glycol. In some embodiments, the molecular crowding agent has a molecular weight in the range of about 5,000 to 40,000 Daltons. In some embodiments, an amount of the molecular crowding agent is at least about 5% by volume based on the total volume of the hybridizing composition. In some embodiments, an amount of the molecular crowding agent at most about 50% by volume based on the total volume of the hybridizing composition. In some embodiments, the at least one nucleic acid molecule coupled to the polymer surface is coupled to the polymer surface through covalent bonding.

In some embodiments, the hydrophilic polymer surface comprises one or more hydrophilic polymer layers, and wherein the at least one nucleic acid molecule is coupled to the one or more hydrophilic polymer layers. In some embodiments, the one or more hydrophilic polymer layers comprises a molecule selected from the group consisting of polyethylene glycol (PEG), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, and dextran. In some embodiments, the one or more hydrophilic polymer layers comprises at least one dendrimer.

Provided herein are methods of attaching a target nucleic acid to a surface, comprising: (a) providing at least one surface bound nucleic acid that is attached to a polymer surface having a water contact angle comprises less than 45 degrees; and (b) bringing the surface bound nucleic acid into contact with a hybridizing composition under isothermal conditions, wherein the hybridizing composition comprises: (i) the target nucleic acid; (ii) at least one organic solvent having a dielectric constant of no greater than about 115 when measured at 68 degrees Fahrenheit; and (iii) a pH buffer.

In some embodiments, the organic solvent is a polar aprotic solvent. In some embodiments, the organic solvent is an organic solvent having a dielectric constant of no greater than 40 when measured at 68 degrees Fahrenheit. In some embodiments, the organic solvent is acetonitrile, alcohol, or formamide. In some embodiments, the organic solvent comprises at least one functionality selected from hydroxy, nitrile, lactone, sulfone, sulfite, and carbonate. In some embodiments, the organic solvent is miscible with water. In some embodiments, the organic solvent is present in an amount effective to denature a double stranded nucleic acid. In some embodiments, an amount of the organic solvent is at least about 5% by volume based on the total volume of the hybridizing composition. In some embodiments, an amount of the organic solvent is in the range of about 5% to 95% by volume based on the total volume of the hybridizing composition. In some embodiments, an amount of the pH buffer is no greater than 90% by volume based on the total volume of the hybridizing composition. In some embodiments, the hybridizing composition further comprises a molecular crowding agent. In some embodiments, the molecular crowding agent is selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose, and any combination thereof. In some embodiments, the molecular crowding agent is polyethylene glycol (PEG). In some embodiments, the molecular crowding agent has a molecular weight in the range of about 5,000 to 40,000 Daltons. In some embodiments, an amount of the molecular crowding agent is at least about 5% by volume based on the total volume of the hybridizing composition. In some embodiments, an amount of the molecular crowding agent is less than 50% by volume based on the total volume of the hybridizing composition. In some embodiments, methods further comprise an additive for controlling a melting temperature of the target nucleic acid. In some embodiments, an amount of the additive for controlling melting temperature of the target nucleic acid is at least about 2% by volume based on the total volume of the hybridizing composition. In some embodiments, an amount of the additive for controlling melting temperature of the nucleic acid is in the range of about 2% to 50% by volume based on the total volume of the hybridizing composition. In some embodiments, the pH buffer comprises at least one buffering agent selected from the group consisting of Tris, HEPES (e.g., 4-(2-hydroxyethyl)-1-piperazineethanesulfonic acid), TAPS (e.g., [tris(hydroxymethyl)methylamino]propanesulfonic acid), Tricine, Bicine, Bis-Tris, sodium hydroxide (NaOH), potassium hydroxide (KOH), TES (e.g., 2-[[1,3-dihydroxy-2-(hydroxymethyl)propan-2-yl]amino]ethanesulfonic acid), EPPS (e.g., 4-(2-Hydroxyethyl)-1-piperazinepropanesulfonic acid, 4-(2-Hydroxyethyl)piperazine-1-propanesulfonic acid, N-(2-Hydroxyethyl)piperazine-N'-(3-propanesulfonic acid)), and MOPS (e.g., 3-(N-morpholino)propanesulfonic acid). In some embodiments, the pH buffer further comprises a second organic solvent. In some embodiments, the pH buffer comprises MOPS and methanol. In some embodiments, an amount of the pH buffer is effective to maintain the pH of the hybridizing composition to be in the range of about 3 to about 10.

In some embodiments, the surface bound nucleic acid is coupled to the surface through covalent or noncovalent bonding. In some embodiments, the polymer surface comprises one or more hydrophilic polymer layers, and wherein the surface bound nucleic acid is coupled to the one or more hydrophilic polymer layers. In some embodiments, no more than 10% of the target nucleic acid is associated with the surface without hybridizing to the polymer surface bound nucleic acid. In some embodiments, the polymer surface exhibits a level of non-specific cyanine 3 (Cy3) dye absorption of less than about 0.25 molecules per micrometer squared ($\mu m^2$). In some embodiments, the one or more hydrophilic polymer layers comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the one or more hydrophilic polymer layers comprises at least one dendrimer.

In some embodiments, bringing the surface bound nucleic acid into contact with the hybridizing composition is performed for a period of no more than 25 minutes. In some embodiments, bringing the surface bound nucleic acid into contact with the hybridizing composition is performed for a period of no more than 15 minutes. In some embodiments, bringing the surface bound nucleic acid into contact with the hybridizing composition is performed for a period between 2-25 minutes. In some embodiments, the isothermal conditions are at a temperature in the range of about 30 to 70 degrees Celsius. In some embodiments, comprising hybridizing the target nucleic acid to the surface bound nucleic with a hybridization stringency of at least 80%. In some embodiments, comprising hybridizing the target nucleic acid to the surface bound nucleic with an increased hybridization efficiency, as compared to a comparable hybridization reaction wherein the organic buffer is a saline-sodium citrate and hybridizing is performed for 120 minutes at 90 degrees Celsius for 5 minutes followed by cooling for 120 minutes to reach a final temperature of 37 degrees Celsius. In some embodiments, the target nucleic acid is present in the hybridizing composition at a 1 nanomolar concentration or less. In some embodiments, the target nucleic acid is present in the hybridizing composition at a 250 picomolar concentration or less. In some embodiments, the target nucleic acid is present in the hybridizing composition at a 100 picomolar concentration or less. In some embodiments, the target nucleic acid is present in the hybridizing composition at a 50 picomolar concentration or less. In some embodiments, methods further comprise hybridizing at least a portion of the surface bound nucleic acid to at least a portion of the target nucleic acid in the hybridizing composition, which hybridizing does not consist of cooling.

Provided herein are methods of hybridization, the method comprising: (a) providing at least one surface bound nucleic acid molecule coupled to a surface; and (b) bringing the at least one surface bound nucleic acid molecule into contact with a hybridizing composition comprising a target nucleic acid molecule, wherein the hybridizing composition comprises: (i) at least one organic solvent; and (ii) a pH buffer. In some embodiments, the surface exhibits a level of nonspecific Cy3 dye absorption corresponding to less than about 0.25 molecules/$\mu m^2$ when measured by a fluorescence imaging system under non-signal saturating conditions. In some embodiments, no more than 5% of a total number of the target nucleic acid molecule is associated with the surface without hybridizing to the surface bound nucleic acid molecule.

In some embodiments, the surface bound nucleic acid molecule is coupled to the surface by being tethered to the surface. In some embodiments, the surface is a hydrophilic polymer surface. In some embodiments, the surface has a water contact angle of less than 45 degrees. In some embodiments, the at least one organic solvent has a dielectric constant of no greater than about 115 when measured at 68 degrees Fahrenheit. In some embodiments, the organic solvent is a polar aprotic solvent. In some embodiments, the organic solvent is an organic solvent having a dielectric constant of no greater than 40 when measured at 68 degrees Fahrenheit. In some embodiments, the organic solvent is acetonitrile, alcohol, or formamide. In some embodiments, the organic solvent comprises at least one functionality selected from hydroxy, nitrile, lactone, sulfone, sulfite, and carbonate. In some embodiments, the organic solvent is miscible with water. In some embodiments, the organic solvent is present in an amount effective to denature a double stranded nucleic acid. In some embodiments, an amount of the organic solvent is at least about 5% by volume based on the total volume of the hybridizing composition. In some embodiments, an amount of the organic solvent is in the range of about 5% to 95% by volume based on the total volume of the hybridizing composition. In some embodiments, an amount of the pH buffer is no greater than 90% by volume based on the total volume of the hybridizing composition. In some embodiments, the hybridizing composition further comprises a molecular crowding agent. In some embodiments, the molecular crowding agent is selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose, and any combination thereof. In some embodiments, the molecular crowding agent is polyethylene glycol (PEG). In some embodiments, the molecular crowding agent has a molecular weight in the range of about 5,000 to 40,000 Daltons. In some embodiments, an amount of the molecular crowding agent is at least about 5% by volume based on the total volume of the hybridizing composition. In some embodiments, an amount of the molecular crowding agent is less than 50% by volume based on the total volume of the hybridizing composition. In some embodiments, methods further comprise an additive for controlling a melting temperature of the target nucleic acid. In some embodiments, an amount of the additive for controlling melting temperature of the target nucleic acid is at least about 2% by volume based on the total volume of the hybridizing composition. In some embodiments, an amount of the additive for controlling melting temperature of the nucleic acid is in the range of about 2% to 50% by volume based on the total volume of the hybridizing composition. In some embodiments, the pH buffer comprises at least one buffering agent selected from the group consisting of Tris, HEPES, TAPS, Tricine, Bicine, Bis-Tris, sodium hydroxide (NaOH), potassium hydroxide (KOH), TES, EPPS, and MOPS. In some embodiments, the pH buffer further comprises a second organic solvent. In some embodiments, the pH buffer comprises MOPS and methanol. In some embodiments, an amount of the pH buffer is effective to maintain the pH of the hybridizing composition to be in the range of about 3 to about 10. In some embodiments, the surface bound nucleic acid is coupled to the surface through covalent or noncovalent bonding. In some embodiments, the polymer surface comprises one or more hydrophilic polymer layers, and wherein the surface bound nucleic acid is coupled to the one or more hydrophilic polymer layers. In some embodiments, no more than 10% of the target nucleic acid is associated with the surface without hybridizing to the polymer surface bound nucleic acid. In some embodiments, the one or more hydrophilic polymer layers comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the one or more hydrophilic polymer layers comprises at least one dendrimer.

In some embodiments, bringing the surface bound nucleic acid molecule into contact with the hybridizing composition is performed for a period of no more than 25 minutes. In some embodiments, bringing the surface bound nucleic acid molecule into contact with the hybridizing composition is performed for a period of no more than 15 minutes. In some embodiments, bringing the surface bound nucleic acid molecule into contact with the hybridizing composition is performed for a period between 2-25 minutes. In some embodiments, the isothermal conditions are at a temperature in the range of about 30 to 70 degrees Celsius. In some embodiments, comprising hybridizing the target nucleic acid molecule to the surface bound nucleic acid molecule with a hybridization stringency of at least 80%. In some embodiments, comprising hybridizing the target nucleic acid molecule to the surface bound nucleic acid molecule with an increased hybridization efficiency, as compared to a comparable hybridization reaction wherein the organic buffer is a saline-sodium citrate and hybridizing is performed for 120 minutes at 90 degrees Celsius for 5 minutes followed by cooling for 120 minutes to reach a final temperature of 37 degrees Celsius. In some embodiments, the target nucleic acid molecule is present in the hybridizing composition at a 1 nanomolar concentration or less. In some embodiments, the target nucleic acid is present in the hybridizing composition at a 250 picomolar concentration or less. In some embodiments, the target nucleic acid molecule is present in the hybridizing composition at a 100 picomolar concentration or less. In some embodiments, the target nucleic acid molecule is present in the hybridizing composition at a 50 picomolar concentration or less. In some embodiments, methods further comprise hybridizing at least a portion of the surface bound nucleic acid molecule to at least a portion of the target nucleic acid molecule in the hybridizing composition, which hybridizing does not consist of cooling. In some embodiments, bringing the surface bound nucleic acid into contact with the hybridizing composition comprising the target nucleic acid is performed under conditions of stringency that prevent the target nucleic acid molecule from hybridizing to a non-complementary nucleic acid molecule. In some embodiments, the stringency is at least or about 70%, 80%, or 90%. In some embodiments, the stringency is at least 80%. Provided herein are methods of attaching a target nucleic acid molecule to a surface, the method comprising: (a) providing at least one surface bound nucleic acid molecule, wherein the at least one surface bound nucleic acid molecule is coupled to a surface; and (b) bringing a hybridizing composition comprising a target nucleic acid molecule into contact with the at least one surface bound nucleic acid molecule, wherein the hybridizing composition comprises: (i) at least one organic solvent; and (ii) a pH buffer. In some embodiments, the surface exhibits a level of non-specific Cy3 dye absorption of less than about 0.25 molecules/µm$^2$. In some embodiments, no more than 5% of a total number of the target nucleic acid molecule is associated with the surface without hybridizing to the surface bound nucleic acid molecule. In some embodiments, bringing the hybridizing composition into contact with the at least one surface bound nucleic acid molecule is performed under isothermic conditions. In some embodiments, the surface bound nucleic acid molecule is coupled to the surface by being tethered to the surface. In some embodiments, the surface is a hydrophilic polymer surface. In some embodiments, the surface has a water contact angle of less than 45 degrees.

In some embodiments, the at least one organic solvent has a dielectric constant of no greater than about 115 when measured at 68 degrees Fahrenheit. In some embodiments, the organic solvent is a polar aprotic solvent. In some embodiments, the organic solvent is an organic solvent having a dielectric constant of no greater than 40 when measured at 70 degrees Fahrenheit. In some embodiments, the organic solvent is acetonitrile, alcohol, or formamide. In some embodiments, the organic solvent comprises at least one functionality selected from hydroxy, nitrile, lactone, sulfone, sulfite, and carbonate. In some embodiments, the organic solvent is miscible with water. In some embodiments, the organic solvent is present in an amount effective to denature a double stranded nucleic acid. In some embodiments, an amount of the organic solvent is at least about 5% by volume based on the total volume of the hybridizing composition. In some embodiments, an amount of the organic solvent is in the range of about 5% to 95% by volume based on the total volume of the hybridizing composition. In some embodiments, an amount of the pH buffer is no greater than 90% by volume based on the total volume of the hybridizing composition. In some embodiments, the hybridizing composition further comprises a molecular crowding agent. In some embodiments, the molecular crowding agent is selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose, and any combination thereof. In some embodiments, the molecular crowding agent is polyethylene glycol (PEG). In some embodiments, the molecular crowding agent has a molecular weight in the range of about 5,000 to 40,000 Daltons. In some embodiments, an amount of the molecular crowding agent is at least about 5% by volume based on the total volume of the hybridizing composition. In some embodiments, an amount of the molecular crowding agent is less than 50% by volume based on the total volume of the hybridizing composition. In some embodiments, methods further comprise an additive for controlling a melting temperature of the target nucleic acid. In some embodiments, an amount of the additive for controlling melting temperature of the target nucleic acid molecule is at least about 2% by volume based on the total volume of the hybridizing composition. In some embodiments, an amount of the additive for controlling melting temperature of the nucleic acid is in the range of about 2% to 50% by volume based on the total volume of the hybridizing composition. In some embodiments, the pH buffer comprises at least one buffering agent selected from the group consisting of Tris, HEPES, TAPS, Tricine, Bicine, Bis-Tris, sodium hydroxide (NaOH), potassium hydroxide (KOH), TES, EPPS, and MOPS. In some embodiments, the pH buffer further comprises a second organic solvent. In some embodiments, the pH buffer comprises MOPS and methanol. In some embodiments, an amount of the pH buffer is effective to maintain the pH of the hybridizing composition to be in the range of about 3 to about 10.

In some embodiments, the surface bound nucleic acid molecule is coupled to the surface through covalent or noncovalent bonding. In some embodiments, the polymer surface comprises one or more hydrophilic polymer layers, and wherein the surface bound nucleic acid is coupled to the one or more hydrophilic polymer layers. In some embodiments, no more than 10% of the total number of the target nucleic acid molecule is associated with the surface without hybridizing to the polymer surface bound nucleic acid molecule. In some embodiments, the one or more hydrophilic polymer layers comprises a molecule selected from the group consisting of polyethylene glycol (PEG), poly (vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the one or more hydrophilic polymer layers comprises at least one dendrimer. In some embodiments, bringing the surface bound nucleic acid molecule into contact with the hybridizing composition is performed for a period of no more than 25 minutes. In some embodiments, bringing the surface bound nucleic acid molecule into contact with the hybridizing composition is performed for a period of no more than 15 minutes. In some embodiments, bringing the surface bound nucleic acid molecule into contact with the hybridizing composition is performed for a period between 2-25 minutes. In some embodiments, the isothermal conditions are at a temperature in the range of about 30 to 70 degrees Celsius. In some embodiments, comprising hybridizing the target nucleic acid molecule to the surface bound nucleic molecule with a hybridization stringency of at least 80%. In some embodiments, comprising hybridizing the target nucleic acid molecule to the surface bound nucleic acid molecule with an increased hybridization efficiency, as compared to a comparable hybridization reaction wherein the organic buffer is a saline-sodium citrate and hybridizing is performed for 120 minutes at 90 degrees Celsius for 5 minutes followed by cooling for 120 minutes to reach a final temperature of 37 degrees Celsius. In some embodiments, the target nucleic acid molecule is present in the hybridizing composition at a 1 nanomolar concentration or less. In some embodiments, the target nucleic acid molecule is present in the hybridizing composition at a 250 picomolar concentration or less. In some embodiments, the target nucleic acid molecule is present in the hybridizing composition at a 100 picomolar concentration or less. In some embodiments, the target nucleic acid molecule is present in the hybridizing composition at a 50 picomolar concentration or less. In some embodiments, methods further comprise hybridizing at least a portion of the surface bound nucleic acid molecule to at least a portion of the target nucleic acid molecule in the hybridizing composition, which hybridizing does not consist of cooling.

Provided herein are methods of sequencing a target nucleic acid molecule, the method comprising: (a) bringing a surface bound nucleic acid molecule coupled to a surface into contact with a hybridizing compositions comprising a target nucleic acid molecule, wherein the hybridizing composition comprises: (i) at least one organic solvent; and (ii) a pH buffer; (b) amplifying the target nucleic acid molecule to form a plurality of clonally-amplified clusters of the target nucleic acid; and (c) determining the identity of the target nucleic acid molecule, wherein a fluorescence image of the surface comprising the plurality of clonally-amplified clusters of the target nucleic acid molecule exhibits a contrast-to-noise ratio (CNR) of at least 20 when the fluorescence image is captured using a fluorescence imaging system under non-signal saturating conditions. In some embodiments, methods further comprise hybridizing the target nucleic acid molecule to the at least one surface bound nucleic acid coupled to the surface. In some embodiments, the CNR is at least 50. In some embodiments, the organic solvent is a polar aprotic solvent. In some embodiments, the organic solvent is an organic solvent having a dielectric constant of no greater than 40 as measured at 70 degrees Fahrenheit. In some embodiments, the organic solvent is acetonitrile, alcohol, or formamide. In some embodiments, the organic solvent comprises at least one functionality selected from hydroxy, nitrile, lactone, sulfone, sulfite, and carbonate. In some embodiments, the organic solvent is miscible with water. In some embodiments, the organic solvent is present in an amount effective to denature a double stranded nucleic acid. In some embodiments, an amount of the organic solvent is at least about 5% by volume based on the total volume of the hybridizing composition. In some embodiments, an amount of the organic solvent is in the range of about 5% to 95% by volume based on the total volume of the hybridizing composition. In some embodiments, an amount of the pH buffer is no greater than 90% by volume based on the total volume of the hybridizing composition. In some embodiments, the hybridizing composition further comprises a molecular crowding agent. In some embodiments, the molecular crowding agent is selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose, and any combination thereof. In some embodiments, the molecular crowding agent is polyethylene glycol (PEG). In some embodiments, the molecular crowding agent has a molecular weight in the range of about 5,000 to 40,000 Daltons. In some embodiments, an amount of the molecular crowding agent is at least about 5% by volume based on the total volume of the hybridizing composition. In some embodiments, an amount of the molecular crowding agent is less than 50% by volume based on the total volume of the hybridizing composition. In some embodiments, methods further comprise an additive for controlling a melting temperature of the target nucleic acid molecule. In some embodiments, an amount of the additive for controlling melting temperature of the target nucleic acid is at least about 2% by volume based on the total volume of the hybridizing composition. In some embodiments, an amount of the additive for controlling melting temperature of the nucleic acid molecule is in the range of about 2% to 50% by volume based on the total volume of the hybridizing composition. In some embodiments, the pH buffer comprises at least one buffering agent selected from the group consisting of Tris, HEPES, TAPS, Tricine, Bicine, Bis-Tris, sodium hydroxide (NaOH), potassium hydroxide (KOH), TES, EPPS, and MOPS. In some embodiments, the pH buffer further comprises a second organic solvent. In some embodiments, the pH buffer comprises MOPS and methanol. In some embodiments, an amount of the pH buffer is effective to maintain the pH of the hybridizing composition to be in the range of about 3 to about 10.

In some embodiments, the surface bound nucleic acid molecule is coupled to the surface through covalent or noncovalent bonding. In some embodiments, the polymer surface comprises one or more hydrophilic polymer layers, and wherein the surface bound nucleic acid molecule is coupled to the one or more hydrophilic polymer layers. In some embodiments, the polymer surface exhibits a level of non-specific Cyanine3 (Cy3) dye absorption of less than about 0.25 molecules per micrometer squared ($\mu m^2$). In some embodiments, no more than 5% of a total number of the target nucleic acid molecule is associated with the surface without hybridizing to the surface bound nucleic acid molecule. In some embodiments, no more than 10% of the total number of the target nucleic acid molecule is associated with the surface without hybridizing to the surface bound nucleic acid molecule. In some embodiments, the one or more hydrophilic polymer layers comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the one or more hydrophilic polymer layers comprises at least one dendrimer. In some embodiments, bringing the surface bound nucleic acid molecule into contact with the hybridizing composition is performed under isothermic conditions. In some embodiments, bringing the surface bound nucleic acid molecule into contact with the hybridizing composition is performed at a temperature in the range of about 30 to 70 degrees Celsius. In some embodiments, bringing the surface bound nucleic acid molecule into contact with the hybridizing composition is performed for a period of no more than 25 minutes. In some embodiments, methods further comprise removing the hybridizing composition from the surface after the period of no more than 25 minutes. In some embodiments, bringing the surface bound nucleic acid molecule into contact with the hybridizing composition is performed for a period between 2-25 minutes. In some embodiments, bringing the surface bound nucleic acid molecule into contact with the hybridizing composition is performed for a period between 2-4 minutes. In some embodiments, bringing the surface bound nucleic acid molecule into contact with the hybridizing composition is performed for a period of 2 minutes. In some embodiments, the at least one surface bound nucleic acid molecule is circular. In some embodiments, methods further comprise hybridizing at least a portion of the surface bound nucleic acid molecule to at least a portion of the target nucleic acid in the hybridizing composition, which hybridizing does not consist of cooling. In some embodiments, bringing the surface bound nucleic acid into contact with the hybridizing composition comprising the target nucleic acid is performed under conditions of stringency that prevent the target nucleic acid from hybridizing to a non-complementary nucleic acid. In some embodiments, the stringency is at least or about 70%, 80%, or 90%. In some embodiments, the stringency is at least 80%.

Provided herein are compositions to hybridize a target nucleic acid molecule to a surface bound nucleic acid molecule, the composition comprising: (a) a target nucleic acid molecule; (b) at least one organic solvent; and (c) a pH buffer. In some embodiments, no more than 10% of a total number of the target nucleic acid molecule is associated with the surface without hybridizing to the surface bound nucleic acid molecule. In some embodiments, no more than 5% of the total number of the target nucleic acid molecule is bound to the surface without hybridizing to the surface bound nucleic acid molecule.

In some embodiments, the organic solvent is a polar aprotic solvent. In some embodiments, the organic solvent is an organic solvent having a dielectric constant of no greater than 40 when measured at 70 degrees Fahrenheit. In some embodiments, the organic solvent is acetonitrile, alcohol, or formamide. In some embodiments, the organic solvent comprises at least one functionality selected from hydroxy, nitrile, lactone, sulfone, sulfite, and carbonate. In some embodiments, the organic solvent is miscible with water. In some embodiments, the organic solvent is present in an amount effective to denature a double stranded nucleic acid. In some embodiments, an amount of the organic solvent is at least about 5% by volume based on the total volume of the composition. In some embodiments, an amount of the organic solvent is in the range of about 5% to 95% by volume based on the total volume of the composition. In some embodiments, the pH buffer system comprises a pH buffer. In some embodiments, an amount of the pH buffer is no greater than 90% by volume based on the total volume of the composition. In some embodiments, the composition further comprises a molecular crowding agent. In some embodiments, the molecular crowding agent is selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose, and any combination thereof. In some embodiments, the molecular crowding agent is polyethylene glycol (PEG). In some embodiments, the molecular crowding agent has a molecular weight in the range of about 5,000 to 40,000 Daltons. In some embodiments, an amount of the molecular crowding agent is at least about 5% by volume based on the total volume of the composition. In some embodiments, an amount of the molecular crowding agent is less than 50% by volume based on the total volume of the composition. In some embodiments, methods further comprise an additive for controlling a melting temperature of the target nucleic acid molecule. In some embodiments, an amount of the additive for controlling melting temperature of the target nucleic acid molecule is at least about 2% by volume based on the total volume of the composition. In some embodiments, an amount of the additive for controlling melting temperature of the nucleic acid molecule is in the range of about 2% to 50% by volume based on the total volume of the composition. In some embodiments, the pH buffer comprises at least one buffering agent selected from the group consisting of Tris, HEPES, TAPS, Tricine, Bicine, Bis-Tris, sodium hydroxide (NaOH), potassium hydroxide (KOH), TES, EPPS, and MOPS. In some embodiments, the pH buffer further comprises a second organic solvent. In some embodiments, the pH buffer comprises MOPS and methanol. In some embodiments, an amount of the pH buffer is effective to maintain the pH of the composition to be in the range of about 3 to about 10.

In some embodiments, the surface bound nucleic acid molecule is coupled to a surface through covalent or non-covalent bonding. In some embodiments, the surface is a hydrophilic polymer surface. In some embodiments, the polymer surface comprises one or more hydrophilic polymer layers, and wherein the surface bound nucleic acid molecule is coupled to the one or more hydrophilic polymer layers. In some embodiments, the one or more hydrophilic polymer layers comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, and dextran. In some embodiments, the one or more hydrophilic polymer layers comprises at least one dendrimer. In some embodiments, the target nucleic acid molecule is present in the composition at a 1 nanomolar concentration or less. In some embodiments, the target nucleic acid molecule is present in the composition at a 250 picomolar concentration or less. In some embodiments, the target nucleic acid molecule is present in the composition at a 100 picomolar concentration or less. In some embodiments, the target nucleic acid molecule is present in the composition at a 50 picomolar concentration or less.

In another aspect, the present disclosure provides a system for determining the identity of a nucleotide in a target nucleic acid, the system comprising: (a) a solid support having coupled thereto a primed target nucleic acid molecule; (b) a polymerase; and (c) a polymer-nucleotide conjugate, wherein the polymer-nucleotide conjugate comprises (i) a nucleotide and (ii) a detectable label. In some embodiments, the detectable label is a fluorescent label. In some embodiments, the polymer-nucleotide conjugate comprises two or more detectable labels. In some embodiments, the target nucleic acid is DNA. In some embodiments, the binding composition comprises one type of polymer-nucleotide conjugate. In some embodiments, the binding composition comprises two or more types of polymer-nucleotide conjugates. In some embodiments, each type of the two or more types of polymer-nucleotide conjugates comprises a different type of nucleotide. In some embodiments, the binding composition consists of three types of polymer-nucleotide conjugates and wherein each type of the three types of polymer-nucleotide conjugates comprises a different type of nucleotide. In some embodiments, the primed target nucleic acid has been replicated or amplified or has been produced by replication or amplification. In some embodiments, the polymer-nucleotide conjugate is contacted with the target nucleic acid and polymerase under conditions sufficient to form a binding complex.

Provided herein, in some embodiments, are microfluidic systems, comprising the composition described herein. In some embodiments, the microfluidic systems comprise a flow cell device. In some embodiments, the flow cell device is a microfluidic chip flow cell. In some embodiments, the flow cell device is a capillary flow cell device. In some embodiments, at least one surface of the flow cell device comprises one or more hydrophilic polymer layers comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, and dextran. In some embodiments, the flow cell device comprises a composition described herein formulated as a fluid. In some embodiments, the flow cell device comprises one or more surface bound nucleic acid molecules coupled to the at least one surface of the flow cell. In some embodiments, target nucleic acid molecule in the composition is hybridized to the one or more surface bound nucleic acid molecules coupled to the at least one surface of the flow cell. In some embodiments, the flow cell device is operatively coupled to an imaging system configured to capture an image of the at least one surface of the flow cell comprising the hybridized target nucleic acid molecule and the one or more surface bound nucleic acid molecules. Methods described herein comprise determining an identity of the target nucleic acid molecule using the microfluidic systems described herein.

Provided herein are kits comprising: (a) a surface; and (b) a composition comprising: (i) at least one organic solvent; and (ii) a pH buffer. In some embodiments, the surface comprises one or more surface bound nucleic acid molecules coupled to the surface. In some embodiments, the surface is a hydrophilic polymer surface. In some embodiments, the surface has a water contact angle of less than 45 degrees. In some embodiments, the hydrophilic polymer surface comprises one or more hydrophilic polymer layers, and wherein the surface bound nucleic acid is coupled to the one or more hydrophilic polymer layers. In some embodiments, the one or more hydrophilic polymer layers comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the kit further comprises instructions for hybridizing the one or more surface bound nucleic acid molecules to one or more target nucleic acid molecules. In some embodiments, the kit further comprises instructions for determining the identity of the one or more target nucleic acid molecules.

In some embodiments, the organic solvent is a polar aprotic solvent. In some embodiments, the organic solvent is an organic solvent having a dielectric constant of no greater than 40 when measured at 70 degrees Fahrenheit. In some embodiments, the organic solvent is acetonitrile, alcohol, or formamide. In some embodiments, the organic solvent comprises at least one functionality selected from hydroxy, nitrile, lactone, sulfone, sulfite, and carbonate. In some embodiments, the organic solvent is miscible with water. In some embodiments, the organic solvent is present in an amount effective to denature a double stranded nucleic acid. In some embodiments, an amount of the organic solvent is at least about 5% by volume based on the total volume of the composition. In some embodiments, an amount of the organic solvent is in the range of about 5% to 95% by volume based on the total volume of the composition. In some embodiments, the pH buffer system comprises a pH buffer. In some embodiments, an amount of the pH buffer is no greater than 90% by volume based on the total volume of the composition. In some embodiments, the composition further comprises a molecular crowding agent. In some embodiments, the molecular crowding agent is selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methycellulose, and hydroxyl methyl cellulose, and any combination thereof. In some embodiments, the molecular crowding agent is polyethylene glycol (PEG). In some embodiments, the molecular crowding agent has a molecular weight in the range of about 5,000 to 40,000 Daltons. In some embodiments, an amount of the molecular crowding agent is at least about 5% by volume based on the total volume of the composition. In some embodiments, an amount of the molecular crowding agent is less than 50% by volume based on the total volume of the composition. In some embodiments, methods further comprise an additive for controlling a melting temperature of the one or more target nucleic acid molecules. In some embodiments, an amount of the additive for controlling melting temperature of the one or more target nucleic molecules acid is at least about 2% by volume based on the total volume of the composition. In some embodiments, an amount of the additive for controlling melting temperature of the nucleic acid is in the range of about 2% to 50% by volume based on the total volume of the composition. In some embodiments, the pH buffer comprises at least one buffering agent selected from the group consisting of Tris, HEPES, TAPS, Tricine, Bicine, Bis-Tris, sodium hydroxide (NaOH), potassium hydroxide (KOH), TES, EPPS, and MOPS. In some embodiments, the pH buffer further comprises a second organic solvent. In some embodiments, the pH buffer comprises MOPS and methanol. In some embodiments, an amount of the pH buffer is effective to maintain the pH of the composition to be in the range of about 3 to about 10.

Provided herein are methods of using the kits described herein. In some embodiments, the surface bound nucleic acid molecules is coupled to the surface by a covalent or a noncovalent bond. In some embodiments, methods comprise: (a) combining the one or more target nucleic acid molecules and the composition of the kit to form a master mix; and (b) bringing the master mix into contact with the one or more surface bound nucleic acid molecules coupled to the surface provided in the kit. In some embodiments, methods further comprise (c) hybridizing the one or more target nucleic acid molecules with the one or more surface bound nucleic acid molecules coupled to the surface. In some embodiments, the surface exhibits a level of non-specific Cy3 dye absorption of less than about 0.25 molecules/$\mu m^2$. In some embodiments, no more than 10% of a total number of the one or more target nucleic acid molecules is associated with the surface without hybridizing to the surface bound nucleic acid molecule. In some embodiments, no more than 5% of the total number of the one or more target nucleic acid molecules is associated with the surface without hybridizing to the one or more surface bound nucleic acid molecules. In some embodiments, hybridizing the one or more target nucleic acid molecules with the one or more surface bound nucleic acid molecules coupled to the surface is performed under isothermal conditions. In some embodiments, the isothermal conditions are performed at a temperature in a range of 30 to 70 degrees Celsius. In some embodiments, methods further comprise (d) amplifying the target nucleic acid hybridized to the surface bound nucleic acid to form a plurality of clonally-amplified clusters of the one or more target nucleic acid molecules coupled to the surface; and (e) determining the identity of the one or more target nucleic acid molecules. In some embodiments, a fluorescence image of the surface comprising the plurality of clonally-amplified clusters of the one or more target nucleic acid molecules exhibits a contrast-to-noise ratio (CNR) of at least 20 when the fluorescence image is captured using a fluorescence imaging system under non-signal saturating conditions. In some embodiments, the CNR is at least 50.

In some embodiments, hybridizing the surface bound nucleic acid and the target nucleic acid is performed for a period of no more than 25 minutes. In some embodiments, methods further comprise removing the composition from the surface after the period of no more than 25 minutes. In some embodiments, hybridizing the surface bound nucleic acid and the target nucleic acid is performed for a period between 2-25 minutes. In some embodiments, hybridizing the one or more surface bound nucleic acid molecules and the one or more target nucleic acid molecules is performed for a period between 2-4 minutes. In some embodiments, hybridizing the one or more surface bound nucleic acid molecules and the one or more target nucleic acid molecules is performed for a period of 2 minutes. In some embodiments, the at least one surface bound nucleic acid is circular. In some embodiments, hybridizing does not consist of cooling. In some embodiments, bringing the master mix into contact with the one or more surface bound nucleic acid molecules is performed under conditions of stringency that prevent the one or more target nucleic acid molecules from hybridizing to a non-complementary nucleic acid. In some embodiments, the stringency is at least or about 70%, 80%, or 90%. In some embodiments, the stringency is at least 80%.

Provided herein are systems comprising: (a) a surface comprising one or more surface bound nucleic acids molecules coupled to the surface; (b) one or more target nucleic acid molecules; and (c) a composition comprising: (i) at least one organic solvent; and (ii) a pH buffer. In some embodiments, the systems further comprise a fluorescence imaging device. In some embodiments, the surface is a hydrophilic polymer surface. In some embodiments, the surface has a water contact angle of less than 45 degrees. In some embodiments, the hydrophilic polymer surface comprises one or more hydrophilic polymer layers, and wherein the one or more surface bound nucleic acid molecules is coupled to the one or more hydrophilic polymer layers. In some embodiments, the one or more hydrophilic polymer layers comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, and dextran.

In some embodiments, the organic solvent is an organic solvent having a dielectric constant of no greater than 40 when measured at 70 degrees Fahrenheit. In some embodiments, the organic solvent is acetonitrile, alcohol, or formamide. In some embodiments, the organic solvent comprises at least one functionality selected from hydroxy, nitrile, lactone, sulfone, sulfite, and carbonate. In some embodiments, the organic solvent is miscible with water. In some embodiments, the organic solvent is present in an amount effective to denature a double stranded nucleic acid. In some embodiments, an amount of the organic solvent is at least about 5% by volume based on the total volume of the composition. In some embodiments, an amount of the organic solvent is in the range of about 5% to 95% by volume based on the total volume of the composition. In some embodiments, the pH buffer system comprises a pH buffer. In some embodiments, an amount of the pH buffer is no greater than 90% by volume based on the total volume of the composition. In some embodiments, the composition further comprises a molecular crowding agent. In some embodiments, the molecular crowding agent is selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methyl cellulose, and hydroxyl methyl cellulose, and any combination thereof. In some embodiments, the molecular crowding agent is polyethylene glycol (PEG). In some embodiments, the molecular crowding agent has a molecular weight in the range of about 5,000 to 40,000 Daltons. In some embodiments, an amount of the molecular crowding agent is at least about 5% by volume based on the total volume of the composition. In some embodiments, an amount of the molecular crowding agent is less than 50% by volume based on the total volume of the composition. In some embodiments, methods further comprise an additive for controlling a melting temperature of the target nucleic acid. In some embodiments, an amount of the additive for controlling melting temperature of the one or more target nucleic acid molecules is at least about 2% by volume based on the total volume of the composition. In some embodiments, an amount of the additive for controlling melting temperature of the one or more nucleic acid molecules is in the range of about 2% to 50% by volume based on the total volume of the composition. In some embodiments, the pH buffer comprises at least one buffering agent selected from the group consisting of Tris, HEPES, TAPS, Tricine, Bicine, Bis-Tris, sodium hydroxide (NaOH), potassium hydroxide (KOH), TES, EPPS, and MOPS. In some embodiments, the pH buffer further comprises a second organic solvent. In some embodiments, the pH buffer comprises MOPS and methanol. In some embodiments, an amount of the pH buffer is effective to maintain the pH of the composition to be in the range of about 3 to about 10.

Provided herein are methods of using the systems described herein. In some embodiments, the one or more surface bound nucleic acid molecules is coupled to the surface by a covalent or a noncovalent bond. In some embodiments, methods comprise: (a) combining the one or more target nucleic acid molecules and the composition of the system to form a master mix; (b) bringing the master mix into contact with the one or more surface bound nucleic acid molecules coupled to the surface provided in the system; (c) hybridizing the one or more target nucleic acid molecules with the one or more surface bound nucleic acid molecules coupled to the surface; (d) amplifying the one or more target nucleic acid molecules hybridized to the one or more surface bound nucleic acid molecules to form a plurality of clonally-amplified clusters of the one or more target nucleic acid molecules coupled to the surface; and (e) determining the identity of the one or more target nucleic acid molecules by capturing an image of the surface with the fluorescence imaging device. In some embodiments, the surface exhibits a level of non-specific Cy3 dye absorption of less than about 0.25 molecules/$m^2$. In some embodiments, hybridizing the one or more target nucleic acid molecules with the one or more surface bound nucleic acid molecules coupled to the surface is performed under isothermal conditions. In some embodiments, the isothermal conditions are performed at a temperature in a range of 30 to 70 degrees Celsius. In some embodiments, no more than 10% of a total number of the one or more target nucleic acid molecules is associated with the surface without hybridizing to the one or more surface bound nucleic acid molecules. In some embodiments, no more than 5% of the total number of the one or more target nucleic acid molecules is associated with the surface without hybridizing to the one or more surface bound nucleic acid molecules. In some embodiments, a fluorescence image of the surface comprising the amplified one or more target nucleic acid molecules exhibits a contrast-to-noise ratio (CNR) of at least 20 when the fluorescence image is captured using the fluorescence imaging device under non-signal saturating conditions. In some embodiments, the CNR is at least 50.

In some embodiments, hybridizing the one or more surface bound nucleic acid molecules and the one or more target nucleic acid molecules is performed for a period of no more than 25 minutes. In some embodiments, methods further comprise removing the composition from the surface after the period of no more than 25 minutes. In some embodiments, hybridizing the one or more surface bound nucleic acid molecules and the one or more target nucleic acid molecules is performed for a period between 2-25 minutes. In some embodiments, hybridizing the one or more surface bound nucleic acid molecules and the one or more target nucleic acid molecules is performed for a period between 2-4 minutes. In some embodiments, hybridizing the one or more surface bound nucleic acid molecules and the one or more target nucleic acid molecules is performed for a period of 2 minutes. In some embodiments, the at least one surface bound nucleic acid is circular. In some embodiments, hybridizing does not consist of cooling. In some embodiments, bringing the one or more surface bound nucleic acid molecules into contact with the hybridizing composition comprising the one or more target nucleic acid molecules is performed under conditions of stringency that prevent the one or more target nucleic acid molecules from hybridizing to a non-complementary nucleic acid molecule.

In some embodiments, the stringency is at least or about 70%, 80%, or 90%. In some embodiments, the stringency is at least 80%.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A illustrates a non-limiting example 4—of attaching target nucleic acid to a surface; FIG. 1B illustrates clonally the target nucleic acid to form clusters of amplified target nucleic acid molecules; FIG. 1C illustrates a non-limiting example of priming the target nucleic acid to produce a primed target nucleic acid; FIG. 1D illustrates a non-limiting example of contacting the primed target nucleic acid to the multivalent binding composition and polymerase to form a binding complex; FIG. 1E illustrates a non-limiting example of the images of the binding complex captured on the surface; FIG. 1F illustrates a non-limiting example of extending the primer strand by one nucleotide; FIG. 1G illustrates a non-limiting example of another cycle of contacting the primed target nucleic acid to the multivalent binding composition and polymerase to form a binding complex; and FIG. 1H illustrates non-limiting examples of the images of binding complex captured on the surface in subsequent sequencing cycles.

FIG. 2A shows the step of contacting the polymerase and polymer-nucleotide conjugates to some nucleic acid molecules; FIG. 2B shows the binding complex formed between the polymerase, polymer-nucleotide conjugates, and the target nucleic acid molecules.

FIGS. 3A-3B provide non-limiting examples of image data that demonstrate the improvements in hybridization stringency, speed, and efficacy that may be achieved through the reformulation of the hybridization buffer used for solid-phase nucleic acid amplification, as described herein. FIG. 3A provides examples of image data for two different hybridization buffer formulations and protocols.

FIG. 3B provides an example of the corresponding image data obtained using a standard hybridization buffer and protocol.

FIG. 4 illustrates a workflow for nucleic acid sequencing using the disclosed hybridization methods on low binding surfaces, and non-limiting examples of the processing times that may be achieved.

DETAILED DESCRIPTION

I. Definitions

Figure 1A:
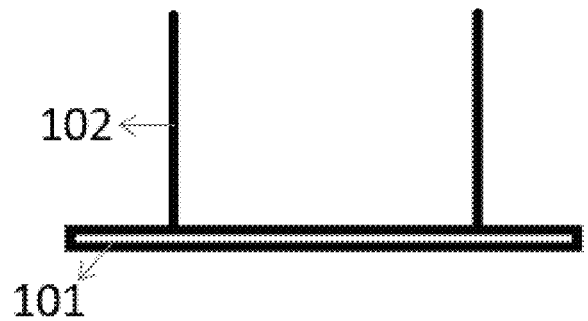
FIGS. 1A-1H illustrate the steps utilizing a non-limiting examples of multivalent binding composition for sequencing a target nucleic acid.

As used herein, "nucleic acid" (also referred to as a "polynucleotide", "oligonucleotide", ribonucleic acid (RNA), or deoxyribonucleic acid (DNA)) is a linear polymer of two or more nucleotides joined by covalent internucleosidic linkages, or variants or functional fragments thereof. In naturally occurring examples of nucleic acids, the internucleoside linkage is typically a phosphodiester bond. However, other examples optionally comprise other internucleoside linkages, such as phosphorothiolate linkages and may or may not comprise a phosphate group. Nucleic acids include double- and single-stranded DNA, as well as double- and single-stranded RNA, DNA/RNA hybrids, peptide-nucleic acids (PNAs), hybrids between PNAs and DNA or RNA, and may also include other types of nucleic acid modifications.

As used herein, a "nucleotide" refers to a nucleotide, nucleoside, or analog thereof. The nucleotide refers to both naturally occurring and chemically modified nucleotides and can include but are not limited to a nucleoside, a ribonucleotide, a deoxyribonucleotide, a protein-nucleic acid residue, or derivatives. Examples of the nucleotide includes an adenine, a thymine, a uracil, a cytosine, a guanine, or residue thereof, a deoxyadenine, a deoxythymine, a deoxyuracil, a deoxycytosine, a deoxyguanine, or residue thereof, a adenine PNA, a thymine PNA, a uracil PNA, a cytosine PNA, a guanine PNA, or residue or equivalents thereof, an N- or C-glycoside of a purine or pyrimidine base (e.g., a deoxyribonucleoside containing 2-deoxy-D-ribose or ribonucleoside containing D-ribose).

"Complementary," as used herein, refers to the topological compatibility or matching together of interacting surfaces of a ligand molecule and its receptor. Thus, the receptor and its ligand can be described as complementary, and furthermore, the contact surface characteristics are complementary to each other.

"Branched polymer", as used herein, refers to a polymer having a plurality of functional groups that help conjugate a biologically active molecule such as a nucleotide, and the functional group can be either on the side chain of the polymer or directly attaches to a central core or central backbone of the polymer. The branched polymer can have linear backbone with one or more functional groups coming off the backbone for conjugation. The branched polymer can also be a polymer having one or more sidechains, wherein the side chain has a site suitable for conjugation. Examples of the functional group include but are limited to hydroxyl, ester, amine, carbonate, acetal, aldehyde, aldehyde hydrate, alkenyl, acrylate, methacrylate, acrylamide, active sulfone, hydrazide, thiol, alkanoic acid, acid halide, isocyanate, isothiocyanate, maleimide, vinylsulfone, dithiopyridine, vinylpyridine, iodoacetamide, epoxide, glyoxal, dione, mesylate, tosylate, and tresylate.

"Polymerase," as used herein, refers to an enzyme that contains a nucleotide binding moiety and helps formation of a binding complex between a target nucleic acid and a complementary nucleotide. The polymerase can have one or more activities including, but not limited to, base analog detection activities, DNA polymerization activity, reverse transcriptase activity, DNA binding, strand displacement activity, and nucleotide binding and recognition. The polymerase can include catalytically inactive polymerase, catalytically active polymerase, reverse transcriptase, and other enzymes containing a nucleotide binding moiety.

"Persistence time," as used herein, refers to the length of time that a binding complex, which is formed between the target nucleic acid, a polymerase, a conjugated or unconjugated nucleotide, remains stable without any binding component dissociates from the binding complex. The persistence time is indicative of the stability of the binding complex and strength of the binding interactions. Persistence time can be measured by observing the onset and/or duration of a binding complex, such as by observing a signal from a labeled component of the binding complex. For example, a labeled nucleotide or a labeled reagent comprising one or more nucleotides may be present in a binding complex, thus allowing the signal from the label to be detected during the persistence time of the binding complex. One exemplary label is a fluorescent label.

As used in this specification and the appended claims, the singular forms "a", "an", and "the" include plural references unless the context clearly dictates otherwise. Any reference to "or" herein is intended to encompass "and/or" unless otherwise stated.

As used herein, the term "about" a number refers to that number plus or minus 10% of that number. The term 'about' when used in the context of a range refers to that range minus 10% of its lowest value and plus 10% of its greatest value.

As used herein, the terms "DNA hybridization" and "nucleic acid hybridization" are used interchangeably, and are intended to cover any type of nucleic acid hybridization, e.g., DNA hybridization, RNA hybridization, unless otherwise specified.

As used herein, the term "isothermal" refers to a condition in which the temperature remains substantially constant. A temperature that is "substantially constant" may deviate (e.g., increase or decrease) over a period of time by no more than 0.25 degrees, 0.50 degrees, 0.75 degrees, or 1.0 degrees.

The terms "anneal" or "hybridize," are used herein interchangeably to refer to the ability of two nucleic acid molecules to combine together. In some cases, the "combining" refers to Watson-Crick base pairing between the bases in each of the two nucleic acid molecules.

As used herein, "hybridization specificity" refers to a measure of the ability of nucleic acid molecules (e.g., adapter sequences, primer sequences, or oligonucleotide sequences) to correctly hybridize to a region of a target nucleic acid molecule with a nucleic acid sequence that is completely complementary to the nucleic acid molecule.

As used herein, "hybridization sensitivity" refers to a concentration range of sample (or target) nucleic molecules in which hybridization occurs with high specificity. In some cases, as little as 50 picomolar concentration of sample nucleic acid molecules in which hybridization with high specify is achieved with the methods, compositions, systems and kits described herein. In some cases, the range is between about 1 nanomolar to about 50 picomolar concentrations of sample nucleic acid molecules.

As used herein, "hybridization efficiency" refers to a measure of the percentage of total available nucleic acid molecules (e.g., adapter sequences, primer sequences, or oligonucleotide sequences) that are hybridized to the region of the target nucleic acid molecule with the nucleic acid sequence that is completely complementary to the nucleic acid molecule.

As used herein, the term "hybridization stringency" refer to a percentage of nucleotide bases within at least a portion of a nucleic acid sequence undergoing a hybridization (e.g., a hybridization region) reaction that is complementary through standard Watson-Crick base pairing. In a non-limiting example, a hybridization stringency of 80% means that a stable duplex can be formed in which 80% of the hybridization region undergoes Watson-Crick base pairing. A higher hybridization stringency means a higher degree of Watson-Crick base pairing is required in a given hybridization reaction in order to form a stable duplex.

As used herein, the terms, "isolate" and "purify," are used interchangeably herein unless specified otherwise.

Abbreviations

Dimethyl sulfoxide (DMSO),
Dimethyl formamide (DMF),
3-(N-morpholino)propanesulfonic acid (MOPS),
Acetonitrile (ACN)
2-(N-morpholino)ethanesulfonic acid (MES)
saline-sodium citrate (SSC)
Formamide (Form.)
Tris(hydroxymethyl)aminomethane (Tris)

Method of Analyzing Target Nucleic Acid

Disclosed herein are multivalent binding compositions and their use in analyzing nucleic acid including sequencing or other bioassay applications. An increase in binding of a nucleotide to an enzyme (e.g., polymerase) or an enzyme complex can be effected by increasing the effective concentration of the nucleotide. The increase can be achieved by increasing the concentration of the nucleotide in free solution, or by increasing the amount of the nucleotide in proximity to the relevant binding site. The increase can also be achieved by physically restricting a number of nucleotides into a limited volume thus resulting in a local increase in concentration, and such as structure may thus bind to the binding site with a higher apparent avidity than would be observed with unconjugated, untethered, or otherwise unrestricted individual nucleotide. One exemplary means of effecting such restriction is by providing a multivalent binding composition in which multiple nucleotides are bound to a particle such as a polymer, a branched polymer, a dendrimer, a micelle, a liposome, a microparticle, a nanoparticle, a quantum dot, or other suitable particle known in the art.

The multivalent binding composition disclosed herein can include at least one particle-nucleotide conjugate, and the particle-nucleotide conjugate has a plurality of copies of the same nucleotide attached to the particle. When the nucleotide is complementary to the target nucleic acid, the particle-nucleotide conjugate forms a binding complex with the polymerase and the target nucleic acid, and the binding complex exhibits increased stability and longer persistence time than the binding complex formed using a single unconjugated or untethered nucleotide.

The multivalent binding composition can be used to localize detectable signals to active regions of biochemical interactions, such as sites of protein-nucleic acid interactions, nucleic acid hybridization reactions, or enzymatic reactions, such as polymerase reactions. For instance, the multivalent binding composition described herein can be utilized to identify sites of base incorporation in elongating nucleic acid chains during polymerase reactions and to provide base discrimination for sequencing and array based applications. The increased binding between the target nucleic acid and the nucleotide in the multivalent binding composition, when the nucleotide is complementary to the target nucleic acid, provides enhanced signal that greatly improve base call accuracy and shorten imaging time.

In addition, the use of multivalent binding composition allows sequencing signals from a given sequence to originate within cluster regions containing multiple copies of the target sequence. Sequencing methods incorporating multiple copies of a target sequence have the advantage that signals can be amplified due to the presence of multiple simultaneous sequencing reactions within the defined region, each providing its own signal. The presence of multiple signals within a defined area also reduces the impact of any single skipped cycle, due to the fact that the signal from a large number of correct base calls can overwhelm the signal from a smaller number of skipped or incorrect base calls, therefore providing methods for reducing phasing errors and/or to improve read length in sequencing reactions.

The multivalent binding compositions and their use disclosed herein lead to one or more of: (i) stronger signal for better base-calling accuracy compared to conventional nucleic acid amplification and sequencing methodologies; ii) allow greater discrimination of sequence-specific signal from background signals; (iii) reduced requirements for the amount of starting material necessary, (iv) increased sequencing rate and shortened sequencing time; (v) reducing phasing errors, and (vi) improving read length in sequencing reactions.

In some embodiments, the target nucleic acid can refer to a target nucleic acid sample having one or more nucleic acid molecules. In some embodiments, the target nucleic acid can include a plurality of nucleic acid molecules. In some embodiments, the target nucleic acid can include two or more nucleic acid molecules. In some embodiments, the target nucleic acid can include two or more nucleic acid molecules having the same sequences.

Sequencing Target Nucleic Acid

FIG. 1A-1H illustrate one exemplified method in which the multivalent binding composition is used for sequencing a target nuclei acid. As shown in FIG. 1A, the target nucleic acid 102 can be tethered to a solid support surface 101. The target nucleic acid can be attached to the surface either directly or indirectly. Although not shown in FIG. 1A, the target nucleic acid 102 can be hybridized to an adapter, which is attached to the surface through a covalent or noncovalent bond. When one or more adapters are used to attach the target nucleic acid to the surface, the target surface can comprise a fragment that is complementary to the adapter and thus hybridize to the adaptor. In some instances, one adapter sequence may be tethered to the surface. In some instances, a plurality of adapter sequences may be tethered to the surface. In some instances, the target nucleic acid 102 can also be attached directly to the solid-support surface without the use of an adapter. The solid support can be a low non-specific binding surface.

Figure 1B:
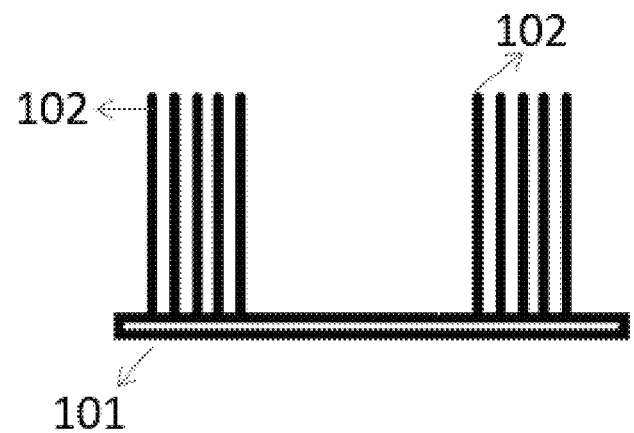

In FIG. 1B, after the initial step of attaching the target nucleic acid to the surface of a solid support surface (e.g., through hybridization to adapters), the target nucleic acid is then clonally-amplified to form clusters of amplified nucleic acids. When the target nucleic acid is attached to the surface through an adapter, the surface density of clonally-amplified nucleic acid sequences hybridized to adapter on the support surface may span the same range as the surface density of tethered primers. The clonal amplification may be performed using a polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, single-stranded binding (SSB) protein-dependent amplification, or any combination thereof.

Figure 1C:
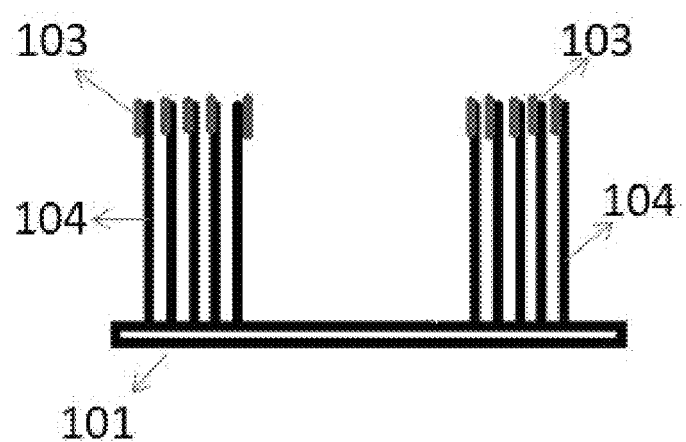

FIG. 1C illustrates a non-limiting step of annealing a primer 103 to the target nucleic acid 102 to form a primed target nucleic acid 104. FIG. 1B only shows one primer being used in the annealing step, but more than one primers can be used depending on the types of target nucleic acid. In some instances, the adapter that is used to attach the target nucleic acid to the surface has the same sequence as the primer used to prepare the primed target nucleic acid. The primer may comprise forward amplification primers, reverse amplification primers, sequencing primers, and/or molecular barcoding sequences, or any combination thereof. In some instances, one primer sequence may be used in the hybridization step. In some instances, a plurality of different primer sequences may be used in the hybridization step.

Figure 1D:
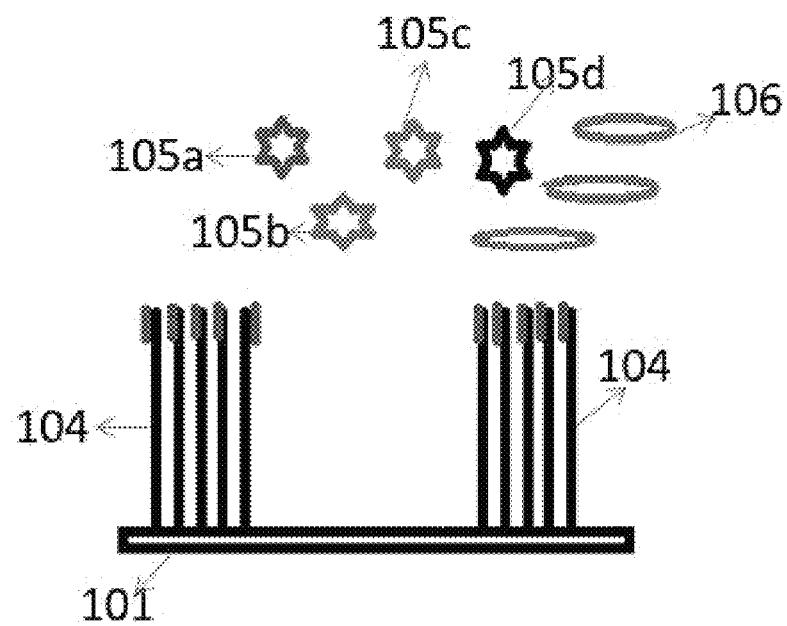

As shown in FIG. 1D, the primed target nucleic acid 104 is combined with a multivalent binding composition and a polymerase 106 to form a binding complex. The non-limiting example of multivalent binding composition in FIG. 1D comprises four particle-nucleotide conjugates 105a, 105b, 105c, and 105d. Each particle-nucleotide conjugate has multiple copies of a nucleotide attached to the particle, and the four particle-nucleotide conjugates cover four types of nucleotide respectively. The particle-nucleotide conjugate having a nucleotide that is complementary to the next base on the target nucleic acid will form a binding complex with the polymerase and the target nucleic acid. In some instances, the multivalent binding composition may include one, two or three particle-nucleotide conjugates. In some embodiments, each different type of particle-nucleotide conjugate can be labeled with a separate label. In some embodiments, three of four types of nucleotide conjugates can be labeled, with a fourth either unlabeled or conjugated to an undetectable label. In some embodiments, 1, 2, 3, or 4 particle-nucleotide conjugates can be labeled, either with the same label, or each with a label corresponding to the identity of its conjugated nucleotide, with, respectively, 3, 2, 1, or no particle-nucleotide conjugates that may be either left unlabeled or conjugated to an undetectable label. In some embodiments, detection of a polymerase complex incorporating a particle-nucleotide conjugate may be carried out using four-color detection, such that conjugates corresponding to all four nucleotides are present in a sample, each conjugate having a separate label corresponding to the nucleotide conjugated thereto. In some embodiments, the four particle-nucleotide conjugates may be exposed to or contacted with the target nucleic acid at the same time; in some other embodiments, the four particle-nucleotide conjugates may be exposed to or contacted with the target nucleic acid sequentially, either individually, or in groups of two or three. In some embodiments, detection of a polymerase complex incorporating a particle-nucleotide conjugate may be carried out using three-color detection, such that conjugates corresponding to three of the four nucleotides are present in a sample, with three conjugates having a separate label corresponding to the nucleotide conjugated thereto and one conjugate having no label or being conjugated to an undetectable label. In some embodiments, only three types of conjugates are provided, such that conjugates corresponding to three of the four nucleotides are present in a sample, with three conjugates having a separate label corresponding to the nucleotide conjugated thereto and one conjugate being absent. In some embodiments, the identity of nucleotides corresponding to an unlabeled or absent nucleotide conjugate can be determined with respect to the location and/or identity of "dark" spots or locations of known target nucleic acids showing no fluorescence signal. In some embodiments, the present disclosure provides said method, wherein the detection of the binding complex is performed in the absence of unbound or solution-borne polymer nucleotide conjugates.

In some embodiments where three of the four particle-nucleotide conjugates are labeled, or where only three of the four particle-nucleotide conjugates are present, the identity of the nucleotide corresponding to the unlabeled or absent conjugate may be established by the absence of a signal or by monitoring of the presence of unlabeled complexes such as by the identification of "dark" spots or unlabeled regions in a sequencing reaction. In some embodiments, detection of a polymerase complex incorporating a particle-nucleotide conjugate may be carried out using two-color detection, such that conjugates corresponding to two of the four nucleotides are present in a sample, with two conjugates having a separate label corresponding to the nucleotide conjugated thereto and two conjugates having no label or being conjugated to an undetectable label. In some embodiments, only two of the four particle-nucleotide conjugates are labeled. In some embodiments where two of the four particle-nucleotide conjugates are labeled, the identity of the nucleotide corresponding to the unlabeled conjugate or conjugates may be established by the absence of a signal or by monitoring of the presence of unlabeled complexes such as by the identification of "dark" spots or unlabeled regions in a sequencing reaction. In some embodiments where two of the four particle-nucleotide conjugates are labeled, the four particle-nucleotide conjugates may be exposed to or contacted with the target nucleic acid sequentially, either individually, or in groups of two or three. In some embodiments two of the four particle-nucleotide conjugates may share a common label, and the four particle-nucleotide conjugates may be exposed to or contacted with the target nucleic acid sequentially, either individually, or in groups of two or three, wherein each contacting step shows the distinction between two or more different bases, such that after two, three, four, or more such contacting steps the identities of all unknown bases have been determined.

Figure 1E:
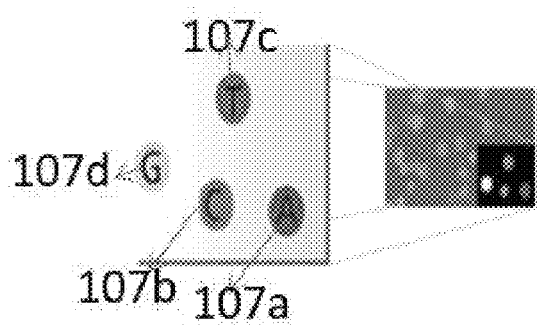

FIG. 1E shows the images captured on the surface after the binding complex is formed between the polymerase, the target nucleic acid, and the particle-nucleotide conjugate having a nucleotide commentary to the next base of the target nucleic acid. The captured image includes four binding complexes 107a, 107b, 107c, and 107d formed on the surface, and each binding complex has a different nucleotide which can be distinguished based on the label (e.g., color) on the particle-nucleotide conjugate. Because of use of the particle-nucleotide conjugate allows binding signals from a given sequence to originate within cluster regions containing multiple copies of the target sequence, the sequencing signals is greatly enhanced. Although FIG. 1E involves four particle-nucleotide conjugate, each having a different type of nucleotide, some methods can use one, two, or three particle-nucleotide conjugates, each having a different type of nucleotide and label. In some embodiments, each different type of particle-nucleotide conjugate can be labeled either with the same label, or each with a label corresponding to the identity of its conjugated nucleotide. In some embodiments, three of four types of nucleotide conjugates can be labeled, with a fourth either unlabeled or conjugated to an undetectable label. In some embodiments, 1, 2, 3, or 4 particle-nucleotide conjugates can be labeled with a separate label, with, respectively, 3, 2, 1, or no particle-nucleotide conjugates either unlabeled or conjugated to an undetectable label In some embodiments, a detection step can comprise simultaneous and/or serial excitation of up to 4 different excitation wavelengths, such as wherein the fluorescence imaging is carried out by detecting single and/or multiple fluorescence emission bands that uniquely classify each of the possible base pairing (A, G, C, or T). In some embodiments, four different nucleic acid binding compositions, each comprising a different nucleotide or nucleotide analog, may be used to determine the identity of the terminal nucleotide, wherein one of the four different nucleic acid binding compositions is labeled with a first fluorophore, one is labeled with a second fluorophore, one is labeled with both the first and second fluorophore, and one is not labeled, and wherein the detecting step comprises simultaneous excitation at a first excitation wavelength and a second excitation wavelength and images are acquired at a first fluorescence emission wavelength and a second fluorescence emission wavelength.

When the multivalent binding composition is used in replacement of single unconjugated or untethered nucleotide to form a binding complex with the polymerase and the target nucleic acid, the local concentration of the nucleotide is increased many fold, which in turn enhances the signal intensity. The formed binding complex also has a longer persistence time which in turn helps shorten the imaging step. The high signal intensity resulted from the use of the polymer nucleotide conjugate remain for the entire binding and imaging step. The strong binding between the polymerase, the primed target strand, and the nucleotide or nucleotide analog also means that the formed binding complex will remain stable during the washing step and the signal will remain at a high intensity when other reaction mixture and unmatched nucleotide analogs are washed away. After the imaging step, the binding complex can be destabilized and the primed target nucleic acid can then be extended for one base.

Figure 1F:
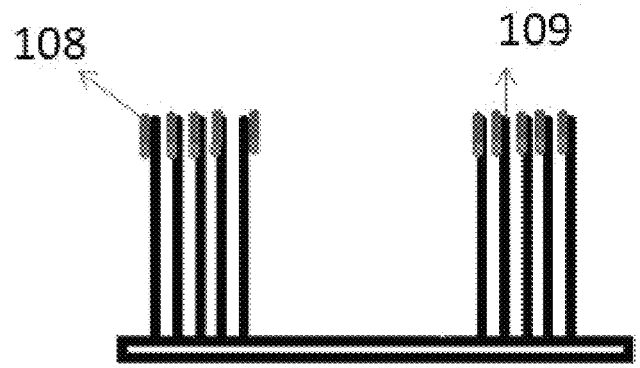
Figure 1G:
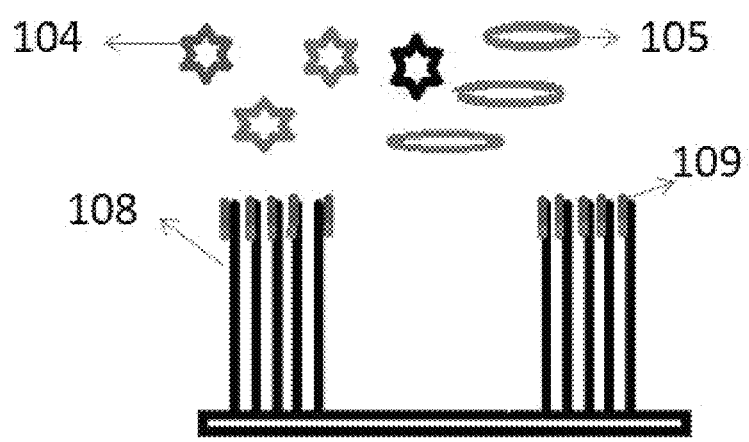

The sequencing method may further comprise incorporating the N+1 or terminal nucleotide into the primed strand as shown in FIG. 1F. In FIG. 1F, the primer strand of the primed target nucleic acid 104 can be extended for one base to form an extended nucleic acid 108. The extension step can occur after or concurrently with the destabilization of the binding complex. The primed target nucleic acid 104 can be extended using a complementary nucleotide that is attached to the particle in the particle-nucleotide conjugate, or using an unconjugated or untethered free nucleotide that is provided after the multivalent binding composition has been removed.

Figure 1H:
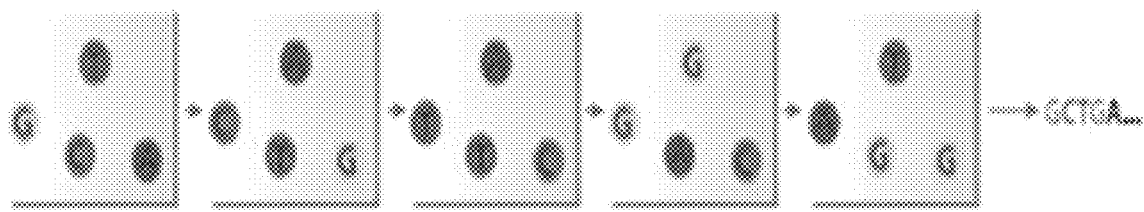

After the extension step, the contacting step as shown in FIG. 1G can be performed again to form binding complexes and imitate the next sequencing cycle. The contacting, detecting, and extension steps can be repeated for one or more cycles, thereby determining the sequence of the target nucleic acid molecule. For example, FIG. 1H shows the surface images after multiple sequencing cycles, and the images can then be processed to determine the sequences of the target nucleic acid molecules.

The extension of the primed target nucleic acid may be prevented or inhibited due to a blocked nucleotide on the strand or the use of polymerase that is catalytically inactive. When the nucleotide in the polymer-nucleotide conjugate has a blocking group that prevents the extension of the nucleic acid, incorporation of a nucleotide may be achieved by the removal of a blocking group from said nucleotide (such as by detachment of said nucleotide from its polymer, branched polymer, dendrimer, particle, or the like). When the extension of the primed target nucleic acid is inhibited due to the use of polymerase that is catalytically inactive, incorporation of a nucleotide may be achieved by the provision of a cofactor or activator such as a metal ion.

Also disclosed herein are systems configured for performing any of the disclosed nucleic acid sequencing or nucleic acid analysis methods. The system may comprise a fluid flow controller and/or fluid dispensing system configured to sequentially and iteratively contact the primed target nucleic acid molecules attached to a solid support with the disclosed polymerase and multivalent binding compositions and/or reagents. The contacting may be performed within one or more flow cells. In some instances, said flow cells may be fixed components of the system. In some instances, said flow cells may be removable and/or disposable components of the system.

The sequencing system may include an imaging module, i.e., one or more light sources, one or more optical components, and one or more image sensors for imaging and detection of binding of the disclosed nucleic acid binding compositions to target nucleic acid molecules tethered to a solid support or the interior of a flow cell. The disclosed compositions, reagents, and methods may be used for any of a variety of nucleic acid sequencing and analysis applications. Examples include, but are not limited to, DNA sequencing, RNA sequencing, whole genome sequencing, targeted sequencing, exome sequencing, genotyping, and the like.

The sequencing system may also include computer control systems that are programmed to implement methods of the disclosure. The computer system is programmed or otherwise configured to implement methods of the disclosure including nucleic acid sequencing methods, interpretation of nucleic acid sequencing data and analysis of cellular nucleic acids, such as RNA (e.g., mRNA), and characterization of cells from sequencing data. The computer system can be an electronic device of a user or a computer system that is remotely located with respect to the electronic device. The electronic device can be a mobile electronic device.

Methods and systems of the present disclosure may comprise attaching target library sequences to a solid support surface by hybridizing the target nucleic acid molecules to complementary adapters on substrate surface. The target nucleic acid molecules can be single stranded or partially double stranded. The nucleic acid molecules in the target library may have been prepared to contain fragments complementary to the adaptor sequences through ligation or other methods. Clonal amplification may be used to generate clusters of target nucleic acid molecules on the surface. Hybridizing sequencing primers to complementary primer binding sequences on the target nucleic acid may be performed to form the primed target nucleic acid. A binding complex may be formed comprising the polymerase, the multivalent binding composition, which in some embodiments, contains labeled (e.g., fluorescently-labeled) particle-nucleotide conjugates, and the primed target nucleic acid. Methods and systems may also comprise washing or removing the unbound reagents including polymerase and particle-nucleotide conjugate.

Figure 2A:
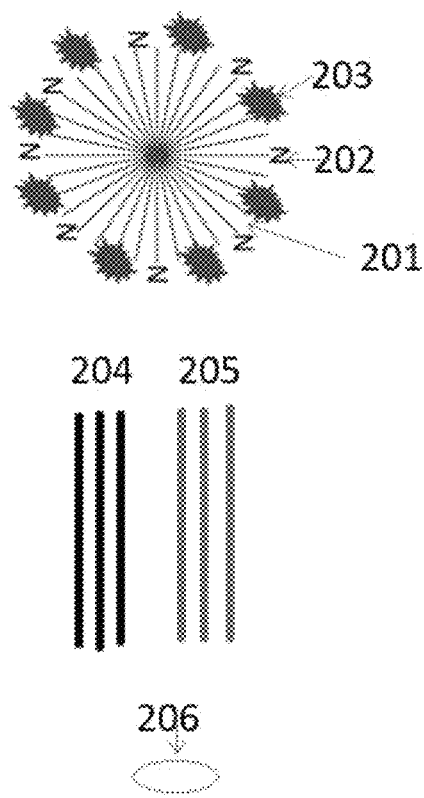
FIG. 2A-2B illustrate a non-limiting example of detecting target nucleic acid using the polymer-nucleotide conjugates.
Figure 2B:
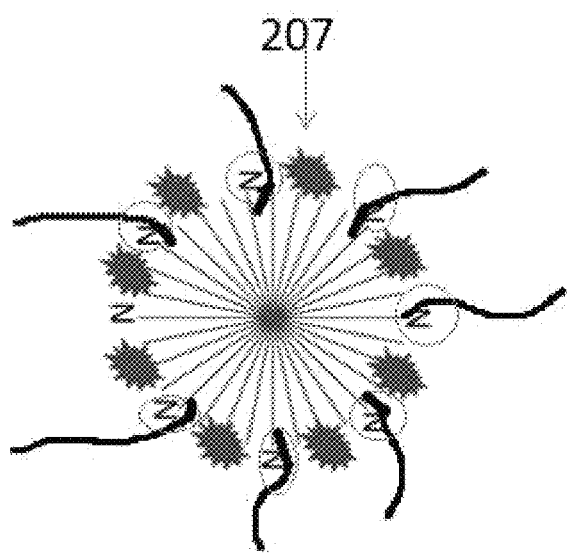

When the nucleotide on the particle-nucleotide conjugate is complementary to the next base of the primed target nucleic acid, the particle-nucleotide conjugate, polymerase, and primed target nucleic acid form a binding complex, which can be detected by detection methods (e.g., florescence imaging) compatible with the label on the particle-nucleotide conjugate. The persistence time of the binding complex may be measured at this point in the workflow. The binding complex may be destabilized to remove the binding of the particle-nucleotide conjugate and polymerase. The dissociation can be achieved by placing the binding complex in a condition (e.g., adding Strontium ions) that will change the conformation of the polymerase and destabilize the binding. The dissociated particle-nucleotide conjugate and/or polymerase may be removed or washed away. Next, the method or system comprises extending the primed strand of the primed target nucleic acid by a single base addition reaction. After the single base extension, the above steps can be repeated in multiple cycles to determine the sequences of the target nucleic acid. FIG. 2A-2B illustrate a non-limiting example of detecting target nucleic acid using the polymer-nucleotide conjugates. FIG. 2A shows the step of contacting the polymerase and polymer-nucleotide conjugates to some nucleic acid molecules. FIG. 2B shows the binding complex formed between the polymerase, polymer-nucleotide conjugates, and the target nucleic acid molecules.

Multivalent Binding Composition

The present disclosure relates to multivalent binding compositions having a plurality of nucleotides conjugated to a particle (e.g., a polymer, branched polymer, dendrimer, or equivalent structure). Contacting the multivalent binding composition with a polymerase and a primed target nucleic acid may result in the formation of a ternary complex which may be detected and in turn achieve a more accurate determination of the bases of the target nucleic acid.

When the multivalent binding composition is used in replacement of single unconjugated or untethered nucleotide to form a complex with the polymerase and the target nucleic acid, the local concentration of the nucleotide is increased many fold, which in turn enhances the signal intensity, particularly the correct signal versus mismatch. The multivalent binding composition described herein can include at least one particle-nucleotide conjugate for interacting with the target nucleic acid. The multivalent composition can also include two, three, or four different particle-nucleotide conjugates, each having a different nucleotide conjugated to the particle.

The multivalent binding composition can comprise 1, 2, 3, 4, or more types of particle-nucleotide conjugates, wherein each particle-nucleotide conjugate comprises a different type of nucleotide. A first type of the particle-nucleotide conjugate can comprise a nucleotide selected from the group consisting of ATP, ADP, AMP, dATP, dADP, and dAMP. A second type of the particle-nucleotide conjugate can comprise a nucleotide selected from the group consisting of TTP, TDP, TMP, dTTP, dTDP, dTMP, UTP, UDP, UMP, dUTP, dUDP, and dUMP. A third type of the particle-nucleotide conjugate can comprise a nucleotide selected from the group consisting of CTP, CDP, CMP, dCTP, dCDP, and dCMP. A fourth type of the particle-nucleotide conjugate can comprise a nucleotide selected from the group consisting of GTP, GDP, GMP, dGTP, dGDP, and dGMP. In some embodiments, each particle-nucleotide conjugate comprises a single type of nucleotide respectively corresponding to one or more nucleotide selected from the group consisting of ATP, ADP, AMP, dATP, dADP, dAMP TTP, TDP, TMP, dTTP, dTDP, dTMP, UTP, UDP, UMP, dUTP, dUDP, dUMP, CTP, CDP, CMP, dCTP, dCDP, dCMP, GTP, GDP, GMP, dGTP, dGDP, and dGMP. Each multivalent binding composition may further comprise one or more labels corresponding to the particular nucleotide conjugated to each respective conjugate. Exemplary labels include fluorescent labels, colorimetric labels, electrochemical labels (such as, for example, glucose or other reducing sugars, or thiols or other redox active moieties), luminescent labels, spin labels, radioactive labels, steric labels, affinity tags, or the like.

Particle-Nucleotide Conjugate

In a particle-nucleotide conjugate, multiple copies of the same nucleotide may be covalently bound to or noncovalently bound to the particle. Examples of the particle can include a branched polymer; a dendrimer; a cross linked polymer particle such as an agarose, polyacrylamide, acrylate, methacrylate, cyanoacrylate, methyl methacrylate particle; a glass particle; a ceramic particle; a metal particle; a quantum dot; a liposome; an emulsion particle, or any other particle (e.g., nanoparticles, microparticles, or the like) known in the art. In a preferred embodiment, the particle is a branched polymer.

The nucleotide can be linked to the particle through a linker, and the nucleotide can be attached to one end or location of a polymer. The nucleotide can be conjugated to the particle through the 5' end of the nucleotide. In some particle-nucleotide conjugates, one nucleotide attached to one end or location of a polymer. In some particle-nucleotide conjugate, multiple nucleotides are attached to one end or location of a polymer. The conjugated nucleotide is sterically accessible to one or more proteins, one or more enzymes, and nucleotide binding moieties. In some embodiments, a nucleotide may be provided separately from a nucleotide binding moiety such as a polymerase. In some embodiments, the linker does not comprise a photo emitting or photo absorbing group.

The particle can also have a binding moiety. In some embodiments, particles may self-associate without the use of a separate interaction moiety. In some embodiments, particles may self-associate due to buffer conditions or salt conditions, e.g., as in the case of calcium-mediated interactions of hydroxyapatite particles, lipid or polymer mediated interactions of micelles or liposomes, or salt-mediated aggregation of metallic (such as iron or gold) nanoparticles.

The particle-nucleotide conjugate can have one or more labels. Examples of the labels include but are not limited to fluorophores, spin labels, metals or metal ions, colorimetric labels, nanoparticles, PET labels, radioactive labels, or other such label as may render said composition detectable by such methods as are known in the art of the detection of macromolecules or molecular interactions. The label may be attached to the nucleotide (e.g. by attachment to the 5' phosphate moiety of a nucleotide), to the particle itself (e.g., to the PEG subunits), to an end of the polymer, to a central moiety, or to any other location within said polymer-nucleotide conjugate which would be recognized by one of skill in the art to be sufficient to render said composition, such as a particle, detectable by such methods as are known in the art or described elsewhere herein. In some embodiments, one or more labels are provided so as to correspond to or differentiate a particular particle-nucleotide conjugate.

In some embodiments, the label is a fluorophore. Exemplary fluorescent moieties include, but are not limited to, fluorescein and fluorescein derivatives such as carboxyfluorescein, tetrachlorofluorescein, hexachlorofluorescein, carboxynapthofluorescein, fluorescein isothiocyanate, NHS-fluorescein, iodoacetamidofluorescein, fluorescein maleimide, SAMSA-fluorescein, fluorescein thiosemicarbazide, carbohydrazinomethylthioacetyl-amino fluorescein, rhodamine and rhodamine derivatives such as TRITC, TMR, lissamine rhodamine, Texas Red, rhodamine B, rhodamine 6G, rhodamine 10, NHS-rhodamine, TMR-iodoacetamide, lissamine rhodamine B sulfonyl chloride, lissamine rhodamine B sulfonyl hydrazine, Texas Red sulfonyl chloride, Texas Red hydrazide, coumarin and coumarin derivatives such as AMCA, AMCA-NHS, AMCA-sulfo-NHS, AMCA-HPDP, DCIA, AMCE-hydrazide, BODIPY and derivatives such as BODIPY FL C3-SE, BODIPY 530/550 C3, BODIPY 530/550 C3-SE, BODIPY 530/550 C3 hydrazide, BODIPY 493/503 C3 hydrazide, BODIPY FL C3 hydrazide, BODIPY FL IA, BODIPY 530/551 IA, Br-BODIPY 493/503, Cascade Blue and derivatives such as Cascade Blue acetyl azide, Cascade Blue cadaverine, Cascade Blue ethylenediamine, Cascade Blue hydrazide, Lucifer Yellow and derivatives such as Lucifer Yellow iodoacetamide, Lucifer Yellow CH, cyanine and derivatives such as indolium based cyanine dyes, benzo-indolium based cyanine dyes, pyridium based cyanine dyes, thiozolium based cyanine dyes, quinolinium based cyanine dyes, imidazolium based cyanine dyes, Cy 3, Cy5, lanthanide chelates and derivatives such as BCPDA, TBP, TMT, BHHCT, BCOT, Europium chelates, Terbium chelates, Alexa Fluor dyes, DyLight dyes, Atto dyes, LightCycler Red dyes, CAL Flour dyes, JOE and derivatives thereof, Oregon Green dyes, WellRED dyes, IRD dyes, phycoerythrin and phycobilin dyes, Malachite green, stilbene, DEG dyes, NR dyes, near-infrared dyes and others known in the art such as those described in Haugland, Molecular Probes Handbook, (Eugene, Oreg.) 6th Edition; Lakowicz, Principles of Fluorescence Spectroscopy, 2nd Ed., Plenum Press New York (1999), or Hermanson, Bioconjugate Techniques, 2nd Edition, or derivatives thereof, or any combination thereof. Cyanine dyes may exist in either sulfonated or non-sulfonated forms, and consist of two indolenin, benzo-indolium, pyridium, thiozolium, and/or quinolinium groups separated by a polymethine bridge between two nitrogen atoms. Commercially available cyanine fluorophores include, for example, Cy3, (which may comprise 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-1,3-dihydro-2H-indol-2-ylidene}prop-1-en-1-yl)-3,3-dimethyl-3H-indolium or 1-[6-(2,5-dioxopyrrolidin-1-yloxy)-6-oxohexyl]-2-(3-{1-[6-(2,5-dioxopyrrolidin-1-yloxy)-6-oxohexyl]-3,3-dimethyl-5-sulfo-1,3-dihydro-2H-indol-2-ylidene}prop-1-en-1-yl)-3,3-dimethyl-3H-indolium-5-sulfonate), Cy5 (which may comprise 1-(6-((2,5-dioxopyrrolidin-1-yl)oxy)-6-oxohexyl)-2-((1E,3E)-5-

((E)-1-(6-((2,5-dioxopyrrolidin-1-yl)oxy)-6-oxohexyl)-3,3-dimethyl-5-indolin-2-ylidene)penta-1,3-dien-1-yl)-3,3-dimethyl-3H-indol-1-ium or 1-(6-((2,5-dioxopyrrolidin-1-yl)oxy)-6-oxohexyl)-2-((1E,3E)-5-((E)-1-(6-((2,5-dioxopyrrolidin-1-yl)oxy)-6-oxohexyl)-3,3-dimethyl-5-sulfoindolin-2-ylidene)penta-1,3-dien-1-yl)-3,3-dimethyl-3H-indol-1-ium-5-sulfonate), and Cy7 (which may comprise 1-(5-carboxypentyl)-2-[(1E,3E,5E,7Z)-7-(1-ethyl-1,3-dihydro-2H-indol-2-ylidene)hepta-1,3,5-trien-1-yl]-3H-indolium or 1-(5-carboxypentyl)-2-[(1E,3E,5E,7Z)-7-(1-ethyl-5-sulfo-1,3-dihydro-2H-indol-2-ylidene)hepta-1,3,5-trien-1-yl]-3H-indolium-5-sulfonate), where "Cy" stands for 'cyanine', and the first digit identifies the number of carbon atoms between two indolenine groups. Cy2 which is an oxazole derivative rather than indolenin, and the benzo-derivatized Cy3.5, Cy5.5 and Cy7.5 are exceptions to this rule.

In some embodiments, the detection label can be a FRET pair, such that multiple classifications can be performed under a single excitation and imaging step. As used herein, FRET may comprise excitation exchange (Forster) transfers, or electron-exchange (Dexter) transfers.

Nucleic Acid Hybridization

Disclosed herein are methods, compositions, systems, and kits for nucleic acid hybridization to nucleic acid molecules coupled to a surface. The methods, compositions, systems, and kits described herein are particularly useful for nucleic acid amplification, nucleic acid sequencing, or a combination thereof. The methods, compositions, systems, and kits described herein enable superior nucleic acid hybridization performance, and can be performed in a fraction of the cost and time, as compared with standard nucleic acid hybridization methods that exist. This is accomplished by utilizing optimized hybridization compositions (e.g., buffers, organic solvents) in combination with low non-specific binding surfaces that are hydrophilic.

Standard nucleic acid hybridization methods that exist are complex, time consuming, and lack the specificity and efficiency needed for cost-effective high throughput applications. Existing hybridization methods, in many cases, require a high temperature (e.g., 90 degrees Celsius) incubations, long incubation times (e.g., 1-2 hours), and large amounts of input nucleic acid (e.g., 10 nanomolar). At least one reason why standard nucleic acid hybridization methods lack specificity and efficiency, is because surfaces are used that are prone to non-specific binding of proteins or nucleic acids, contributing to increased background signal.

The methods, compositions, systems, and kits described herein provide superior hybridization specificity and efficiency of target nucleic acid molecules to surface-bound nucleic acid molecules, as compared to standard nucleic acid hybridization methods. Described herein, are methods and systems utilizing a low non-specific binding surface, thereby reducing background signal. The low non-specific binding surfaces described herein are engineered so that proteins, nucleic acids, and other biomolecules do not "stick" to the substrate of the surface. The low non-specific binding surfaces described herein are hydrophilic. In some cases, the low non-specific binding surfaces have a water contact angle of less than or equal to about 50 degrees.

In some embodiments, methods comprise hybridizing a target nucleic acid to a nucleic acid molecule coupled to a hydrophilic surface (e.g., low non-specific binding surface) that utilize the hybridization compositions described herein. The methods described herein are useful for nucleic acid hybridization, amplification, sequencing, or a combination thereof. The methods described herein achieve superior hybridization performance on the low non-specific binding surfaces. In addition, the methods described herein achieve a non-specific cyanine dye-3 (Cy3) dye absorption of less than about 0.25 molecules/$\mu m^2$.

Optimized hybridization compositions described herein, particularly when used with the low non-specific binding surfaces, enable isothermal hybridization reactions to be performed at 60 degrees Celsius for as few as 2 minutes using as little as 50 picomolar concentration of input nucleic acid. Methods described herein provide (i) superior hybridization rates, (ii) superior hybridization specificity, (iii) superior hybridization stringency, (iv) superior hybridization efficiency (or yield), (v) reduced requirements for the amount of starting material necessary, (vi) lowered temperature requirements for isothermal or thermal ramping amplification protocols, (vii) increased annealing rates, and (viii) yield a low percentage of the total number target nucleic acid molecules (or amplified clusters of target nucleic acid molecules) being associated with the surface without hybridizing to the surface bound nucleic acid, as compared with a comparable hybridization reaction with standard hybridization protocols and reagents. The increased performance and reduced cost and time required to perform a hybridization reaction make the methods, compositions, systems, and kits ideally suited for high throughput nucleic acid hybridization, amplification, and sequencing applications.

Standard hybridization formulations (e.g., saline sodium citrate buffer) achieve poor hybridization specificity or efficiency when used with standard hybridization protocols using the non-specific binding surfaces described herein. The hybridization reaction or annealing interaction between target nucleic acid molecules in the solution and nucleic acid molecules coupled to the low non-specific binding surfaces can be impacted by several factors, including the availability of hydrogen bonding partners in the solution and the polarity of the solution. In general, nucleic acids preferentially inhabit bulk solution where possible in order to take advantage of the additional entropic stabilization presented by the ability to access dynamic states in three, rather than two, dimensions such as would be available on a solid surface. At equilibrium, in a system comprising a nucleic acid, a solution, and a hydrophilic surface (e.g., low non-specific binding surface), a nucleic acid molecule will be preferentially stabilized in solution, rather than in a surface-bound state when the solvent is aqueous.

Existing hybridization utilize protic solvents (e.g., saline sodium citrate buffer), which are disadvantageous for nucleic acid hybridization reactions with the low non-specific binding surfaces described herein, because aprotic solvents provide a favorable environment for the target nucleic acid molecules to stay in solution, rather than binding to the low non-specific binding surface. This is due to the ability of the protic solvent to provide sufficient hydrogen bonding partners of sufficient size and distribution such that hydrogen bonding interactions between the exposed hydrogen bond donors and acceptors along the nucleic acid backbone, or, any exposed sidechain moieties, occur.

By contrast, the hybridization compositions described herein drive the target nucleic acid molecule to the low non-specific binding surface while in solution, by utilizing an aprotic organic solvent. The aprotic solvents described herein reduce the proportion of solvent molecules capable of satisfying the hydrogen bonding requirements of the nucleic acid chain, and make it possible to create an entropic penalty in the bulk solution, which will drive the system toward stabilization by depositing the nucleic acid on the surface (e.g., the entropic penalty caused by ordering the bulk solution to accommodate the unbonded hydrogen bonding elements in the nucleic acid becomes greater than the entropic penalty caused by loss of the third dimension of dynamic freedom when the polymer is adsorbed to the surface). Furthermore, introduction of an aprotic organic solvent into the solution may help drive down the entropy and in turn provides a more favorable environment for the nucleic acid to bind to the hydrophilic surface. For example, addition of an aprotic r solvent acetonitrile helps to drive the nucleic acid in the solution towards a surface bound state.

The hybridization compositions described herein further comprise a concentrations of protic and aprotic organic solve, to prevent precipitation of the target nucleic acid from solution that can be caused by high concentrations of aprotic solvent in the solution. In this manner, the hybridization compositions described herein cause the nucleic acids to selectively associate with hydrophilic surfaces (e.g., low non-specific binding surfaces), while remaining substantially solvated.

The hybridization compositions described herein optionally comprise crowding agents, which are capable of modulating interactions of nucleic acids with the bulk solution. In some cases, the hybridization compositions comprise relaxing agents, divalent cations, or intercalating agents, which are capable of modulating the dynamics of the polymer itself, and may also modulate the interactions of nucleic acids with surfaces in the presence of partially aprotic bulk solvents. Providing such agents in combination with buffers containing some fraction of aprotic or non-hydrogen-bonding components can, in some cases, provide superior control over the interaction of nucleic acid molecules with hydrophilic surfaces.

Various aspects of the disclosed nucleic acid hybridization methods may be applied to solution-phase or solid-phase nucleic acid hybridization, and also to any other type of nucleic acid amplification, or, analysis applications (e.g., nucleic acid sequencing), or any combination thereof. It shall be understood that different aspects of the disclosed methods, devices, and systems can be appreciated individually, collectively, or in combination with each other.

The methods, compositions, systems, and kits described herein are useful for a wide range of applications beyond those involving nucleic acid-surface interactions, because the same thermodynamic parameters optimized by the methods and compositions described herein govern a number of interactions between polymers and biomolecules, as well as polymer and surface interactions and biomolecule and surface interactions. Thus, the methods compositions, systems and kits described herein may be applied to tune the polarity, or the hydrogen bonding potential, or a combination thereof, of a solvent in other systems involving these interactions.

Solution-based hybridization is the foundation for many solution-based molecular biology and solution-phase DNA manipulation applications, most notably the polymerase chain reaction (PCR) (L. Garibyan and N. Avashia, J. Invest. Dermatol., 2013, 133, e6; Z. Xiao, D. Shangguan, Z. Cao, X. Fang, and W. Tan, 2008, DNA guided drug delivery, Chemistry 14, 1769-75; and F. Wei, C. Chen, L. Zhai, N. Zhang, and X. S. Zhao, 2005, DNA based biosensors, J. Am. Chem. Soc., 127, 5306-5307; and S. Tyagi and F. R. Kramer, Nat. Biotechnol., 1996, 14, 303-308. The diffusion rates in many of these reactions are sufficient to drive efficient hybridization and the formation of a functional double-stranded form, which can be analyzed kinetically as a second order kinetic reaction, whereby the forward reaction of duplex formation is second order and the reverse reaction comprising the dissociation of the duplex structure to form the two single stranded complements (strands A and B) is first order (Han, C., Improvement of the Speed and Sensitivity of DNA Hybridization Using Isotachophoresis, Stanford Thesis. 2015). These reactions may be written as:

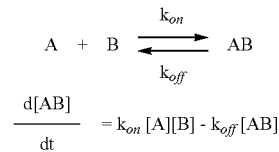

$$A + B \underset{k_{off}}{\overset{k_{on}}{\rightleftharpoons}} AB$$

$$\frac{d[AB]}{dt} = k_{on}[A][B] - k_{off}[AB]$$

Various approaches have been deployed to increase not only the speed of the hybridization reaction but also the reaction specificity in the wake of confounding DNA non-complementary fragments. Such approaches include, but are not limited to, the addition of $MgCl_2$ and higher salt concentrations, and lower temperatures to accelerate the reactions (H. Kuhn, V. V Demidov, J. M. Coull, M. J. Fiandaca, B. D. Gildea, and M. D. Frank-Kamenetskii, J. Am. Chem. Soc., 2002, 124, 1097-1103; N. A. Straus and T. I. Bonner, Biochim. Biophys. Acta, Nucleic Acids Protein Synth., 1972, 277, 87-95). The trade-off for accelerated reaction rates is often reaction specificity (J. M. S. Bartlett and D. Stirling, PCR protocols, Humana Press, 2003; W. Rychlik, W. J. Spencer, and R. E. Rhoads, Nucleic Acids Res., 1990, 18). Additional methods are sometimes employed that yield potential improvements of reaction specificity through the use of volume exclusion, or, molecular crowding techniques, or a combination thereof that utilize inert polymers as hybridization buffer additives (R. Wieder and J. G. Wetmur, Biopolymers, 1981, 20, 1537-1547, J. G. Wetmur, Biopolymers, 1975, 14, 2517-2524). In addition, organic solvents have been employed as additives to accelerate hybridization kinetics and maintain reaction specificity (N. Dave and J. Liu, J. Phys. Chem. B, 2010, 114, 15694-15699).

While hybridization improvements in solution may be translated to surface-based hybridization techniques, surface-based hybridization needs have far ranging implications for many critical bioassays, such as gene expression analysis (D. T. Ross, U. Scherf, M. B. Eisen, C. M. Perou, C. Rees, P. Spellman, V. Iyer, S. S. Jeffrey, M. Van de Rijn, M. Waltham, A. Pergamenschikov, J. C. Lee, D. Lashkari, D. Shalon, T. G. Myers, J. N. Weinstein, D. Botstein, and P. O. Brown, Nat. Genet., 2000, 24, 227-235; A. Adomas, G. Heller, A. Olson, J. Osborne, M. Karlsson, J. Nahalkova, L. Van Zyl, R. Sederoff, J. Stenlid, R. Finlay, and F. O. Asiegbu, Tree Physiol., 2008, 28, 885-897; M. Schena, D. Shalon, R. W. Davis, and P. O. Brown, Science, 1995, 270, 467-470), diagnosis of disease (J. Marx, Science, 2000, 289, 1670-1672), genotyping and SNP detection (J. G. Hacia, J. B. Fan, O. Ryder, L. Jin, K. Edgemon, G. Ghandour, R. A. Mayer, B. Sun, L. Hsie, C. M. Robbins, L. C. Brody, D. Wang, E. S. Lander, R. Lipshutz, S. P. Fodor, and F. S. Collins, Nat. Genet., 1999, 22, 164-167), rapid pathogen nucleic acid based pathogen screening, next generation sequencing (NGS) and a host of other genomics based applications (M. J. Heller, Annu. Rev. Biomed. Eng., 2002, 4, 129-53). The common necessity of all of these reactions is high reaction specificity in a highly multiplexed solution of target sequences that may range from thousands to billions of different sequences, such that the targets are quickly tethered on a solid surface for subsequent probing, or, amplification, or a combination thereof to enable DNA (or other nucleic acid) interrogation for applications such as sequencing or array-based analysis. The efficiency of surface-based hybridization reactions were found to be much less than that of in solution reactions, e.g., about an order of magnitude less efficient. A great deal of work has been done in past attempts to create a hybridization method for solid surface s that provides high specificity and accelerated hybridization reaction rates (D. Y. Zhang, S. X. Chen, and P. Yin, Nat. Chem., 2012, 4, 208-14).

Disclosed herein are innovative combinations of approaches gleaned from studies of surface- and solution-based hybridization as outlined above, as well as from other fields of study that include DNA hydration and quadruplex studies, which lead to substantial improvements in hybridization kinetics and specificity. The disclosed hybridization compositions provide for highly specific (e.g., >2 orders of magnitude improvement over traditional approaches) and accelerated hybridization (e.g., >1-2 orders of magnitude improvement over traditional approaches) when used with low non-specific binding surface for applications such as next generation sequencing (NGS) and other bioassays that require highly specific nucleic acid hybridization in a multiplexed pool comprised of large number of target sequences.

Hybridization Methods

Figure 13:
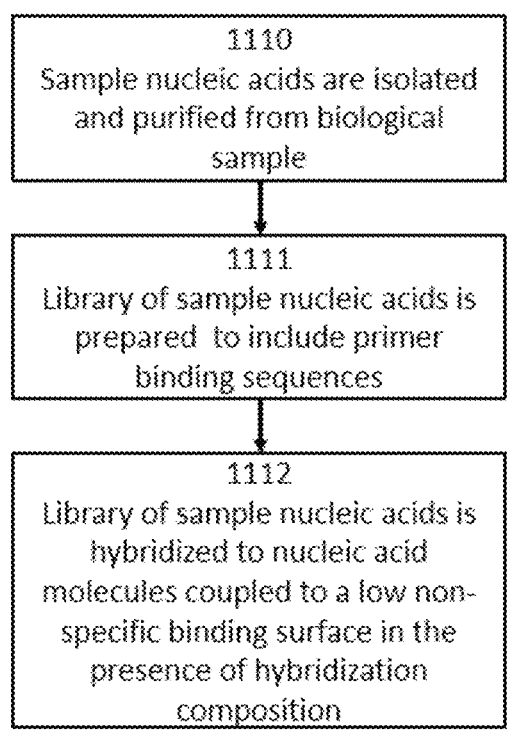
FIG. 13 shows a workflow of purification and isolation of sample nucleic acids from a biological sample, library preparation, and hybridization according to various embodiments described herein.

Provided herein are methods for nucleic acid hybridization between a sample nucleic acid molecule and a capture nucleic acid molecule. Referring to FIG. 13, the sample nucleic acid molecule is isolated and purified from a biological sample obtained from a subject 1110. A library of isolated and purified sample nucleic acid molecules is prepared 1111. The library of sample nucleic acid molecules is hybridized to nucleic acid molecules coupled to a low non-specific binding surface described herein in the presence of a hybridization composition 1112.

Biological Sample. The biological sample disclosed herein comprise nucleic acid molecules, amino acids, polypeptides, proteins, carbohydrates, fats, or viruses. In an example, a biological sample is a nucleic acid sample including one or more nucleic acid molecules. Exemplary biological samples may include polynucleotides, nucleic acids, oligonucleotides, cell-free nucleic acid (e.g., cell-free DNA (cfDNA)), circulating cell-free nucleic acid, circulating tumor nucleic acid (e.g., circulating tumor DNA (ctDNA)), circulating tumor cell (CTC) nucleic acids, nucleic acid fragments, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA), ribosomal RNA, cell-free DNA, cell free fetal DNA (cffDNA), mRNA, rRNA, tRNA, nRNA, siRNA, snRNA, snoRNA, scaRNA, microRNA, dsRNA, viral RNA, and the like.

Any substance that comprises nucleic acid may be the source of the biological sample. The substance may be a fluid, e.g., a biological fluid. A fluidic substance may include, but not limited to, blood, cord blood, saliva, urine, sweat, serum, semen, vaginal fluid, gastric and digestive fluid, spinal fluid, placental fluid, cavity fluid, ocular fluid, serum, breast milk, lymphatic fluid, or combinations thereof. The substance may be solid, for example, a biological tissue. The substance may comprise normal healthy tissues, diseased tissues, or a mix of healthy and diseased tissues.

Biological samples described herein are obtained from various subjects. A subject may be a living subject or a dead subject. Examples of subjects may include, but not limited to, humans, mammals, non-human mammals, rodents, amphibians, reptiles, canines, felines, bovines, equines, goats, ovines, hens, avines, mice, rabbits, insects, slugs, microbes, bacteria, parasites, or fish. The subject, in comes cases, is a patient who is having, suspected of having, or at a risk of developing a disease or disorder. In some cases, the subject may be a pregnant woman. In some case, the subject may be a normal healthy pregnant woman. In some cases, the subject may be a pregnant woman who is at a risking of carrying a baby with certain birth defect.

A sample may be obtained from a subject by various approaches. For example, a sample may be obtained from a subject through accessing the circulatory system (e.g., intravenously or intra-arterially via a syringe or other apparatus), collecting a secreted biological sample (e.g., saliva, sputum urine, feces), surgically (e.g., biopsy) acquiring a biological sample (e.g., intra-operative samples, post-surgical samples), swabbing (e.g., buccal swab, oropharyngeal swab), or pipetting.

Biological Sample Processing. The biological sample described herein, in some cases, is processed. Processing comprises filtering a sample, binding a component of the sample that contains an analyte, binding the analyte, stabilizing the analyte, purifying the analyte, or a combination thereof. Non-limiting examples of sample components are cells, viral particles, bacterial particles, exosome, and nucleosomes. In some cases, blood plasma or serum is isolated from a whole blood sample. In some cases, the whole blood is obtained from venous blood or capillary blood of a subject described herein.

Library Preparation of Sample Nucleic Acids. The sample nucleic acids described herein, in some cases, are converted to a library by labeling the sample nucleic acids with a label, barcode or tag. The library of sample nucleic acids are amplified in some embodiments, for example, by isothermal amplification. Non-limiting examples of amplification methods include loop mediated isothermal amplification (LAMP), nucleic acid sequence based amplification (NASBA), strand displacement amplification (SDA), multiple displacement amplification (MDA), rolling circle amplification (RCA), ligase chain reaction (LCR), helicase dependent amplification (HDA), nicking enzyme amplification reaction (NEAR), recombinase polymerase amplification (RPA), and ramification amplification method (RAM).

In some instances, isothermal amplification is used. In some instances, amplification is isothermal with the exception of an initial heating step before isothermal amplification begins. A number of isothermal amplification methods, each having different considerations and providing different advantages, are known in the art and have been discussed in the literature, e.g., by Zanoli and Spoto, 2013, "Isothermal Amplification Methods for the Detection of Nucleic Acids in Microfluidic Devices," Biosensors 3: 18-43, and Fakruddin, et al., 2013, "Alternative Methods of Polymerase Chain Reaction (PCR)," Journal of Pharmacy and Bioallied Sciences 5(4): 245-252, each incorporated herein by reference in its entirety.

In some instances, the amplification method is Rolling Circle Amplification (RCA). RCA is an isothermal nucleic acid amplification method which allows amplification of the probe DNA sequences by more than $10^9$ fold at a single temperature, typically about 30° C. Numerous rounds of isothermal enzymatic synthesis are carried out by 029 DNA polymerase, which extends a circle-hybridized primer by continuously progressing around the circular DNA probe. In some instances, the amplification reaction is carried out using RCA, at about 28° C. to about 32° C. Suitable methods of RCA are described in U.S. Pat. No. 6,558,928.

In some instances, amplifying comprises targeted amplification. In some instances, amplifying a nucleic acid comprises contacting a nucleic acid with at least one primer having a sequence corresponding to a target chromosome sequence. Amplification may be multiplexed, involving contacting the nucleic acid with multiple sets of primers, wherein each of a first pair in a first set and each of a pair in a second set are all different.

Hybridization. Methods described herein comprise bringing a sample nucleic acid molecule into contact with a capture nucleic acid molecule that is optionally coupled to a low non-specific binding surface in the presence of a hybridization composition described herein. In some cases, the capture nucleic acid molecule is coupled to the low non-specific binding surface and hybridization occurs on the surface. In some cases, the capture nucleic acid molecules are not coupled to the low non-specific binding surface and hybridization occurs in solution. Methods provided herein further comprising hybridizing the sample nucleic acid molecule with the capture nucleic acid molecule.

Methods comprise hybridizing at least a portion of the sample nucleic acid molecule comprising a nucleic acid sequence that is sufficiently complementary to a portion of the capture nucleic acid molecule. The portion of the capture nucleic acid molecule and the sample nucleic acid molecule can be at least or equal to about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides. The portion of the capture nucleic acid molecule and the sample nucleic acid molecule can be between 4 and 50, 5 and 49, 6 and 48, 7 and 47, 8 and 46, 9 and 45, 10 and 44, 11 and 43, 12 and 42, 13 and 41, 14 and 40, 15 and 39, 16 and 38, 17 and 37, 18 and 36, 19 and 35, 20 and 34, 21 and 33, 22 and 32, 23 and 31, 24 and 30, 25 and 29, 26 and 28 nucleotides. The portion of the capture nucleic acid molecule and the sample nucleic acid molecule can be between 8 and 20 nucleotides. In some instances, at least 90% of the nucleic acids in the portion of the sample nucleic acid molecule and the portion of the capture nucleic acid molecule hybridize completely. In some instances, at least 95% of the nucleic acids in the portion of the sample nucleic acid molecule and the portion of the capture nucleic acid molecule hybridize completely. In some instances, between 95-100% of the nucleic acids in the portion of the sample nucleic acid molecule and the portion of the capture nucleic acid molecule hybridize completely.

Figure 10:
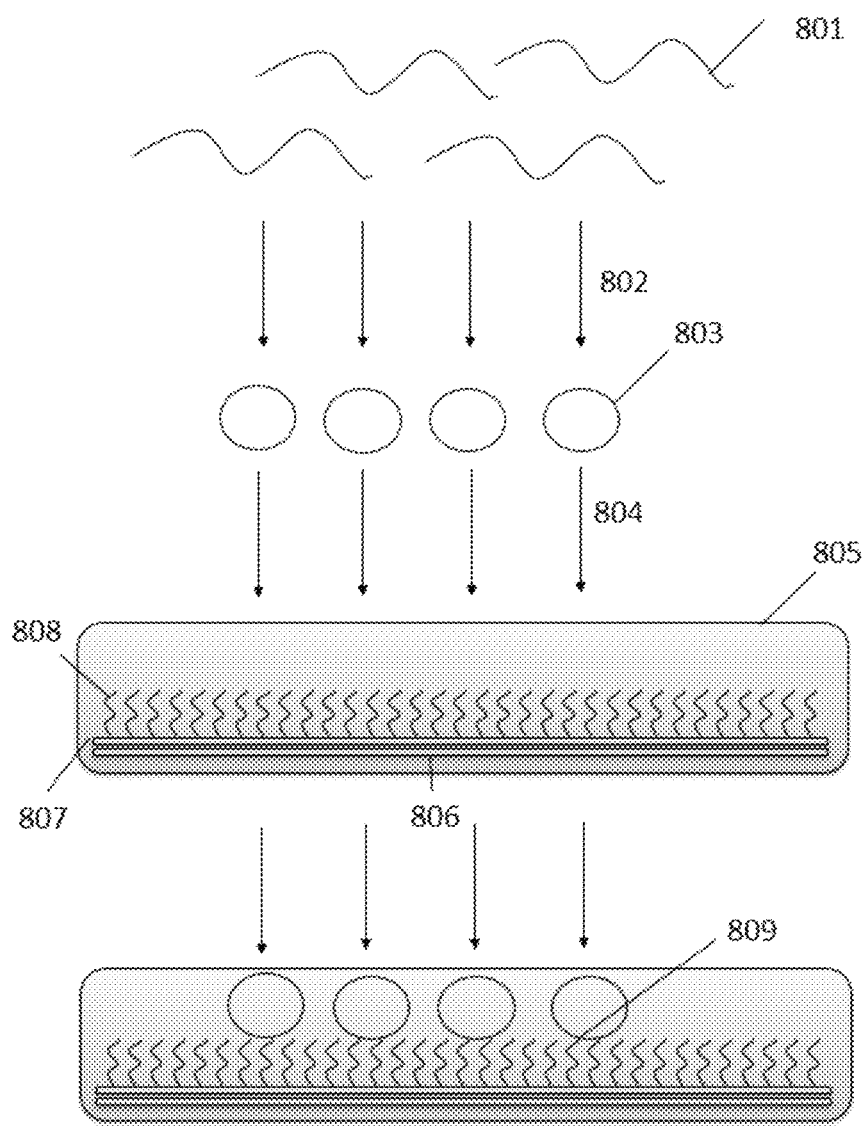
FIG. 10 shows a sample nucleic acid hybridization workflow according to various embodiments described herein.
Figure 11A:
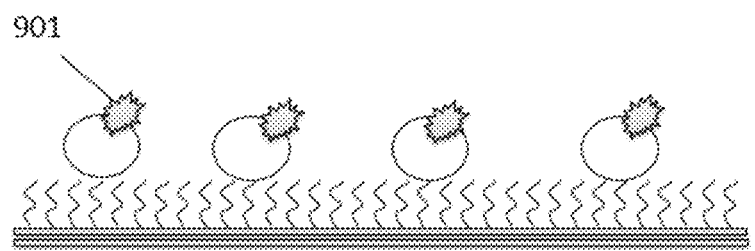
FIG. 11A-11B show how sample nucleic acids hybridized to the nucleic acid molecules coupled to the low-non-specific binding surface is visualized (FIG. 11A) or amplified (FIG. 11B) according to various embodiments described herein.
Figure 11B:
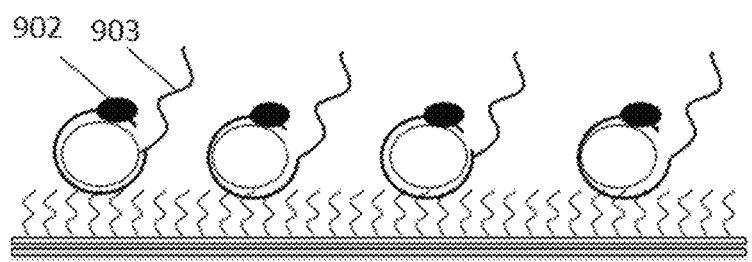

A non-limiting example provided in FIG. 10 shows one or more sample nucleic acid molecules 801 that is circularized 802 using ligation (e.g., splint ligation) 802, and introduced to one or more nucleic acid molecules 808 coupled a hydrophilic substrate 807 of a low non-specific binding surface 806 in the presence of a hybridization composition 805. In this example, the low-non-specific binding surface is submerged in the hybridization composition. In alternative embodiments, the one or more sample nucleic acid molecules is introduced to the hybridization composition before introduction to the one or more nucleic acid molecules 808 coupled to the hydrophilic substrate 807 of the low non-specific binding surface 806. Hybridization occurs between the sample nucleic acid molecule and the surface-coupled nucleic acid molecule 809.

Sample Nucleic Acids. The one or more sample nucleic acid molecules described herein is derived from a biological sample described herein. The sample nucleic acid molecules is a deoxyribonucleic acid (DNA) molecule or ribonucleic acid (RNA) molecule. In some cases, the DNA is selected from cell-free DNA (cfDNA)), circulating cell-free nucleic acid, circulating tumor nucleic acid (e.g., circulating tumor DNA (ctDNA)), circulating tumor cell (CTC) nucleic acids, nucleic acid fragments, nucleotides, DNA, complementary DNA (cDNA), double stranded DNA (dsDNA), single stranded DNA (ssDNA), plasmid DNA, cosmid DNA, chromosomal DNA, genomic DNA (gDNA), viral DNA, bacterial DNA, mtDNA (mitochondrial DNA). In some cases, the RNA is selected from ribosomal RNA, cell-free DNA, cell free fetal DNA (cffDNA), mRNA, rRNA, tRNA, nRNA, siRNA, snRNA, snoRNA, scaRNA, microRNA, dsRNA, viral RNA, and the like.

Coupling the Capture Nucleic Acids to the Surface. The nucleic acid molecules coupled to the surface (e.g., capture molecule) may be coupled to the surface by a number of suitable options. In some instances, the nucleic acid molecules are coupled to the surface through covalent bond. In some instances, the nucleic acid molecules are coupled to the surface through noncovalent bond. In some instances, the nucleic acid molecules are attached to the surface through a bio-interaction. Non-limiting examples of bio-interaction surface chemistry include biotin-streptavidin interactions (or variations thereof), polyhistidine (his) tag-Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

Compositions

Provided herein are hybridization compositions. The hybridization compositions of the present disclosure comprise at least one organic solvent, which in some cases is polar and aprotic (e.g., having a dielectric constant of less than or equal to about 115 as measured at 68 degrees F.). The hybridization compositions comprise a pH buffer. Optionally, the hybridization compositions comprise one or more molecular crowding/volume exclusion agents, one or more additives that impact DNA melting temperatures, one or more additives that impact DNA hydration, or any combination thereof. The hybridization compositions described herein used with the low non-specific binding surfaces, such as silicon dioxide coated with low binding polymers such as polyethylene glycol (PEG) for sequencing, genotyping, or sequencing related technologies may be achieved using any or a combination of the following hybridization composition components.

Organic Solvent: An organic solvent is a solvent or solvent system comprising carbon-based or carbon-containing substance capable of dissolving or dispersing other substances. An organic solvent may be miscible or immiscible with water.

Polar Solvent: A polar solvent as included in the hybridization composition described herein is a solvent or solvent system comprising one or more molecules characterized by the presence of a permanent dipole moment, e.g., a molecule having a spatially unequal distribution of charge density. A polar solvent may be characterized by a dielectric constant of 20, 25, 30, 35, 40, 45, 50, 55, 60 or higher or by a value or a range of values incorporating any of the aforementioned values. For example, a polar solvent may have a dielectric constant of higher than 100, higher than 110, higher than 111, or higher than 115. In some cases, the dielectric constant is measured at a temperature of greater than or equal to about 20, 25, 30, 35, 40, 45, 50, 55, 60, 65, 70, 75, 80, 85, 90, 95, 100, 150, 200, 250, 300, 350, 400, 450, or 500 degrees Fahrenheit (F). In some cases, the dielectric constant is measured at a temperature of less than or equal to about −20, −25, −30, −35, −40, −45, −50, −55, −60, −65, −70, −75, −80, −85, −90, −95, −100, −150, −200, −250, −300, −350, −400, −450, or −459 degrees F. In some cases, the dielectric constant is measured at a temperature of at 68 degrees F. In some cases, the dielectric constant is measured at a temperature of at 20 degrees F.

A polar solvent as described herein may comprise a polar aprotic solvent. A polar aprotic solvent as described herein may further contain no ionizable hydrogen in the molecule. In addition, polar solvents or polar aprotic solvents may be preferably substituted in the context of the presently disclosed compositions with a strong polarizing functional groups such as nitrile, carbonyl, thiol, lactone, sulfone, sulfite, and carbonate groups so that the underlying solvent molecules have a dipole moment. Polar solvents and polar aprotic solvents can be present in both aliphatic and aromatic or cyclic form. In some embodiments, the polar solvent is acetonitrile.

The organic solvent described herein can have a dielectric constant that is the same as or close to acetonitrile. The dielectric constant of the organic solvent can be in the range of about 20-60, about 25-55, about 25-50, about 25-45, about 25-40, about 30-50, about 30-45, or about 30-40. The dielectric constant of the organic solvent can be greater than or equal to about 20, 25, 30, 35, or 40. The dielectric constant of the organic solvent can be lower than 30, 40, 45, 50, 55, or 60. The dielectric constant of the organic solvent can be about 35, 36, 37, 38, or 39.

Dielectric constant may be measured using a test capacitor. Representative polar solvents having a dielectric constant between 30 and 120 may be used. Such solvents may particularly include, but are not limited to, acetonitrile, diethylene glycol, N,N-dimethylacetamide, dimethyl formamide, dimethyl sulfoxide, ethylene glycol, formamide, hexamethylphosphoramide, glycerin, methanol, N-methyl-2-pyrrolidinone, nitrobenzene, or nitromethane. In some embodiments, the solvent may be protic or aprotic.

The organic solvent described herein can have a polarity index that is the same as or close to acetonitrile. The polarity index of the organic solvent can be in the range of about 2-9, 2-8, 2-7, 2-6, 3-9, 3-8, 3-7, 3-6, 4-9, 4-8, 4-7, or 4-6. The polarity index of the organic solvent can be greater than or equal to about 2, 3, 4, 4.5, 5, 5.5, or 6. The polarity index of the organic solvent can be lower than about 4.5, 5, 5.5, 6, 6.5, 7, 7.5, 8, 8.5, 9, or 10. The polarity index of the organic solvent can be about 5.5, 5.6, 5.7, or 5.8.

The Snyder Polarity Index may be calculated according to the methods disclosed in Snyder, L. R., Journal of Chromatography A, 92(2):223-30 (1974), which is incorporated by reference herein in it its entirety. Representative polar aprotic solvents having a Snyder polarity index between 6.2 and 7.3 may be used. Such solvents may particularly include, but are not limited to, acetonitrile, dimethyl acetamide, dimethyl formamide, N-methyl pyrrolidine, N,N-dimethyl sulfoxide, methanol, or formamide. In some embodiments, the solvent may be protic or aprotic.

Relative polarity may be determined according to the methods given in Reichardt, C., *Solvents and Solvent Effects in Organic Chemistry*, 3rd ed., 2003, which is incorporated herein by reference in its entirety, and especially with respect to its disclosure of polarities and methods of determining or assessing the same for solvents and solvent molecules. Polar aprotic solvents having a relative polarity between 0.44 and 0.82 may be used. Such solvents may particularly include, but are not limited to, dimethylsulfoxide, acetonitrile, 3-pentanol, 2-pentanol, 2-butanol, Cyclohexanol, 1-octanol, 2-propanol, 1-heptanol, i-butanol, 1-hexanol, 1-pentanol, acetyl acetone, ethyl acetoacetate, 1-butanol, benzyl alcohol, 1-propanol, 2-aminoethanol, Ethanol, diethylene glycol, methanol, ethylene glycol, glycerin, or formamide. In some embodiments, the solvent may be protic or aprotic.

The Solvent Polarity ($E_T(30)$) may be calculated according to the methods disclosed in Reichardt, C., *Molecular Interactions*, Volume 3, Ratajczak, H. and Orville, W. J., Eds (1982), which is incorporated by reference herein in it its entirety.

Some examples of organic solvent include but are not limited to acetonitrile, dimethylformamide (DMF), dimethylsulfoxide (DMSO), acetanilide, N-acetyl pyrrolidone, 4-amino pyridine, benzamide, benzimidazole, 1,2,3-benzotriazole, butadienedioxide, 2,3-butylene carbonate, γ-butyrolactone, caprolactone (epsilon), chloro maleic anhydride, 2-chlorocyclohexanone, chloroethylene carbonate, chloronitromethane, citraconic anhydride, crotonlactone, 5-cyano-2-thiouracil, cyclopropylnitrile, dimethyl sulfate, dimethyl sulfone, 1,3-dimethyl-5-tetrazole, 1,5-dimethyl tetrazole, 1,2-dinitrobenzene, 2,4-dinitrotoluene, dipheynyl sulfone, 1,2-dinitrobenzene, 2,4-dinitrotoluene, dipheynyl sulfone, epsilon-caprolactam, ethanesulfonylchloride, ethyl ethyl phosphinate, N-ethyl tetrazole, ethylene carbonate, ethylene trithiocarbonate, ethylene glycol sulfate, ethylene glycol sulfite, furfural, 2-furonitrile, 2-imidazole, isatin, isoxazole, malononitrile, 4-methoxy benzonitrile, 1-methoxy-2-nitrobenzene, methyl alpha bromo tetronate, 1-methyl imidazole, N-methyl imidazole, 3-methyl isoxazole, N-methyl morpholine-N-oxide, methyl phenyl sulfone, N-methyl pyrrolidinone, methyl sulfolane, methyl-4-toluenesulfonate, 3-nitroaniline, nitrobenzimidazole, 2-nitrofuran, 1-nitroso-2-pyrolidinone, 2-nitrothiophene, 2-oxazolidinone, 9,10-phenanthrenequinone, N-phenyl sydnone, phthalic anhydride, picolinonitrile (2-cyanopyridine), 1,3-propane sultone, β-propiolactone, propylene carbonate, 4H-pyran-4-thione, 4H-pyran-4-one (γ-pyrone), pyridazine, 2-pyrrolidone, saccharin, succinonitrile, sulfanilamide, sulfolane, 2,2,6,6-tetrachlorocyclohexanone, tetrahydrothiapyran oxide, tetramethylene sulfone (sulfolane), thiazole, 2-thiouracil, 3,3,3-trichloro propene, 1,1,2-trichloro propene, 1,2,3-trichloro propene, trimethylene sulfide-dioxide, and trimethylene sulfite.

Polar solvents having a solvent polarity between 44 and 60 may be used. Such solvents may particularly include, but are not limited to, dimethyl sulfoxide, 2-methoxycarbonylphenol, triethyl phosphite, 3-pentanol, acetonitrile, nitromethane, cyclohexanol, 2-pentanol, 4-methyl-1,3, dioxolan-2-one, propylene carbonate, acrylonitrile, 1-phenylethanol, 1-dodecanol, 2-butanol, 2-methylcyclohexanol, 2,6, dimethylphenol, 2,6-xylenol, 1-decanol, cyclopentanol, dimethyl sulfone, 1-octanoldiethylene glycol mono n-butyl ether, butyl digol, 1-heptanol, 3-phenyl-1-propanol, 1,3-dioxolane-2-one, ethylene carbonate, 1-hexanol, 4-chlorobutyronitrile, 5-methyl-2-isopropylphenol, thymol, 3,5,5-trimethyl-1-hexanol, 3-methyl-1-butanol, isoamyl alcohol, 2-methyl-1-propanol, isobutyl alcohol, 2-(tert-butyl)phenol, 1-pentanol, 2-phenylethanol, 2-methylpentane-2,4-diol, dipropylene glycol, 2-isopropylphenol, 2-n-butoxyethanol, ethylene glycol mono-n-butyl ether, 1-butanol, 2-hydroxymethyl-tetrahydrofuran, tetrahydrofurfuryl alcohol, 2-hydroxymethylfuran, furfuryl alcohol, 1-propanol, 2,4-dimethylphenol, 2,4-xylenol, benzyl alcohol, 2-ethoxyphenol, 2-ethoxyethanol, 1,5-pentanediol, 1-bromo-2-propanol, 2-methyl-5-isopropylphenol, carvacrol, 2-aminoethanol, ethanol, n-methylacetamide, 3-chloropropionitrile, 2-propen-1-ol, allyl alcohol, 2-methoxyethanol, 2-methylphenol, o-cresol, 1,3-butanediol, 2-propyn-1-ol, propargyl alcohol, 3-methylphenol, m-cresol, triethylene glycol, diethylene glycol, n-methylformamide, 1,2-propanediol, 1,3-propanediol, 2-chlorophenol, methanol, 1,2-ethanediol, glycol, formamide, 2,2,2-trichloroethanol, 1,2,3-propanetriol, glycerol, 2,2,3,3-tetrafluoro-1-propanol, 2,2,2-trifluoroethanol, 4-n-butylphenol, 4-methylphenol, or p-cresol. In some embodiments, the solvent may be protic or aprotic.

Polar solvents having a dielectric constant in the range of about 30-115 may be used. Such solvents may particularly include, but are not limited to, dimethyl sulfoxide, 2-methoxycarbonylphenol, triethyl phosphite, 3-pentanol, acetonitrile, nitromethane, cyclohexanol, 2-pentanol, 4-methyl-1,3, dioxolan-2-one, propylene carbonate, acrylonitrile, 1-phenylethanol, 1-dodecanol, 2-butanol, 2-methylcyclohexanol, 2,6, dimethylphenol, 2,6-xylenol, 1-decanol, cyclopentanol, dimethyl sulfone, 1-octanoldiethylene glycol mono n-butyl ether, butyl digol, 1-heptanol, 3-phenyl-1-propanol, 1,3-dioxolane-2-one, ethylene carbonate, 1-hexanol, 4-chlorobutyronitrile, 5-methyl-2-isopropylphenol, thymol, 3,5,5-trimethyl-1-hexanol, 3-methyl-1-butanol, isoamyl alcohol, 2-methyl-1-propanol, isobutyl alcohol, 2-(tert-butyl)phenol, 1-pentanol, 2-phenylethanol, 2-methylpentane-2,4-diol, dipropylene glycol, 2-isopropylphenol, 2-n-butoxyethanol, ethylene glycol mono-n-butyl ether, 1-butanol, 2-hydroxymethyl-tetrahydrofuran, tetrahydrofurfuryl alcohol, 2-hydroxymethylfuran, furfuryl alcohol, 1-propanol, 2,4-dimethylphenol, 2,4-xylenol, benzyl alcohol, 2-ethoxyphenol, 2-ethoxyethanol, 1,5-pentanediol, 1-bromo-2-propanol, 2-methyl-5-isopropylphenol, carvacrol, 2-aminoethanol, ethanol, n-methylacetamide, 3-chloropropionitrile, 2-propen-1-ol, allyl alcohol, 2-methoxyethanol, 2-methylphenol, o-cresol, 1,3-butanediol, 2-propyn-1-ol, propargyl alcohol, 3-methylphenol, m-cresol, triethylene glycol, diethylene glycol, n-methylformamide, 1,2-propanediol, 1,3-propanediol, 2-chlorophenol, methanol, 1,2-ethanediol, glycol, formamide, 2,2,2-trichloroethanol, 1,2,3-propanetriol, glycerol, 2,2,3,3-tetrafluoro-1-propanol, 2,2,2-trifluoroethanol, 4-n-butylphenol, 4-methylphenol, or p-cresol. In some embodiments, the solvent may be protic or aprotic.

Organic solvent addition: In some instances, the disclosed hybridization buffer formulations may include the addition of an organic solvent. Examples of suitable solvents include, but are not limited to, acetonitrile, ethanol, DMF, and methanol, or any combination thereof at varying percentages (for example >5%). In some instances, the percentage of organic solvent (by volume) included in the hybridization buffer may range from about 1% to about 20%. In some instances, the percentage by volume of organic solvent may be at least 1%, at least 2%, at least 3%, at least 4%, at least 5%, at least 6%, at least 7%, at least 8%, at least 9%, at least 10%, at least 15%, or at least 20%. In some instances, the percentage by volume of organic solvent may be at most 20%, at most 15%, at most 10%, at most 9%, at most 8%, at most 7%, at most 6%, at most 5%, at most 4%, at most 3%, at most 2%, or at most 1%. Any of the lower and upper values described in this paragraph may be combined to form a range included within the present disclosure, for example, the percentage by volume of organic solvent may range from about 4% to about 15%. The percentage by volume of organic solvent may have any value within this range, e.g., about 7.5%.

When the organic solvent comprises a polar aprotic solvent, the amount of the polar aprotic solvent is present in an amount effective to denature a double stranded nucleic acid. In some embodiments, the amount of the polar aprotic solvent is greater than or equal to about 10% by volume based on the total volume of the formulation. The amount of the polar aprotic solvent is about or more than about 5%, 10%, 15%, 20%, 25%, 30%, 35%, 40%, 50%, 60%, 70%, 80%, 90%, or higher, by volume based on the total volume of the formulation. The amount of the polar aprotic solvent is lower than about 15%, 20%, 25%, 30%, 35%, 40%, 50%, 60%, 70%, 80%, 90%, or higher, by volume based on the total volume of the formulation. In some embodiments, the amount of the polar aprotic solvent is in the range of about 10% to 90% by volume based on the total volume of the formulation. In some embodiments, the amount of the polar aprotic solvent is in the range of about 25% to 75% by volume based on the total volume of the formulation. In some embodiments, the amount of the polar aprotic solvent is in the range of about 10% to 95%, 10% to 85%, 20% to 90%, 20% to 80%, 20% to 75%, or 30% to 60% by volume based on the total volume of the formulation.

When the organic solvent comprises a polar aprotic solvent, the amount of the aprotic solvent is present in an amount effective to denature a double stranded nucleic acid. In some embodiments, the amount of the aprotic solvent is greater than or equal to about 10% by volume based on the total volume of the formulation. The amount of the aprotic solvent is about or more than about 5%, 10%, 15%, 20%, 25%, 30%, 35%, 40%, 50%, 60%, 70%, 80%, 90%, or higher, by volume based on the total volume of the formulation. The amount of the aprotic solvent is lower than about 15%, 20%, 25%, 30%, 35%, 40%, 50%, 60%, 70%, 80%, 90%, or higher, by volume based on the total volume of the formulation. In some embodiments, the amount of the aprotic solvent is in the range of about 10% to 90% by volume based on the total volume of the formulation. In some embodiments, the amount of the aprotic solvent is in the range of about 25% to 75% by volume based on the total volume of the formulation. In some embodiments, the amount of the aprotic solvent is in the range of about 10% to 95%, 10% to 85%, 20% to 90%, 20% to 80%, 20% to 75%, or 30% to 60% by volume based on the total volume of the formulation.

Addition of molecular crowding volume exclusion agents: The composition described herein can include one or more crowding agents enhances molecular crowding. The crowding agent can be selected from the group consisting of polyethylene glycol (PEG), dextran, hydroxypropyl methyl cellulose (HPMC), hydroxyethyl methyl cellulose (HEMC), hydroxybutyl methyl cellulose, hydroxypropyl cellulose, methylcellulose, and hydroxyl methyl cellulose, and combination thereof. An example crowding agent may comprise one or more of polyethylene glycol (PEG), dextran, proteins, such as ovalbumin or hemoglobin, or Ficoll.

A suitable amount of a crowding agent in the composition allows for, enhances, or facilitates molecular crowding. The amount of the crowding agent is about or more than about 1%, 2%, 3%, 5%, 10%, 15%, 20%, 25%, 30%, 35%, 40%, 50%, 60%, or higher, by volume based on the total volume of the formulation. In some cases, the amount of the molecular crowding agent is greater than or equal to about 5% by volume based on the total volume of the formulation. The amount of the crowding agent is lower than about 3%, 5%, 10%, 12.5%, 15%, 20%, 25%, 30%, 35%, 40%, 50%, 60%, 70%, 80%, 90%, or higher, by volume based on the total volume of the formulation. In some cases, the amount of the molecular crowding agent can be less than or equal to about 30% by volume based on the total volume of the formulation. In some embodiments, the amount of the organic solvent is in the range of about 25% to 75% by volume based on the total volume of the formulation. In some embodiments, the amount of the organic solvent is in the range of about 1% to 40%, 1% to 35%, 2% to 50%, 2% to 40%, 2% to 35%, 2% to 30%, 2% to 25%, 2% to 20%, 2% to 10%, 5% to 50%, 5% to 40%, 5% to 35%, 5% to 30%, 5% to 25%, 5% to 20%, by volume based on the total volume of the formulation. In some cases, the amount of the molecular crowding agent can be in the range of about 5% to about 20% by volume based on the total volume of the formulation. In some embodiments, the amount of the crowding agent is in the range of about 1% to 30% by volume based on the total volume of the formulation.

One example of the crowding agent in the composition is polyethylene glycol (PEG. In some embodiments, the PEG used can have a molecular weight sufficient to enhance or facilitate molecular crowding. In some embodiments, the PEG used in the composition has a molecular weight in the range of about 5 k-50 k Da. In some embodiments, the PEG used in the composition has a molecular weight in the range of about 10 k-40 k Da. In some embodiments, the PEG used in the composition has a molecular weight in the range of about 10 k-30 k Da. In some embodiments, the PEG used in the composition has a molecular weight in the range of about 20 k Da.

In some instances, the disclosed hybridization buffer formulations may include the addition of a molecular crowding or volume exclusion agent. Molecular crowding or volume exclusion agents are, for example, macromolecules (e.g., proteins) which, when added to a solution in high concentrations, may alter the properties of other molecules in solution by reducing the volume of solvent available to the other molecules. In some instances, the percentage by volume of molecular crowding or volume exclusion agent included in the hybridization buffer formulation may range from about 1% to about 50%. In some instances, the percentage by volume of molecular crowding or volume exclusion agent may be at least 1%, at least 5%, at least 10%, at least 15%, at least 20%, at least 25%, at least 30%, at least 35%, at least 40%, at least 45%, or at least 50%. In some instances, the percentage by volume of molecular crowding or volume exclusion agent may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of molecular crowding or volume exclusion agent may range from about 5% to about 35%. The percentage by volume of molecular crowding or volume exclusion agent may have any value within this range, e.g., about 12.5%.

PH buffer system: The compositions described herein include pH buffer system that maintains the pH of the compositions in a range suitable for hybridization process. The pH buffer system can include one or more buffering agents selected from the group consisting of Tris, HEPES, TAPS, Tricine, Bicine, Bis-Tris, NaOH, KOH, TES, EPPS, MES, and MOPS. The pH buffer system can further include a solvent. An example pH buffer system includes MOPS, MES, TAPS, phosphate buffer combined with methanol, acetonitrile, ethanol, isopropanol, butanol, t-butyl alcohol, DMF, DMSO, or any combination therein The amount of the pH buffer system is effective to maintain the pH of the formulation to be in a range suitable for the hybridization. In some instances, the pH may be at least 3, at least 4, at least 5, at least 6, at least 7, at least 8, at least 9, or at least 10. In some instances, the pH may be at most 10, at most 9, at most 8, at most 7, at most 6, at most 5, at most 4, or at most 3. Any of the lower and upper values described in this paragraph may be combined to form a range included within the present disclosure, for example, the pH of the hybridization buffer may range from about 4 to about 8. The pH of the hybridization buffer may have any value within this range, e.g., about pH 7.8. In some cases, the pH range is about 3 to about 10. In some instances, the disclosed hybridization buffer formulations may include adjustment of pH over the range of about pH 3 to pH 10, with a narrower buffer range of 5-9.

Additives that impact DNA melting temperatures: The compositions described herein can include one or more additives to allow for better control of the melting temperature of the nucleic acid and enhance the stringency control of the hybridization reaction. Hybridization reactions are usually carried out under the stringent conditions in order to achieve hybridization specificity. In some cases, the additive for controlling melting temperature of nucleic acid is formamide.

The amount of the additive for controlling melting temperature of nucleic acid can vary depending on other agents used in the compositions. The amount of the additive for controlling melting temperature of the nucleic acid is about or more than about 1%, 2%, 3%, 5%, 10%, 15%, 20%, 25%, 30%, 35%, 40%, 50%, 60%, or higher, by volume based on the total volume of the formulation. In some cases, the amount of the additive for controlling melting temperature of the nucleic acid is greater than or equal to about 2% by volume based on the total volume of the formulation. In some cases, the amount of the additive for controlling melting temperature of the nucleic acid is greater than or equal to about 5% by volume based on the total volume of the formulation. In some cases, the amount of the additive for controlling melting temperature of the nucleic acid is lower than about 3%, 5%, 10%, 12.5%, 15%, 20%, 25%, 30%, 35%, 40%, 50%, 60%, 70%, 80%, 90%, or higher, by volume based on the total volume of the formulation. In some embodiments, the amount of the additive for controlling melting temperature of the nucleic acid is in the range of about 1% to 40%, 1% to 35%, 2% to 50%, 2% to 40%, 2% to 35%, 2% to 30%, 2% to 25%, 2% to 20%, 2% to 10%, 5% to 50%, 5% to 40%, 5% to 35%, 5% to 30%, 5% to 25%, 5% to 20%, by volume based on the total volume of the formulation. In some embodiments, the amount of the additive for controlling melting temperature of the nucleic acid is in the range of about 2% to 20% by volume based on the total volume of the formulation. In some cases, the amount of the additive for controlling melting temperature of the nucleic acid is in the range of about 5% to 10% by volume based on the total volume of the formulation.

In some instances, the disclosed hybridization buffer formulations may include the addition of an additive that alters nucleic acid duplex melting temperature. Examples of suitable additives that may be used to alter nucleic acid melting temperature include, but are not limited to, Formamide. In some instances, the percentage by volume of a melting temperature additive included in the hybridization buffer formulation may range from about 1% to about 50%. In some instances, the percentage by volume of a melting temperature additive may be at least 1%, at least 5%, at least 10%, at least 15%, at least 20%, at least 25%, at least 30%, at least 35%, at least 40%, at least 45%, or at least 50%. In some instances, the percentage by volume of a melting temperature additive may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of a melting temperature additive may range from about 10% to about 25%. The percentage by volume of a melting temperature additive may have any value within this range, e.g., about 22.5%.

Additives that impact DNA hydration: In some instances, the disclosed hybridization buffer formulations may include the addition of an additive that impacts nucleic acid hydration. Examples include, but are not limited to, betaine, urea, glycine betaine, or any combination thereof. In some instances, the percentage by volume of a hydration additive included in the hybridization buffer formulation may range from about 1% to about 50%. In some instances, the percentage by volume of a hydration additive may be at least 1%, at least 5%, at least 10%, at least 15%, at least 20%, at least 25%, at least 30%, at least 35%, at least 40%, at least 45%, or at least 50%. In some instances, the percentage by volume of a hydration additive may be at most 50%, at most 45%, at most 40%, at most 35%, at most 30%, at most 25%, at most 20%, at most 15%, at most 10%, at most 5%, or at most 1%. Any of the lower and upper values described in this paragraph may be combined to form a range included within the present disclosure, for example, the percentage by volume of a hydration additive may range from about 1% to about 30%. The percentage by volume of a melting temperature additive may have any value within this range, e.g., about 6.5%.

Nucleic Acid Hybridization Systems

Provided herein are systems comprising the hybridization compositions described herein and a low non-specific binding surface. The systems described herein, in some cases, comprise a flow cell device. Systems further comprise, in some cases, an imaging system (e.g., a camera and an inverted fluorescent microscope). Systems may further comprise one or more computer control system to perform computer-implemented methods of nucleic acid analysis.

Low non-specific binding surface: Disclosed herein includes a low non-specific binding surface that enable improved nucleic acid hybridization and amplification performance. In general, the disclosed surface may comprise one or more layers of a covalently or non-covalently attached low-binding, chemical modification layers, e.g., silane layers, polymer films, and one or more covalently or non-covalently attached primer sequences that may be used for tethering single-stranded template oligonucleotides to the surface. In some instances, the formulation of the surface, e.g., the chemical composition of one or more layers, the coupling chemistry used to cross-link the one or more layers to the surface, or, to each other, or to a combination thereof, and the total number of layers, may be varied such that non-specific binding of proteins, nucleic acid molecules, and other hybridization and amplification reaction components to the surface is minimized or reduced relative to a comparable monolayer. Often, the formulation of the surface may be varied such that non-specific hybridization on the surface is minimized or reduced relative to a comparable monolayer. The formulation of the surface may be varied such that non-specific amplification on the surface is minimized or reduced relative to a comparable monolayer. The formulation of the surface may be varied such that specific amplification rates, or, yields, or a combination thereof on the surface are maximized. Amplification levels suitable for detection are achieved in no more than 2, 3, 4, 5, 6, 7, 8, 9, 10, 15, or 30 amplification cycles in some cases disclosed herein.

Non-limiting examples of low non-specific binding surfaces is provided in U.S. Pat. Nos. 10,876,148 and 10,704,094, each of which is hereby incorporated by reference in its entirety. The terms, "low non-specific binding surface" and "low binding surface" are used interchangeably to refer to hydrophilic surfaces that exhibit a low amount of non-specific binding of proteins or nucleic acids, as compared with a surface that is not hydrophilic. In some instances the low non-specific binding surface is passivated, meaning it is coated with a substrate that is hydrophilic.

Examples of materials from which the substrate or support structure may be fabricated include, but are not limited to, glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The substrate or support structure may be rendered in any of a variety of geometries and dimensions, and may comprise any of a variety of materials. For example, in some instances the substrate or support structure may be locally planar (e.g., comprising a microscope slide or the surface of a microscope slide). Globally, the substrate or support structure may be cylindrical (e.g., comprising a capillary or the interior surface of a capillary), spherical (e.g., comprising the outer surface of a non-porous bead), or irregular (e.g., comprising the outer surface of an irregularly-shaped, non-porous bead or particle). In some instances, the surface of the substrate or support structure used for nucleic acid hybridization and amplification may be a solid, non-porous surface. In some instances, the surface of the substrate or support structure used for nucleic acid hybridization and amplification may be porous, such that the coatings described herein penetrate the porous surface, and nucleic acid hybridization and amplification reactions performed thereon may occur within the pores.

The substrate or support structure that comprises the one or more chemically-modified layers, e.g., layers of a low non-specific binding polymer, may be independent or integrated into another structure or assembly. For example, in some instances, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some embodiments, the substrate or support structure comprises the interior surface (such as the lumen surface) of a capillary. In alternate embodiments the substrate or support structure comprises the interior surface (such as the lumen surface) of a capillary etched into a planar chip.

The chemical modification layers may be applied uniformly across the surface of the substrate or support structure. Alternately, the surface of the substrate or support structure may be non-uniformly distributed or patterned, such that the chemical modification layers are confined to one or more discrete regions of the substrate. For example, the substrate surface may be patterned using photolithographic techniques to create an ordered array or random pattern of chemically-modified regions on the surface. The substrate surface may be patterned using contact printing, or, ink-jet printing techniques, or a combination thereof. In some instances, an ordered array or random patter of chemically-modified discrete regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions, or any intermediate number spanned by the range herein.

In order to achieve low non-specific binding surfaces (also referred to herein as "low binding" or "passivated" surfaces), hydrophilic polymers may be non-specifically adsorbed or covalently grafted to the substrate or support surface. For example, passivation can be performed utilizing poly(ethylene glycol) (PEG, also known as polyethylene oxide (PEO) or polyoxyethylene), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some instances, two or more layers of a hydrophilic polymer, e.g., a linear polymer, branched polymer, or multi-branched polymer, may be deposited on the surface. In some instances, two or more layers may be covalently coupled to each other or internally cross-linked to improve the stability of the resulting surface. In some instances, oligonucleotide primers with different base sequences and base modifications (or other biomolecules, e.g., enzymes or antibodies) may be tethered to the resulting surface layer at various surface densities. In some instances, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

As a result of the surface passivation techniques disclosed herein, proteins, nucleic acids, and other biomolecules do not "stick" to the substrates, that is, they exhibit low non-specific binding (non-specific binding). Examples are shown below using standard monolayer surface preparations with varying glass preparation conditions. Hydrophilic surface that have been passivated to achieve ultra-low non-specific binding for proteins and nucleic acids require novel reaction conditions to improve primer deposition reaction efficiencies, hybridization performance, and induce effective amplification. All of these processes require oligonucleotide attachment and subsequent protein binding and delivery to a low binding surface. As described below, the combination of a new primer surface conjugation formulation (Cy3 oligonucleotide graft titration) and resulting ultra-low non-specific background (non-specific binding functional tests performed using red and green fluorescent dyes) yielded results that demonstrate the viability of the disclosed approaches. Some surfaces disclosed herein exhibit a ratio of specific (e.g., hybridization to a tethered primer or probe) to non-specific binding (e.g., $B_{inter}$) of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to non-specific fluorescence signal (e.g., for specifically-hybridized to non-specifically bound labeled oligonucleotides, or for specifically-amplified to non-specifically-bound ($B_{inter}$) or non-specifically amplified ($B_{intra}$) labeled oligonucleotides or a combination thereof ($B_{inter}$+$B_{intra}$)) for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

In order to scale primer surface density and add additional dimensionality to hydrophilic or amphoteric surfaces, substrates comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some instances, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high primer density materials may be constructed in solution and subsequently layered onto the surface in multiple operations.

The attachment chemistry used to graft a first chemically-modified layer to a support surface will generally be dependent on both the material from which the support is fabricated and the chemical nature of the layer. In some instances, the first layer may be covalently attached to the support surface. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques may be used to clean or treat the support surface. For example, glass or silicon surfaces may be acid-washed using a Piranha solution (a mixture of sulfuric acid ($H_2SO_4$) and hydrogen peroxide ($H_2O_2$)), or, cleaned using an oxygen plasma treatment method, or a combination thereof.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding support surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (e.g., comprising a free amino functional group), maleimide-PEG silane, biotin-PEG silane, and the like.

Any of a variety of molecules including, but not limited to, amino acids, peptides, nucleotides, oligonucleotides, other monomers or polymers, or combinations thereof may be used in creating the one or more chemically-modified layers on the support surface, where the choice of components used may be varied to alter one or more properties of the support surface, e.g., the surface density of functional groups, or, tethered oligonucleotide primers, or combination thereof, the hydrophilicity/hydrophobicity of the support surface, or the three three-dimensional nature (e.g., "thickness") of the support surface. Examples of polymers that may be used to create one or more layers of low non-specific binding material in any of the disclosed support surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the support surface, or, to cross-link the layers to each other, or a combination thereof include, but are not limited to, biotin-streptavidin interactions (or variations thereof), his tag-Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches. Molecules often exhibit a 'power of 2' number of branches, such as 2, 4, 8, 16, 32, 64, or 128 branches.

PEG multilayers include PEG (8, 16, 8) on PEG-amine-APTES, exposed to two layers of 7 uM primer pre-loading, exhibited a concentration of 2,000,000 to 10,000,000 on the surface. Similar concentrations were observed for 3-layer multi-arm PEG (8, 16, 8) and (8, 64, 8) on PEG-amine-APTES exposed to 8 uM primer, and 3-layer multi-arm PEG (8, 8, 8) using star-shape PEG-amine to replace dumbbell-shaped 16mer and 64mer. PEG multilayers having comparable first, second and third PEG level are also contemplated.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some instances, e.g., wherein at least one layer of a multi-layered surface comprises a branched polymer, the number of covalent bonds between a branched polymer molecule of the layer being deposited and molecules of the underlying layer may range from about one covalent linkage per molecule and about 32 covalent linkages per molecule. In some instances, the number of covalent bonds between a branched polymer molecule of the new layer and molecules of the underlying layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 or more than 32 covalent linkages per molecule.

Any reactive functional groups that remain following the coupling of a material layer to the support surface may optionally be blocked by coupling a small, inert molecule using a high yield coupling chemistry. For example, in the case that amine coupling chemistry is used to attach a new material layer to the underlying one, any residual amine groups may subsequently be acetylated or deactivated by coupling with a small amino acid such as glycine.

The number of layers of low non-specific binding material, e.g., a hydrophilic polymer material, deposited on the surface of the disclosed low binding supports may range from 1 to about 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials. In some instances at least one layer may comprise a branched polymer. In some instance, all of the layers may comprise a branched polymer.

One or more layers of low non-specific binding material may in some cases be deposited on, or, conjugated to the substrate surface, or a combination thereof, using a polar protic solvent, a polar aprotic solvent, a nonpolar solvent, or any combination thereof. In some instances the solvent used for layer deposition, or, coupling, or a combination thereof may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some instances, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of water or an aqueous buffer solution. In some instances, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of an organic solvent. The pH of the solvent mixture used may be less than or equal to about 5, 5, 5, 5, 6, 6, 6.5, 7, 7.5, 8, 8.5, 9, 9.5, 10, or any value spanned or adjacent to the range described herein. The pH of the solvent mixture may be greater than or equal to about 10.

In some instances, one or more layers of low non-specific binding material may be deposited on, or, conjugated to the substrate surface, or a combination thereof, using a mixture of organic solvents, wherein the dielectric constant of at least once component is less than 40 and constitutes at least 50% of the total mixture by volume. In some instances, the dielectric constant of the at least one component may be less than 10, less than 20, less than 30, less than 40. In some instances, the at least one component constitutes at least 20%, at least 30%, at least 40%, at least 50%, at least 50%, at least 60%, at least 70%, or at least 80% of the total mixture by volume.

As noted, the low non-specific binding supports of the present disclosure exhibit reduced non-specific binding of proteins, nucleic acids, and other components of the hybridization, or, amplification formulation, or a combination thereof, used for solid-phase nucleic acid amplification. The degree of non-specific binding exhibited by a given support surface may be assessed either qualitatively or quantitatively. For example, in some instances, exposure of the surface to fluorescent dyes (e.g., Cy3, Cy5, etc.), fluorescently-labeled nucleotides, fluorescently-labeled oligonucleotides, or, fluorescently-labeled proteins (e.g. polymerases), or a combination thereof, under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, or, fluorescently-labeled proteins (e.g. polymerases), or a combination thereof, under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation, or, self-quenching of the fluorophore, or a combination thereof, is not an issue) and suitable calibration standards are used. In some instances, other techniques, for example, radioisotope labeling and counting methods may be used for quantitative assessment of the degree to which non-specific binding is exhibited by the different support surface formulations of the present disclosure.

Some surfaces disclosed herein exhibit a ratio of specific to non-specific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to non-specific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some instances, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label. In some instances, the degree of non-specific binding exhibited by a given support surface formulation may thus be assessed in terms of the number of non-specifically bound protein molecules (or other molecules) per unit area. In some instances, the low-binding supports of the present disclosure may exhibit non-specific protein binding (or non-specific binding of other specified molecules, e.g., Cy3 dye) of less than or equal to about 0.001 molecule per $\mu m^2$, less than or equal to about 0.01 molecule per $\mu m^2$, less than or equal to about 0.1 molecule per $\mu m^2$, less than or equal to about 0.25 molecule per $\mu m^2$, less than or equal to about 0.5 molecule per $\mu m^2$, less than or equal to about 1 molecule per $\mu m^2$, less than or equal to about 10 molecules per $\mu m^2$, less than or equal to about 100 molecules per $\mu m^2$, or less than or equal to about 1,000 molecules per $\mu m^2$. A given support surface of the present disclosure may exhibit non-specific binding falling anywhere within this range, for example, of less than 86 molecules per $\mu m^2$.

In some instances, the surfaces disclosed herein exhibit a ratio of specific to non-specific binding of a fluorophore such as Cy3 of at least or equal to about 2, 3, 4, 5, 6, 7, 8, 9, 10, 11, 12, 13, 14, 15, 16, 17, 18, 19, 20, 25, 30, 35, 40, 50, 75, 100, or any intermediate value spanned by the range herein. In some instances, the surfaces disclosed herein exhibit a ratio of specific to non-specific binding of fluorophore such as Cy3 of greater than or equal to about 100. In some instances, the surfaces disclosed herein exhibit a ratio of specific to non-specific fluorescence signals for a fluorophore such as Cy3 of at least or equal to about 2, 3, 4, 5, 6, 7, 8, 9, 10, 11, 12, 13, 14, 15, 16, 17, 18, 19, 20, 25, 30, 35, 40, 50, 75, 100, or any intermediate value spanned by the range herein. In some instances, the surfaces disclosed herein exhibit a ratio of specific to non-specific fluorescence signals for a fluorophore such as Cy3 of greater than or equal to about 100.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule non-specifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surfaced disclosed herein may range from about 0 degrees to about 30 degrees. In some instances, the water contact angle for the hydrophilic, low-binding support surfaced disclosed herein may no more than 50 degrees, 45 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. A given hydrophilic, low-binding support surface of the present disclosure may exhibit a water contact angle having a value of anywhere within this range.

In some instances, the hydrophilic surfaces disclosed herein facilitate reduced wash times for bioassays, often due to reduced non-specific binding of biomolecules to the low-binding surfaces. In some instances, adequate washes may be performed in less than or equal to about 60, 50, 40, 30, 20, 15, 10, or less than 10 seconds. For example, in some instances adequate washes may be performed in less than 30 seconds.

Some low-binding surfaces of the present disclosure exhibit significant improvement in stability or durability to prolonged exposure to solvents and elevated temperatures, or to repeated cycles of solvent exposure or changes in temperature. For example, in some instances, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some instances, the degree of change in the fluorescence used to assess the quality of the surface may be less than or equal to about 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents, or, elevated temperatures, or a combination thereof (or any combination of these percentages as measured over these time periods). In some instances, the degree of change in the fluorescence used to assess the quality of the surface may be less than or equal to about 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes, or changes in temperature, or a combination thereof (or any combination of these percentages as measured over this range of cycles).

In some instances, the surfaces disclosed herein may exhibit a high ratio of specific signal to non-specific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface.

Fluorescence excitation energies vary among particular fluorophores and protocols, and may range in excitation wavelength, consistent with fluorophore selection or other parameters of use of a surface disclosed herein. In some instances, the wavelength is less than or equal to about 400 nanometers (nm). In some instances, the wavelength is more than or equal to about 800 nm. In some instances, the wavelength is between 400 nm and 800 nm.

Accordingly, low background surfaces as disclosed herein exhibit low background fluorescence signals or high contrast to noise (CNR) ratios. For example, in some instances, the background fluorescence of the surface at a location that is spatially distinct or removed from a labeled feature on the surface (e.g., a labeled spot, cluster, discrete region, subsection, or subset of the surface) comprising a hybridized cluster of nucleic acid molecules, or a clonally-amplified cluster of nucleic acid molecules produced by 20 cycles of nucleic acid amplification via thermocycling, may be no more than 20×, 10×, 5×, 2×, 1×, 0.5×, 0.1×, or less than 0.1× greater than the background fluorescence measured at that same location prior to performing said hybridization or said 20 cycles of nucleic acid amplification.

In some instances, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

The surface that comprises the one or more chemically-modified layers, e.g., layers of a low non-specific binding polymer, may be independent or integrated into another structure or assembly. The chemical modification layers may be applied uniformly across the surface. Alternately, the surface may be patterned, such that the chemical modification layers are confined to one or more discrete regions of the substrate. For example, the surface may be patterned using photolithographic techniques to create an ordered array or random pattern of chemically-modified regions on the surface. The substrate surface may be patterned using, e.g., contact printing, or, ink-jet printing techniques, or a combination thereof. In some instances, an ordered array or random patter of chemically-modified regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions.

In order to achieve low non-specific binding surfaces (also referred to herein as "low binding" or "passivated" surfaces), hydrophilic polymers may be non-specifically adsorbed or covalently grafted to the surface. For example, passivation can be performed utilizing poly(ethylene glycol)

(PEG, also known as polyethylene oxide (PEO) or polyoxyethylene) or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some instances, two or more layers of a hydrophilic polymer, e.g., a linear polymer, branched polymer, or multi-branched polymer, may be deposited on the surface. In some instances, two or more layers may be covalently coupled to each other or internally cross-linked to improve the stability of the resulting surface. In some instances, oligonucleotide primers with different base sequences and base modifications (or other biomolecules, e.g., enzymes or antibodies) may be tethered to the resulting surface layer at various surface densities. In some instances, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

In order to scale primer surface density and add additional dimensionality to hydrophilic or amphoteric surfaces, surfaces comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer sub-units such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some instances, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high primer density materials may be constructed in solution and subsequently layered onto the surface.

The attachment chemistry used to graft a first chemically-modified layer to a surface will generally be dependent on both the material from which the surface is fabricated and the chemical nature of the layer. In some instances, the first layer may be covalently attached to the surface. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques may be used to clean or treat the surface. For example, glass or silicon surfaces may be acid-washed using a Piranha solution (a mixture of sulfuric acid ($H_2SO_4$) and hydrogen peroxide ($H_2O_2$)), base treatment in KOH and NaOH, or, cleaned using an oxygen plasma treatment method, or a combination thereof.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (e.g., comprising a free amino functional group), maleimide-PEG silane, biotin-PEG silane, and the like.

Any of a variety of molecules including, but not limited to, amino acids, peptides, nucleotides, oligonucleotides, other monomers or polymers, or combinations thereof may be used in creating the one or more chemically-modified layers on the surface, where the choice of components used may be varied to alter one or more properties of the surface, e.g., the surface density of functional groups, or, tethered oligonucleotide primers, or a combination thereof; the hydrophilicity/hydrophobicity of the surface, or the three three-dimensional nature (e.g., "thickness") of the surface. Examples of polymers that may be used to create one or more layers of low non-specific binding material in any of the disclosed surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the surface, or, to cross-link the layers to each other, or a combination thereof include, but are not limited to, biotin-streptavidin interactions (or variations thereof), his tag-Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches.

Linear, branched, or multi-branched polymers used to create one or more layers of any of the multi-layered surfaces disclosed herein may have a molecular weight of at least 500, at least 1,000, at least 2,000, at least 3,000, at least 4,000, at least 5,000, at least 10,000, at least 15,000, at least 20,000, at least 25,000, at least 30,000, at least 35,000, at least 40,000, at least 45,000, or at least 50,000 daltons.

In some instances, e.g., wherein at least one layer of a multi-layered surface comprises a branched polymer, the number of covalent bonds between a branched polymer molecule of the layer being deposited and molecules of the underlying layer may range from about one covalent linkages per molecule and about 32 covalent linkages per molecule. In some instances, the number of covalent bonds between a branched polymer molecule of the new layer and molecules of the underlaying layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32 covalent linkages per molecule.

Any reactive functional groups that remain following the coupling of a material layer to the surface may optionally be blocked by coupling a small, inert molecule using a high yield coupling chemistry. For example, in the case that amine coupling chemistry is used to attach a new material layer to the underlying one, any residual amine groups may subsequently be acetylated or deactivated by coupling with a small amino acid such as glycine.

The number of layers of low non-specific binding material, e.g., a hydrophilic polymer material, deposited on the surface, may range from 1 to about 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials. In some instances at least one layer may comprise a branched polymer. In some instance, all of the layers may comprise a branched polymer.

One or more layers of low non-specific binding material may in some cases be deposited on, or, conjugated to the substrate surface, or a combination thereof using a polar protic solvent, an organic solvent, a nonpolar solvent, or any combination thereof. In some instances the solvent used for layer deposition, or, coupling, or a combination thereof may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some instances, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of water or an aqueous buffer solution. In some instances, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, with the balance made up of an organic solvent. The pH of the solvent mixture used may be less than or equal to about 6, about 6, 6.5, 7, 7.5, 8, 8.5, or 9. The pH of the solvent mixture used may be greater than or equal to about 9.

As noted, the low non-specific binding surface exhibit reduced non-specific binding of nucleic acids, and other components of the hybridization, or, amplification formulation, or a combination thereof used for solid-phase nucleic acid amplification. The degree of non-specific binding exhibited by a given surface may be assessed either qualitatively or quantitatively. For example, in some instances, exposure of the surface to fluorescent dyes (e.g., Cy3, Cy5, etc.), fluorescently-labeled nucleotides, fluorescently-labeled oligonucleotides, or, fluorescently-labeled proteins (e.g. polymerases), or a combination thereof under a standardized set of conditions, followed by a specified rinse protocol and fluorescence imaging may be used as a qualitative tool for comparison of non-specific binding surface comprising different surface formulations. In some instances, exposure of the surface to fluorescent dyes, fluorescently-labeled nucleotides, fluorescently-labeled oligonucleotides, or, fluorescently-labeled proteins (e.g. polymerases), or combination thereof under a standardized set of conditions, followed by a specified rinse protocol and fluorescence imaging may be used as a quantitative tool for comparison of non-specific binding on surfaces comprising different surface formulations—provided that care has been taken to ensure that the fluorescence imaging is performed under conditions where fluorescence signal is linearly related (or related in a predictable manner) to the number of fluorophores on the surface (e.g., under conditions where signal saturation, or, self-quenching of the fluorophore, or a combination thereof is not an issue) and suitable calibration standards are used. In some instances, other techniques, for example, radioisotope labeling and counting methods may be used for quantitative assessment of the degree to which non-specific binding is exhibited by the different surface formulations of the present disclosure.

As noted, in some instances, the degree of non-specific binding exhibited by the disclosed low-binding surfaces may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label. In some instances, the degree of non-specific binding exhibited by a given surface formulation may thus be assessed in terms of the number of non-specifically bound protein molecules (or other molecules) per unit area. In some instances, the low-binding surfaces of the present disclosure may exhibit non-specific protein binding (or non-specific binding of other specified molecules, e.g., Cy3 dye) of less than or equal to about 0.001 molecule per $\mu m^2$, less than or equal to about 0.01 molecule per $\mu m^2$, less than or equal to about 0.1 molecule per $\mu m^2$, less than or equal to about 0.25 molecule per $\mu m^2$, less than or equal to about 0.5 molecule per $\mu m^2$, less than or equal to about 1 molecule per $\mu m^2$, less than or equal to about 10 molecules per $\mu m^2$, less than or equal to about 100 molecules per $\mu m^2$, or less than or equal to about 1,000 molecules per $\mu m^2$. A given surface of the present disclosure may exhibit non-specific binding falling anywhere within this range, for example, of less than or equal to about 86 molecules per $\mu m^2$. For example, some modified surfaces disclosed herein exhibit non-specific protein binding of less than or equal to about 0.5 molecule/$\mu m^2$ following contact with a 1 $\mu M$ solution of bovine serum albumin (BSA) in phosphate buffered saline (PBS) buffer for 30 minutes, followed by a 10 minute PBS rinse. In another example, some modified surfaces disclosed herein exhibit non-specific protein binding of less than or equal to about 0.5 molecule/$\mu m^2$ following contact with a 1 $\mu M$ solution of Cyanine 3 dye-labeled streptavidin (GE Amersham) in phosphate buffered saline (PBS) buffer for 15 minutes, followed by 3 rinses with deionized water. Some modified surfaces disclosed herein exhibit non-specific binding of Cy3 dye molecules of less than or equal to about 0.25 molecules per $\mu m^2$.

The low-background surfaces consistent with the disclosure herein may exhibit specific dye attachment (e.g., Cy3 attachment) to non-specific dye adsorption (e.g., Cy3 dye adsorption) ratios of at least 4:1, 5:1, 6:1, 7:1, 8:1, 9:1, 10:1, 15:1, 20:1, 30:1, 40:1, 50:1, or more than 50 specific dye molecules attached per molecule non-specifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding surfaces disclosed herein may range from about 0 degrees to about 30 degrees. In some instances, the water contact angle for the hydrophilic, low-binding surfaced disclosed herein may no more than 50 degrees, 40 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than 40 degrees. A given hydrophilic, low-binding surface of the present disclosure may exhibit a water contact angle having a value of anywhere within this range.

In some instances, the low-binding surfaces of the present disclosure may exhibit significant improvement in stability or durability to prolonged exposure to solvents and elevated temperatures, or to repeated cycles of solvent exposure or changes in temperature. For example, in some instances, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some instances, the degree of change in the fluorescence used to assess the quality of the surface may be less than or equal to about 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents, or, elevated temperatures, or a combination thereof (or any combination of these percentages as measured over these time periods). In some instances, the degree of change in the fluorescence used to assess the quality of the surface may be less than or equal to about 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes, or, changes in temperature, or a combination thereof (or any combination of these percentages as measured over this range of cycles).

In some instances, the surfaces disclosed herein may exhibit a high ratio of specific signal to non-specific signal or other background. For example, when used for nucleic acid amplification, some surfaces may exhibit an amplification signal that is at least 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 4, 5, 6, 7, 8, 9, 10, 15, 20, 30, 40, 50, 75, 100, or greater than 100 fold greater than a signal of an adjacent amplified nucleic acid population region of the surface.

Accordingly, low background surfaces as disclosed herein exhibit low background fluorescence signals or high contrast to noise (CNR) ratios.

Flow Cell Devices: The low non-specific binding surfaces, in some aspects, are surfaces of a flow device described herein. Flow devices described herein can include a first reservoir housing a first solution and having an inlet end and an outlet end, wherein the first agent flows from the inlet end to the outlet end in the first reservoir; a second reservoir housing a second solution and having an inlet end and an outlet end, wherein the second agent flows from the inlet end to the outlet end in the second reservoir; a central region having an inlet end fluidically coupled to the outlet end of the first reservoir and the outlet end of the second reservoir through at least one valve. In the flow cell device, the volume of the first solution flowing from the outlet of the first reservoir to the inlet of the central region is less than the volume of the second solution flowing from the outlet of the second reservoir to the inlet of the central region.

The reservoirs described in the device can be used to house different reagents. In some aspects, the first solution housed in the first reservoir is different from the second solution that is housed in the second reservoir. The second solution comprises at least one reagent common to a plurality of reactions occurring in the central region. In some aspects, the second solution comprises at least one reagent selected from the list consisting of a solvent, a polymerase, and a dNTP. In some aspects, the second solution comprise low cost reagents. In some aspects, the first reservoir is fluidically coupled to the central region through a first valve and the second reservoir is fluidically coupled to the central region through a second valve. The valve can be a diaphragm valve or other suitable valves.

The central region can include a capillary tube or microfluidic chip having one or more microfluidic channels. In some embodiments, the capillary tube is an off-shelf product. The capillary tube or the microfluidic chip can also be removable from the device. In some embodiments, the capillary tube or microfluidic channel comprises an oligonucleotide population directed to sequence a eukaryotic genome. In some embodiments, the capillary tube or microfluidic channel in the central region can be removable.

Disclosed herein are single capillary flow cell devices that comprise a single capillary and one or two fluidic adapters affixed to one or both ends of the capillary, where the capillary provides a fluid flow channel of specified cross-sectional area and length, and where the fluidic adapters are configured to mate with standard tubing to provide for convenient, interchangeable fluid connections with an external fluid flow control system. In general, the capillary used in the disclosed flow cell devices (and flow cell cartridges to be described below) will have at least one internal, axially-aligned fluid flow channel (or "lumen") that runs the full length of the capillary. In some aspects, the capillary may have two, three, four, five, or more than five internal, axially-aligned fluid flow channels (or "lumen").

A number specified cross-sectional geometries for a single capillary (or lumen thereof) are consistent with the disclosure herein, including, but not limited to, circular, elliptical, square, rectangular, triangular, rounded square, rounded rectangular, or rounded triangular cross-sectional geometries. In some aspects, the single capillary (or lumen thereof) may have any specified cross-sectional dimension or set of dimensions. For example, in some aspects the largest cross-sectional dimension of the capillary lumen (e.g. the diameter if the lumen is circular in shape or the diagonal if the lumen is square or rectangular in shape) may range from about 10 μm to about 10 mm. The length of the one or more capillaries used to fabricate the disclosed single capillary flow cell devices or flow cell cartridges may range from about 5 mm to about 5 cm or greater. Capillaries in some cases have a gap height of about or exactly 50, 75, 100, 125, 150, 175, 200, 225, 250, 275, 300, 350, 400, or 500 μm, or any value falling within the range defined thereby.

Disclosed herein also include flow cell devices that comprise one or more microfluidic chips and one or two fluidic adapters affixed to one or both ends of the microfluidic chips, where the microfluidic chip provides one or more fluid flow channels of specified cross-sectional area and length, and where the fluidic adapters are configured to mate with the microfluidic chip to provide for convenient, interchangeable fluid connections with an external fluid flow control system.

The microfluidic chip described herein includes one or more microfluidic channels etched on the surface of the chip. The microfluidic channels are defined as fluid conduits with at least one minimum dimension from <1 nm to 1000 μm. The microfluidic channel system, fabricated on either a glass or silicon substrate, has channel heights and widths on the order of <1 nm to 1000 μm. The channel length can be in the micrometer range.

The capillaries or microfluidic chip used for constructing the disclosed flow cell devices may be fabricated from any of a variety of materials known to those of skill in the art including, but not limited to, glass (e.g., borosilicate glass, soda lime glass, etc.), fused silica (quartz), polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET), polydimethylsiloxane (PDMS), etc.), polyetherimide (PEI) and perfluoroelastomer (FFKM) as more chemically inert alternatives. PEI is somewhere between polycarbonate and PEEK in terms of both cost and compatibility. FFKM is also known as Kalrez or any combination thereof.

The flow cell device (e.g., microfluidic chip or capillary flow cell) is operatively coupled to an imaging systems described herein to capture or detect signals of DNA bases, for applications such as nucleic acid sequencing, analyte capture and detection, and the like.

Oligonucleotide primers and adapter sequences: In general, at least one layer of the one or more layers of low non-specific binding material may comprise functional groups for covalently or non-covalently attaching oligonucleotide adapter or primer sequences, or the at least one layer may already comprise covalently or non-covalently attached oligonucleotide adapter or primer sequences at the time that it is deposited on the support surface. In some instances, the oligonucleotides tethered to the polymer molecules of at least one third layer may be distributed at a plurality of depths throughout the layer.

One or more types of oligonucleotide primer may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, or, molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

In some instances, the tethered oligonucleotide adapter, or, primer sequences, or a combination thereof may range in length from about 10 nucleotides to about 100 nucleotides. In some instances, the tethered oligonucleotide adapter, or, primer sequences, or a combination thereof may be at least 10, at least 20, at least 30, at least 40, at least 50, at least 60, at least 70, at least 80, at least 90, or at least 100 nucleotides in length. In some instances, the tethered oligonucleotide adapter, or, primer sequences, or a combination thereof may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter, or, primer sequences, or combination thereof may range from about 20 nucleotides to about 80 nucleotides. The length of the tethered oligonucleotide adapter, or, primer sequences, or combination thereof may have any value within this range, e.g., about 24 nucleotides.

In some instances, the tethered primer sequences may comprise modifications designed to facilitate the specificity and efficiency of nucleic acid amplification as performed on the low-binding supports. For example, in some instances the primer may comprise polymerase stop points such that the stretch of primer sequence between the surface conjugation point and the modification site is always in single-stranded form and functions as a loading site for 5' to 3' helicases in some helicase-dependent isothermal amplification methods. Other examples of primer modifications that may be used to create polymerase stop points include, but are not limited to, an insertion of a PEG chain into the backbone of the primer between two nucleotides towards the 5' end, insertion of an abasic nucleotide (e.g., a nucleotide that has neither a purine nor a pyrimidine base), or a lesion site which can be bypassed by the helicase.

As will be discussed further in the examples below, the surface density of tethered primers on the support surface, or, the spacing of the tethered primers away from the support surface (e.g., by varying the length of a linker molecule used to tether the primers to the surface), or a combination thereof, may be varied in order to "tune" the support for optimal performance when using a given amplification method. As noted below, adjusting the surface density of tethered primers may impact the level of specific, or, non-specific amplification, or a combination thereof, observed on the support in a manner that varies according to the amplification method selected. In some instances, the surface density of tethered oligonucleotide primers may be varied by adjusting the ratio of molecular components used to create the support surface. For example, in the case that an oligonucleotide primer-PEG conjugate is used to create the final layer of a low-binding support, the ratio of the oligonucleotide primer-PEG conjugate to a non-conjugated PEG molecule may be varied. The resulting surface density of tethered primer molecules may then be estimated or measured using any of a variety of techniques. Examples include, but are not limited to, the use of radioisotope labeling and counting methods, covalent coupling of a cleavable molecule that comprises an optically-detectable tag (e.g., a fluorescent tag) that may be cleaved from a support surface of defined area, collected in a fixed volume of an appropriate solvent, and then quantified by comparison of fluorescence signals to that for a calibration solution of known optical tag concentration, or using fluorescence imaging techniques provided that care has been taken with the labeling reaction conditions and image acquisition settings to ensure that the fluorescence signals are linearly related to the number of fluorophores on the surface (e.g., that there is no significant self-quenching of the fluorophores on the surface).

In some instances, the resultant surface density of oligonucleotide primers on the low binding support surfaces of the present disclosure may range from about 1,000 primer molecules per $\mu m^2$ to about 1,000,000 primer molecules per $\mu m^2$. In some instances, the surface density of oligonucleotide primers may be at least 1,000, at least 10,000, at least 100,000, or at least 1,000,000 molecules per $\mu m^2$. In some instances, the surface density of oligonucleotide primers may be at most 1,000,000, at most 100,000, at most 10,000, or at most 1,000 molecules per $\mu m^2$. Any of the lower and upper values described in this paragraph may be combined to form a range included within the present disclosure, for example, in some instances the surface density of primers may range from about 10,000 molecules per $\mu m^2$ to about 100,000 molecules per $\mu m^2$. The surface density of primer molecules may have any value within this range, e.g., about 455,000 molecules per $\mu m^2$. In some instances, the surface density of template library nucleic acid sequences initially hybridized to adapter or primer sequences on the support surface may be less than or equal to that indicated for the surface density of tethered oligonucleotide primers. In some instances, the surface density of clonally-amplified template library nucleic acid sequences hybridized to adapter or primer sequences on the support surface may span the same range as that indicated for the surface density of tethered oligonucleotide primers.

Local densities as listed above do not preclude variation in density across a surface, such that a surface may comprise a region having an oligo density of, for example, 500,000 per $um^2$, while also comprising at least a second region having a substantially different local density.

Imaging Systems. Imaging systems described herein are utilized to detect hybridization between one or more sample nucleic acid molecules and capture nucleic acid molecules coupled to a low non-specific binding surface. In some cases, the imaging systems comprise a camera. In some cases, the imaging systems comprise a microscope, such as a fluorescence microscope. An inverted fluorescence microscope in combination with a camera may be used to capture an image of the low non-specific binding surface and visualize hybridization between one or more sample nucleic acid molecules and capture nucleic acid molecules. A non-limiting example of an imaging system described herein is an Olympus IX83 microscope (Olympus Corp., Center Valley, PA) with a total internal reflectance fluorescence (TTRF) objective (100×, 1.5 NA, Olympus), a CCD camera (e.g., an Olympus EM-CCD monochrome camera, Olympus XM-10 monochrome camera, or an Olympus DP80 color and monochrome camera), an illumination source (e.g., an Olympus 100 W Hg lamp, an Olympus 75 W Xe lamp, or an Olympus U-HGLGPS fluorescence light source), and excitation wavelengths of 532 nm or 635 nm. Dichroic mirrors were purchased from Semrock (IDEX Health & Science, LLC, Rochester, New York), e.g., 405, 488, 532, or 633 nm dichroic reflectors/beamsplitters, and band pass filters were chosen as 532 LP or 645 LP concordant with the appropriate excitation wavelength.

Figure 12:
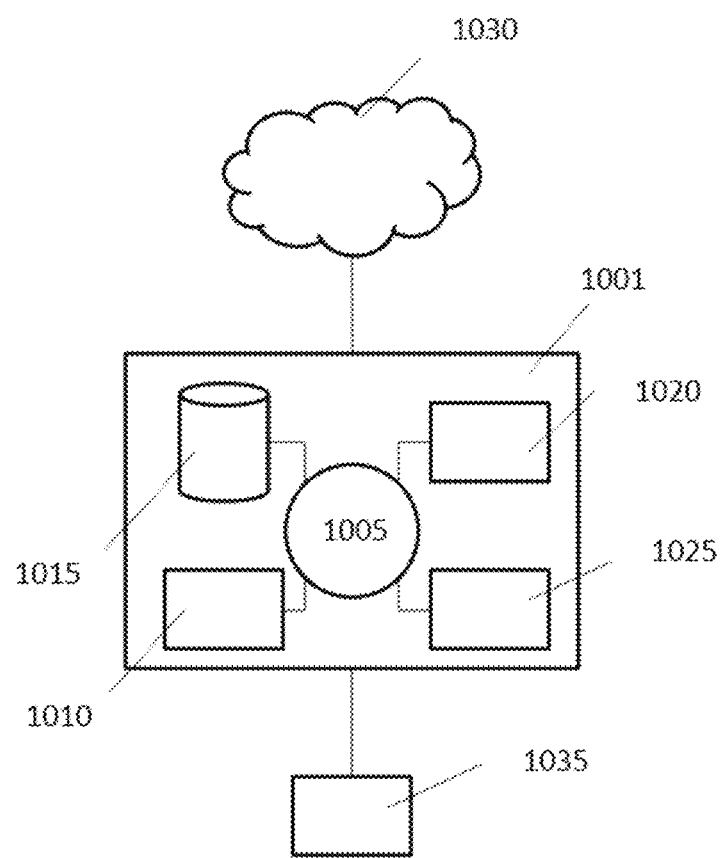
FIG. 12 schematically depicts an example computer control system.

Computer Control Systems. The present disclosure provides computer systems that are programmed or otherwise configured to implement methods provided herein, such as, for example, methods for nucleic sequencing, storing reference nucleic acid sequences, conducting sequence analysis and/or comparing sample and reference nucleic acid sequences as described herein. An example of such a computer system is shown in FIG. 12. As shown in FIG. 12, the computer system 1001 includes a central processing unit (CPU, also "processor" and "computer processor" herein) 1005, which can be a single core or multi core processor, or a plurality of processors for parallel processing. The computer system 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The computer system 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the computer system 1001, can implement a peer-to-peer network, which may enable devices coupled to the computer system 1001 to behave as a client or a server.

The CPU 1005 can execute a sequence of machine-readable instructions, which can be embodied in a program or software. The instructions may be stored in a memory location, such as the memory 1010. Examples of operations performed by the CPU 1005 can include fetch, decode, execute, and writeback.

The storage unit 1015 can store files, such as drivers, libraries and saved programs. The storage unit 1015 can store user data, e.g., user preferences and user programs. The computer system 1001 in some cases can include one or more additional data storage units that are external to the computer system 1001, such as located on a remote server that is in communication with the computer system 1001 through an intranet or the Internet.

The computer system 1001 can communicate with one or more remote computer systems through the network 1030. For instance, the computer system 1001 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1001 via the network 1030.

Methods as described herein can be implemented by way of machine (e.g., computer processor) executable code stored on an electronic storage location of the computer system 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1001, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1001 can include or be in communication with an electronic display 1035 that comprises a user interface (UI) for providing, for example, an output or readout of a nucleic acid sequencing instrument coupled to the computer system 1001. Such readout can include a nucleic acid sequencing readout, such as a sequence of nucleic acid bases that comprise a given nucleic acid sample. The UI may also be used to display the results of an analysis making use of such readout. Examples of UI's include, without limitation, a graphical user interface (GUI) and web-based user interface. The electronic display 1035 can be a computer monitor, or a capacitive or resistive touchscreen.

Hybridization Performance of Compositions and Systems

Improvements in hybridization rate: In some instances, the use of the buffer formulations disclosed herein (optionally, used in combination with low non-specific binding surface) yield relative hybridization rates that range from about 2× to about 20× faster than that for a standard hybridization protocol. In some instances, the relative hybridization rate may be at least 2×, at least 3×, at least 4×, at least 5×, at least 6×, at least 7×, at least 8×, at least 9×, at least 10×, at least 12×, at least 14×, at least 16×, at least 18×, or at least 20× that for a standard hybridization protocol.

The method and composition described herein can help shorten the time required for completing hybridization. In some embodiments, the hybridization time can be in the range of about 1 seconds (s) to 2 hours (h), about 5 s to 1.5 h, about 15 s to 1 h, or about 15 s to 0.5 h. In some embodiments, the hybridization time can be in the range of about 15 s to 1 h. In some embodiments, the hybridization time can be shorter than 15 s, 30 s, 1 minutes (min), 1.5 min, 2 min, 2.5 min, 3 min, 4 min, 5 min, 6 min, 7 min, 8 min, 9 min, 10 min, 15 min, 20 min, 25 min, 30 min, 40 min, 50 min, 60 min, 70 min, 80 min, 90 min, 100 min, 110 min, or 120 min. In some embodiments, the hybridization time can be longer than Is, 5 s, 10 s, 15 s, 30 s, 1 min, 1.5 min, 2 min, 2.5 min, 3 min, 4 min, or 5 min.

The annealing methods described herein can significantly shorten the annealing time. In some embodiments, at least 90% of the target nucleic acid anneals to the surface bound nucleic acid in less than or equal to about 15 s, 30 s, 1 min, 1.5 min, 2 min, 2.5 min, 3 min, 4 min, 5 min, 6 min, 7 min, 8 min, 9 min, 10 min, 15 min, 20 min, 25 min, 30 min, 40 min, 50 min, 60 min, 70 min, 80 min, 90 min, 100 min, 110 min, or 120 min. In some embodiments, at least 80% of the target nucleic acid anneals to the surface bound nucleic acid in less than or equal to about 15 s, 30 s, 1 min, 1.5 min, 2 min, 2.5 min, 3 min, 4 min, 5 min, 6 min, 7 min, 8 min, 9 min, 10 min, 15 min, 20 min, 25 min, 30 min, 40 min, 50 min, 60 min, 70 min, 80 min, 90 min, 100 min, 110 min, or 120 min. In some embodiments, at least 90% of the target nucleic acid anneals to the surface bound nucleic acid in greater than or equal to about 1 s, 5 s, 10 s, 15 s, 30 s, 1 min, 1.5 min, 2 min, 2.5 min, 3 min, 4 min, or 5 min. In some embodiments, at least 90% of the target nucleic acid anneals to the surface bound nucleic acid in the range of about 10 s to about 1 hour, about 30 s to about 50 min, about 1 min to about 50 min, or about 1 min to about 30 min. In some embodiments, at least 90% of the target nucleic acid anneals to the surface bound nucleic acid in between 2-25, 3-24, 4-23, 5-23, 6-22, 7-21, 8-20, 9-19, 10-18, 11-17, 12-16, or 13-15 min.

Improvements in hybridization efficiency: As used herein, hybridization efficiency (or yield) is a measure of the percentage of total available tethered adapter sequences on a solid surface, primer sequences, or oligonucleotide sequences in general that are hybridized to complementary sequences. In some instances, the use of optimized buffer formulations disclosed herein (optionally, used in combination with low non-specific binding surface) yield improved hybridization efficiency compared to that for a standard hybridization protocol. In some instances, the hybridization efficiency that may be achieved is better than 80%, 85%, 90%, 95%, 98%, or 99% in any of the hybridization reaction times specified above.

The method and composition described herein can be used in an isothermal annealing conditions. In some embodiments, the methods described herein can eliminate the cooling required for most hybridizations. In some embodiments, the annealing methods described herein can be performed at a temperature in the range of about 10° C. to 95° C., about 20° C. to 80° C., about 30° C. to 70° C. In some embodiments, the temperature can be lower than about 40° C., 50° C., 60° C., 70° C., 80° C., or 90° C.

Improvements in hybridization specificity: Methods, systems, compositions, and kits described herein provide for improved hybridization specificity, as compared to a comparable hybridization reaction performed with standard hybridization conditions and reagents. In some instances, the comparable hybridization reaction performed on a low-non-specific binding surface described herein at 90 degrees Celsius for 5 minutes followed by cooling for 120 minutes to reach a final temperature of 37 degrees Celsius in a buffer comprising saline-sodium citrate. In some instances, the hybridization specificity that may be achieved is better than 1 base mismatch in 10 hybridization events, 1 base mismatch in 100 hybridization events, 1 base mismatch in 1,000 hybridization events, or 1 base mismatch in 10,000 hybridization events. Hybridization specificity may be measured using techniques described in In some cases, at least or about 70%, 80%, or 90% of the sample nucleic acid molecules correctly hybridize to the capture nucleic acid molecules (e.g., adapter sequences, primer sequences, or oligonucleotide sequence) with a complementary sequence. In some cases, more than 90% of the sample nucleic acid molecules correctly hybridize to the capture nucleic acid molecules. In some cases, between 90%-99% of the sample nucleic acid molecules correctly hybridize to the capture nucleic acid molecules. In some cases, 100% of the sample nucleic acid molecules correctly hybridize to the capture nucleic acid molecules.

Hybridization specificity can be measured, by hybridizing labeled (e.g., Cy3) complementary oligos to surface bound nucleic acid molecules immobilized to the surface, dehybridizing and collecting the hybridized oligos, measuring a fluorescent signal from the collected oligos using a fluorescence plate reader at the appropriate excitation and emission wavelengths (e.g., 532, peak 570/30). The results are used to develop standard curves and accurate concentrations is measured. This assay can be repeated with oligos that show varying degrees of complementarity and the respective specificities.

Hybridization specificity as measured on the surface may be measured by dividing the nonspecific background counts (e.g., calculated using methods provided in example 3) by the nonspecific probe hybridization-nonspecific background counts (also may be calculated using methods in example 3). Calibration curves can be built and experiment with of oligos with varying degrees of complementarity can be added to calculate respective specificities more accurately.

The specificity of a given nucleic acid probe, p, can be quantified by the relative sensitivity when a p spot is exposed to a perfectly matched target, t, or to a mismatch, m, $$\frac{^L S_e}{^m S_e} = \frac{^m c_{50}^0}{^t c_{50}^0} = \frac{K_t}{K_m}.$$

The specificity of the assay can be quantified by considering the fraction of incorrectly hybridized probes, $P_m$.

$$P_m = \frac{y}{x+y} = \frac{c_m K_m}{c_m K_m + c_t K_t}.$$

In this case, $y = x(c_m/c_t)(K_m/K_t)$.

Improvements in hybridization sensitivity. hybridization sensitivity" refers to a concentration range of sample (or target) nucleic molecules in which hybridization occurs with a target hybridization specificity. In some cases, the target hybridization specificity is 90%, or more. In some cases, the methods, systems, compositions, and kits described herein utilize less than 10 nanomolar concentration of sample nucleic acid molecules to hybridize the sample nucleic acid molecules to capture nucleic acid molecules with high specificity. In some cases, between 10 nanomolar and 50 picomolar concentration of sample nucleic acid molecules is used. In some cases, between 9 nanomolar and 100 picomolar of sample nucleic acid molecules is used. In some cases, between 9 nanomolar and 150 picomolar of sample nucleic acid molecules is used. In some cases, between 7 nanomolar and 200 picomolar of sample nucleic acid molecules is used. In some cases, between 6 nanomolar and 250 picomolar of sample nucleic acid molecules is used. In some cases, between 5 nanomolar and 250 picomolar of sample nucleic acid molecules is used. In some cases, between 4 nanomolar and 300 picomolar of sample nucleic acid molecules is used. In some cases, between 3 nanomolar and 350 picomolar of sample nucleic acid molecules is used. In some cases, between 2 nanomolar and 400 picomolar of sample nucleic acid molecules is used. In some cases, between 1 nanomolar and 500 picomolar of sample nucleic acid molecules is used. In some cases, less than or equal to about 1 nanomolar of sample nucleic acid molecules is used. In some cases, less than or equal to about 250 picomolar of sample nucleic acid molecules is used. In some cases, less than or equal to about 200 picomolar of sample nucleic acid molecules is used. In some cases, less than or equal to about 150 picomolar of sample nucleic acid molecules is used. In some cases, less than or equal to about 100 picomolar of sample nucleic acid molecules is used. In some cases, less than or equal to about 50 picomolar of sample nucleic acid molecules is used.

In some cases, the hybridization sensitivity if calculated using the International Union of Pure and Applied Chemistry (IUPAC) consistent with the sensitivity, $S_e$, with the slope of the calibration curve. The calibration curve describes the measured response, R, to a target concentration, $c_t$, $R(c_t)$, and $S_c = dR/dc_t$.

The quantitative resolution of the assay, $\Delta c_t$, is then specified by $\Delta c_t = \in r(c_t)/S_c(c_t)$, where $\in_r$ is the measurement error as given by its standard deviation. The detection limit, the lowest detectable $c_t$, is determined by $\Delta c_t$ ($c_t=0$) since when the concentration $c_t$ is lower than $\Delta c_t$ ($c_t=0$), the error is larger than the signal; and assuming that R(ct) is proportional to the equilibrium hybridization fraction at the surface, x; i.e., R(ct)=κx+const where κ is a constant. This assumption is justified when the following conditions are fulfilled: (1), nonspecific adsorption is negligible and R is due only to hybridization at the surface; (2), the duration of the experiment is sufficiently long to allow the hybridization to reach equilibrium; and (3), the measured signal depends linearly on the amount of oligonucleotides at the surface.

Nucleic Acid Sequencing Applications

Nucleic acid sequencing is among the many applications for which the methods, compositions, systems, and kits described herein may be useful. Referring to FIG. 4, the methods disclosed herein, in some embodiments, comprise preparing a library of sample nucleic acid molecules for sequencing, hybridizing the library of sample nucleic acids to nucleic acid molecules coupled to a low non-specific binding surface in the presence of the hybridizing compositions described herein, amplifying the library of sample nucleic acids in situ, optionally linearizing the amplified sample nucleic acids in situ, de-hybridizing the linearized and amplified sample nucleic acids from the nucleic acid molecules coupled to the low non-specific binding surface, hybridizing a primer sequence to the sample nucleic acids, and sequencing the sample nucleic acids.

Figure 8:
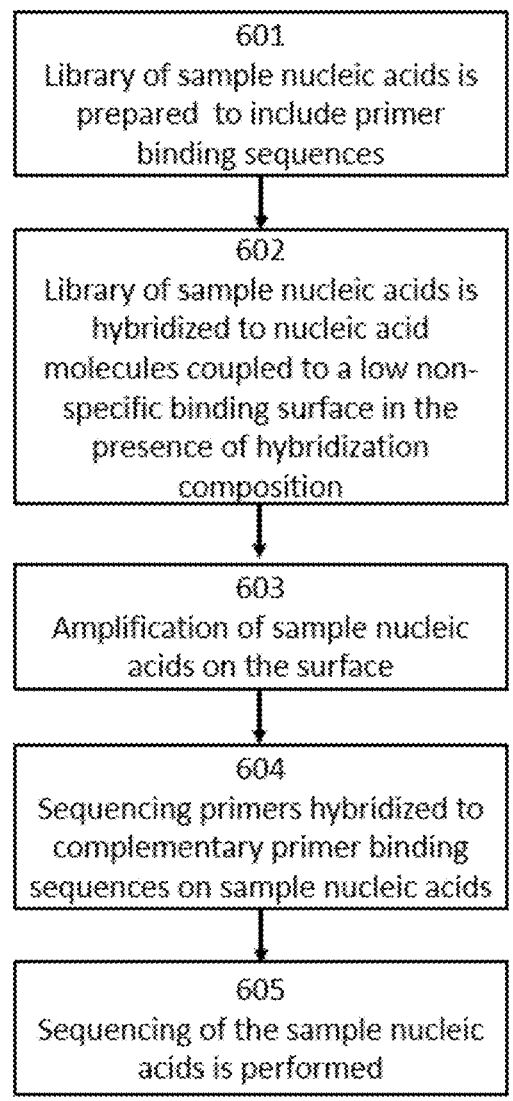
FIG. 8 shows a work flow according to various embodiments disclosed herein.

Referring to FIG. 8, a library of sample nucleic acid molecules is prepared 601, for example by a split ligation protocol, the library of sample nucleic acid molecules is hybridized to nucleic acid molecules coupled to a low non-specific binding surface in the presence of a hybridization composition described herein 602, hybridization of the sample nucleic acid molecules to the nucleic acid molecules coupled to the low non-specific binding surface occurs 603, sequencing primers are hybridized to complementary primer binding sequences on sample nucleic acids 604, and sequencing of the sample nucleic acids is performed 605.

Figure 9:
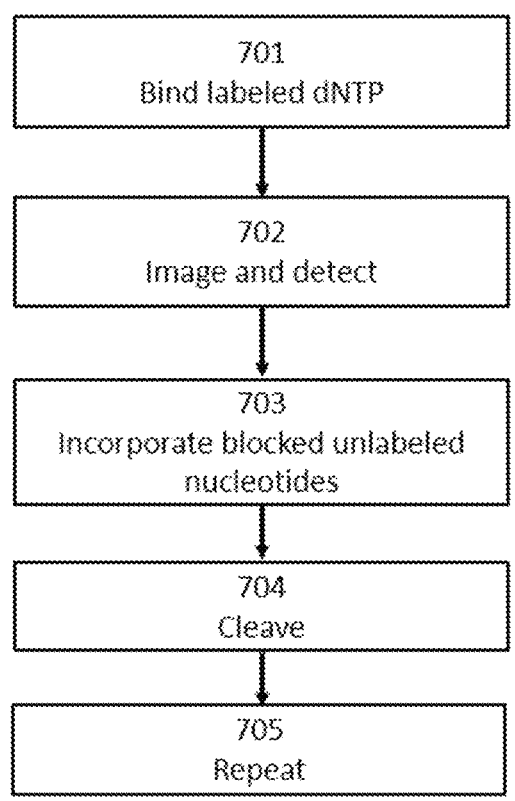
FIG. 9 shows a work flow for a sequence reaction according to various embodiments described herein.

FIG. 9 provides an exemplary sequencing workflow, wherein a labeled deoxyribonucleotide triphosphate (dNTP) binds to the sample nucleic acid molecule to determine the identity of the complementary nucleotide in the nucleic acid sequence of the sample nucleic acid molecule 701. In some cases, the dNTP is labeled with a fluorophore (e.g., Cy3), either directly or by interaction with a labeled detection reagent. The surface is optionally washed, to remove the unbound labeled dNTP. The surface is imaged to detect the presence of the labeled dNTP 702. The labeled dNTP is unbound from the sample nucleic acid molecule, and a blocked unlabeled dNTP is incorporated into the sample nucleic acid molecule 703. The blocked unlabeled nucleotide is cleaved 704. Steps 701-704 are repeated for the next nucleotide in the sample nucleic acid molecule 705.

The methods, compositions, systems, and kits described herein provide at least the following advantages, particular in a nucleic acid sequencing process: (i) decreased fluidic wash times (due to reduced non-specific binding, and thus faster sequencing cycle times), (ii) decreased imaging times (and thus faster turnaround times for assay readout and sequencing cycles), (iii) decreased overall work flow time requirements (due to decreased cycle times), (iv) decreased detection instrumentation costs (due to the improvements in contrast-to-noise ratio), (v) improved readout (base-calling) accuracy (due to improvements in contrast-to-noise ratio), (vi) improved reagent stability and decreased reagent usage requirements (and thus reduced reagents costs), and (vii) fewer run-time failures due to nucleic acid amplification failures.

Use of Multivalent Binding Composition in Combination with Low Non-Specific Binding Surface Disclosed herein are methods and systems for performing nucleic acid analysis with the multivalent binding compositions of the present disclosure on solid supports comprising low non-specific binding surface compositions that enable improved nucleic acid hybridization and amplification performance. In general, the disclosed supports may comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded target nucleic acid(s) to the support surface. In some instances, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

EXAMPLES

These examples are provided for illustrative purposes only and not to limit the scope of the claims provided herein.

Example 1—Preparation of Multivalent Binding Composition

One type of multi-armed substrate were made by reacting propargylamine dNTPs with Biotin-PEG-NHS. This aqueous reaction was driven to completion and purified; resulting in a pure Biotin-PEG-dNTP species. In separate reactions, several different PEG lengths were used, varying from 1K to 20K. The Biotin-PEG-dNTP species were mixed with either freshly prepared or commercially sourced dye-labeled streptavidin using a Dye:SA ratio of 3-5:1. Mixing of Biotin-PEG-dNTP with dye-labeled streptavidin was done in the presence of excess biotin-PEG-dNTP to ensure saturation of the biotin binding sites on each streptavidin tetramer. Complete complexes were purified away from excess biotin-PEG-dNTP by size exclusion chromatography. Each nucleotide type was conjugated and purified separately, then mixed together to create a 4 base mix for sequencing.

Another type of multi-armed substrate was made in a single pot by reacting multiarm PEG NHS with excess Dye-NH2 and propargylamine dNTPs. Various multiarm PEG NHS variants were used ranging from 4-16 arms and ranging in molecular weight from 5K to 40K. After reacting, excess small molecule dye and dNTP were removed by size exclusion chromatography. Each nucleotide type was conjugated and purified independently then mixed together to create a 4 base mix for sequencing.

Class II substrates were made using 1 pot reactions to simultaneously conjugate dye and dNTP. Alkyne-PEG-NHS was reacted with excess propargylamine dNTP. This product (Alkyne-PEG-dNTP) was then purified to homogeneity by chromatography. Multiple PEG lengths were used, varying between 1K and 20K. Dendrimer cores containing a variable, discrete number (12, 24, 48, 96) of azide conjugation sites. Conjugation of Alkyne-Dye and Alkyne-PEG-dNTP to the dendrimer core occurred in a one pot reaction containing excess dye and dNTP species via copper mediated click chemistry. After reacting, excess small molecule dye and dNTP were removed by size exclusion chromatography. Each nucleotide type was conjugated and purified independently then mixed together to create a 4 base mix for sequencing. We note that this scheme allows the ready substitution of alternative cores, such as dextrans, other polymers, proteins, etc.

Class III polymer-nucleotide conjugates were constructed by reacting 4- or 8-arm PEG NHS with a saturating mixture of biotin and propargylamine dNTP. This reaction was then purified by size exclusion chromatography. The result of this reaction was a multiarm PEG containing a discrete distribution of biotin and nucleotide. This heterogeneous population was then reacted with dye-labeled streptavidin and purified by size exclusion chromatography. Each nucleotide type was conjugated and purified independently then mixed together to create a 4 base mix for sequencing. We note that the distribution of biotin and nucleotide is tunable by the input ration of Biotin-NH2 to propargylamine dNTP.

Example 2—Detection of Ternary Complex

Binding reactions using the multivalent binding composition having PEG polymer-nucleotide conjugates were analyzed to detect possible formation of ternary binding complex. Multivalent PEG-substrate compositions were prepared using varying ratios of 4-armed PEG-amine (4ArmPEG-NH), biotin-PEG-amine (Biotin-PEG-NH), and nucleotide (Nuc) as follows: Samples PB1 and PB5, 4Arm-PEG-NH:Biotin-PEG-NH:Nuc=0.25:1:0.5; Sample PB2, 4ArmPEG-NH:Biotin-PEG-NH:Nuc=0.125:0.5:0.25; Sample PB3, 4ArmPEG-NH:Biotin-PEG-NH:Nuc=0.25:1: 0.5. Images were collected after washing with imaging buffer with the same composition as the exposure buffer, but containing no nucleotides or polymerase.

Contrast was scaled to maximize visualization of the dimmest signals, but no signals persisted following washing with imaging buffer (a. inset). Fluorescence images were obtained (not shown) of multivalent PEG-nucleotide (base-labeled) ligands at 500 nM after mixing in the exposure buffer and imaging in the imaging buffer as above. Additional fluorescence images were obtained (not shown) showing further base discrimination by exposure of multivalent ligands to inactive mutants of Klenow polymerase and the wild type Klenow (control) enzyme.

Using multivalent ligands formulations, the base discrimination can be enabled by providing polymerase-ligand interactions having increased avidity. In addition, it is shown that increased concentration of multivalent ligands can generate higher signals as well as various Klenow mutations that knock out catalytic activity can be used for avidity-based sequencing.

Example 3—Sequencing of Target Nucleic Acid Based on Ternary Complex

In order to demonstrate sequencing based on multivalent ligand reporters, 4 known templates were amplified using RCA methods on a low binding substrate. Successive cycles were exposed to exposure buffer containing 20 nM Klenow polymerase and 2.5 mM $Sr^{+2}$ and washed with imaging buffer and imaged. After imaging, the substrates were washed with wash buffer (EDTA and high salt) and blocked nucleotides were added to proceed to the next base. The cycle was repeated for 5 cycles. Spots were detected using standard imaging processing and spot detection and the sequences were called using a two color green and red scheme (G-Cy3 and A-Cy5) to identify the templates being cycled. As shown in FIG. 10A and FIG. 10B, multivalent ligands are able to provide base discrimination through all 5 sequencing cycles.

Example 4—Control of Nucleotide Dissociation from Ternary Complex

Figure 6:
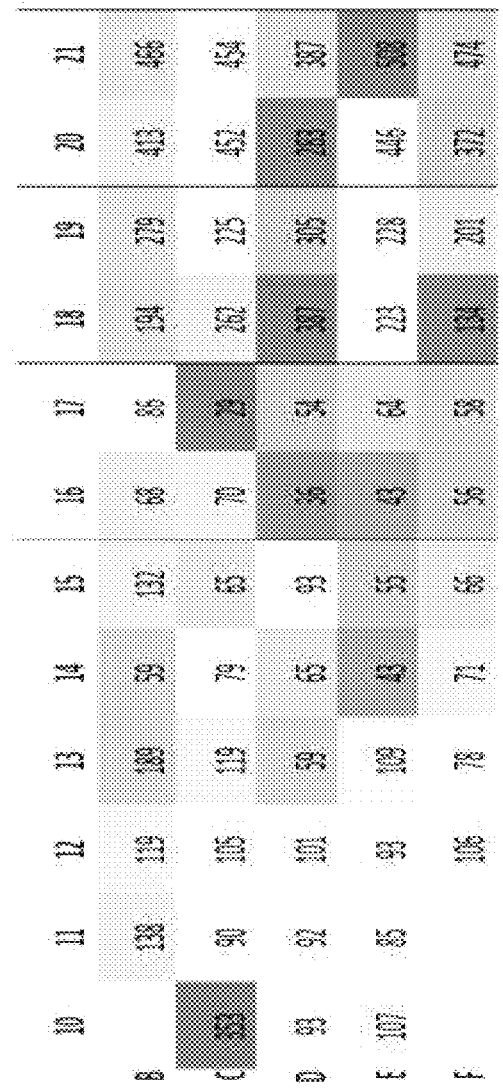
FIG. 6 shows a table with hybridization design of experiment spot counts.

Ternary complexes are prepared and imaged as in Example 2. The complexes are imaged over varying lengths of time to demonstrate the persistence of the ternary complex, e.g., as long as 60 seconds. After a length of time, the complexes are washed with a buffer identical to the buffer used for the formation of the complexes, only lacking any divalent cation, e.g., 10 mM Tris pH 8.0, 0.5 mM EDTA, 50 mM NaCl, 0.016% Triton™ X100 (without strontium acetate, or SrOAc), or, alternatively, the complexes are washed with a buffer identical to the buffer used for the formation of the complexes, which contains a chelating agent but otherwise lacks any divalent cation, e.g., 10 mM Tris pH 8.0, 0.5 mM EDTA, 50 mM NaCl, 0.016% Triton™ X100 (without strontium acetate, or SrOAc), with 100 nm-100 mM EDTA. The fluorescence from the complexes is observed over time allowing observation and quantitation of the dissociation of the ternary complexes. A representative timecourse of this dissolution is shown in FIG. 6.

Example 5—Extension of Target Nucleic Acid Complementary Sequence

After preparing, imaging, and dissociating ternary complexes as in Example 4, a deblocking solution is flowed into the chamber containing the bound DNA molecules, sufficient to remove the blocking moiety, such as an O-azidomethyl group, an O-alkyl hydroxylamino group, or an O-amino group, from the 3' end of the elongating DNA strand. Either following or concurrently with this, an extension solution is flowed into the chamber containing the bound DNA molecules. The extension solution contains a buffer, a divalent cation sufficient to support polymerase activity, an active polymerase, and an appropriate amount of all four nucleotides, where the nucleotides are blocked such that they are incapable of supporting further elongation after the addition of a single nucleotide to the elongating DNA strand, such as by incorporation of a 3'-O-azidomethyl group, a 3'-O-alkyl hydroxylamino group, or a 3'-O-amino group. The elongating strand is thus extended by one and only one base, and the binding of catalytically inactive polymerase and multivalent binding substrate can be used to call the next base in the cycle.

Alternatively, the nucleotides attached to the multivalent substrate may be attached through a labile bond, such that a buffer may be flowed into the chamber containing the bound DNA molecules containing a divalent cation or other cofactor sufficient to render the polymerase catalytically active. Prior to, after, or concurrently with this, conditions may be provided that are sufficient to cleave the base from the multivalent substrate such that it may be incorporated into the elongating strand. This cleavage and incorporation causes the dissociation of the label and the polymer backbone of the multivalent substrate while extending the elongating DNA strand by exactly one base. Washing to remove used polymer backbone is carried out, and new multivalent substrate is flowed into the chamber containing the bound DNA molecules, allowing the new base to be called as in Example 1.

Example 6—DNA Hybridization on Low Non-Specific Binding Surface

FIGS. 3A-3B provide examples of the optimized hybridization achieved on low binding surface using the disclosed hybridization method (FIG. 3A) with reduced concentrations of hybridization reporter probe and shortened hybridization times, as compared to the results achieved using a traditional hybridization protocol on the same low binding surface (FIG. 3B).

FIG. 3A shows hybridization reactions on the low binding surface according to the embodiments described herein. The rows provide two test hybridization conditions, hybridization condition 1 ("Hyb 1") and hybridization condition 2 ("Hyb 2"). Hyb 1 refers to the hybridization buffer composition C10 from Table 1. Hyb 2 refers to the hybridization buffer composition D18 from Table 1. A hybridization reporter probe (complementary oligonucleotide sequences labeled with a Cy™3 fluorophore at the 5' end) at concentrations reported in FIG. 3A (10 nM, 1 nM, 250 µM, 100 µM, and 50 µM) were hybridized in the buffer compositions at 60 degrees Celsius for 2 minutes.

FIG. 3B shows hybridization reactions on the low binding surface according to a standard hybridization protocol with standard hybridization conditions ("Standard Hyb Conditions"). A standard hybridization buffer of 2×-5× saline-sodium citrate (SSC) was used with same hybridization reporter probe above at the same concentrations above, as shown in FIG. 3A. The standard hybridization reaction was performed at 90 degrees Celsius with a slow cool process (2 hours) to reach 37 degrees Celsius.

For each hybridization reaction provided in FIG. 3A and FIG. 3B, the top row for each hybridization reaction is test ("T"), which is the complementary oligos (e.g., CY3™-5'-ACCCTGAAAGTACGTGCATTACATG-3' (SEQ ID NO: 1), and the bottom row for each hybridization reach is a control ("C"), which is a noncomplementary (e.g., CY3™-5'-ATGTCTATTACGTCACACTATTATG-3' (SEQ ID NO: 2)).

The surfaces used for all testing conditions were ultra-low non-specific binding surfaces having a level of non-specific Cy3 dye absorption corresponding to less than or equal to about 0.25 molecules/m$^2$. In this example, the low non-specific binding surfaces used were a glass substrates that were functionalized with Silane-PEG-5K-COOH (Nanocs Inc.).

Following completion of the hybridization reactions, wells were washed with 50 mM Tris pH 8.0; 50 mM NaCl.

Images were obtained acquired using an inverted microscope (Olympus IX83) equipped with 100×TIRF objective, NA=1.4 (Olympus), dichroic mirror optimized for 532 nm light (Semrock, Di03-R532-t1-25×36), a bandpass filter optimized for Cy3 emission, (Semrock, FF01-562/40-25), and a camera (sCMOS, Andor Zyla) under non-signal saturating conditions for 1 s, (Laser Quantum, Gem 532, <1 W/cm$^2$ at the sample) while sample is immersed a buffer (25 mM ACES, pH 7.4 buffer). Images were collected as described above and results shown in FIG. 3A (optimized) and FIG. 3B (standard).

A significant signal was observed from the reaction with 250 picomolar (pM) in both Hyb 1 and Hyb 2 hybridization reactions (FIG. 3A), as compared with the negative control. In contrast, no signal was observed from the reaction with 250 µM in the Standard Hyb conditions, as compared with the negative control. The same result was observed for lower input concentrations (e.g., 100 µM, 50 µM) of the hybridization reporter probe. FIG. 3A shows more than 200-fold decrease in input DNA (labeled oligo) required for specific DNA capture on low non-specific binding surfaces tested, a 50× decrease in hybridization times, and a reduction in the hybridization temperatures by half, as compared with standard hybridization methods and reagents on the same low non-specific binding substrates (FIG. 3B). The buffer compositions and methods described here boast improved hybridization specificity, decreased workflow times and increased hybridization sensitivity. The present inventions provide greatly improved methods and compositions for DNA sequencing and biosensor applications. It is to be understood that the above description is intended to be illustrative and not restrictive.

Example 7—Hybridization Compositions

Buffer compositions according to various embodiments described herein were optimized to facilitate hybridization of monotemplate oligonucleotide fragments to the low non-specific binding surface described herein.

Preparing the low non-specific binding surfaces. Glass substrates (175 um 22×60 mm², Corning Glass) were cleaned with KOH and ethanol. Low binding glass surfaces were prepared by incubating Silane-PEG5K-NHS (Nanocs) in ethanol at 65 degrees for 30 minutes. Oligonucleotides with 5' modified NH$_2$ were grafted to these surfaces in a mixture of 1 micromolar (uM), 5.1 uM, and 46 uM oligonucleotides in methanol/phosphate buffer for 20 minutes, to form immobilized oligonucleotides coupled to the glass substrates.

Circularizing monotemplate oligonucleotide fragments into library. Monotemplate oligonucleotide fragments (approximately 100 base pairs in length) were circularized using splint ligation protocol that contained complementary fragments to surface grafted primers.

Hybridizing the circularized library to immobilized oligonucleotides. Following circularization of library, circular library fragments were added at a concentration of 100 picomolar (pM) in various test hybridization test mixtures indicated by rows B-F. Individual buffer/library hybridization mixtures were added to 384 well plate with the functionalized surface affixed at 50 degrees Celsius for 4 minutes.

Figure 5:
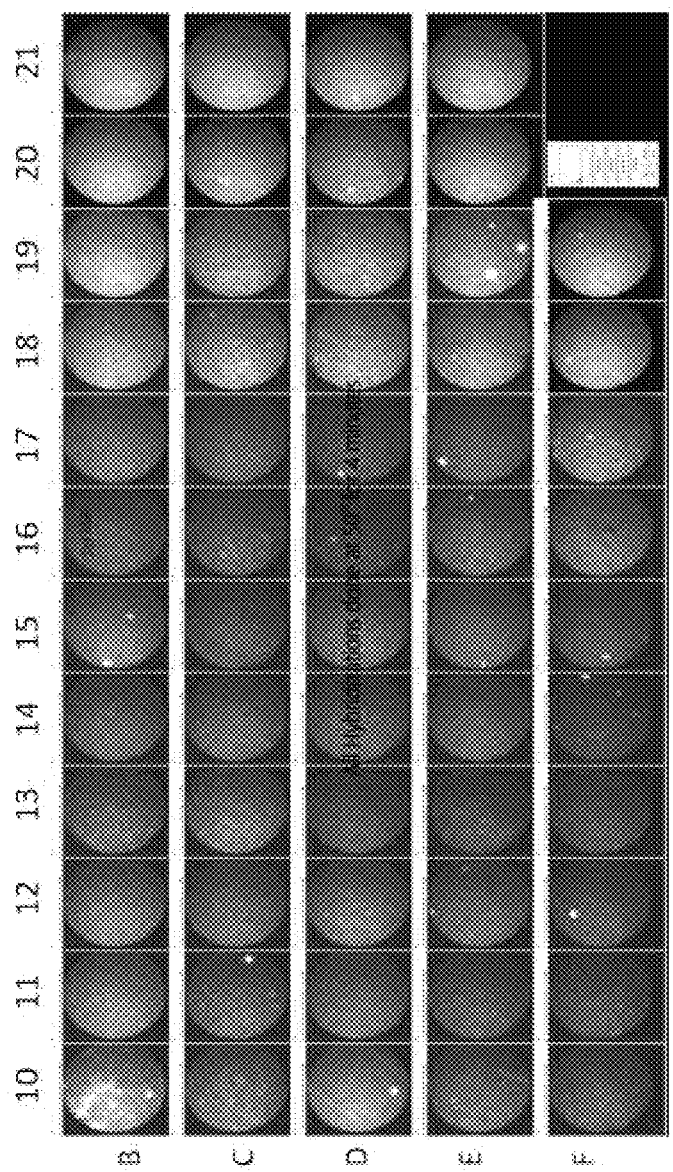
FIG. 5 shows the surface template hybridization images (NASA results at 100 pM) of the samples corresponding to the compositions used for hybridization.

Visualizing hybridization using test buffer compositions. Intercalating DNA stain was added to the buffer/library hybridization mixtures following the hybridization reaction to visualize the hybridization of the circularized libraries. The 384 well plate was imaged using a fluorescence microscope and 488 nanometer (nm) excitation with a 60× water immersion objective (1.2 NA, Olympus) (See FIG. 5). A number of buffer compositions were tested for the hybridization of target nucleic acid (e.g., circularized library) with surface bound nucleic acid (e.g., immobilized oligonucleotides). Table 1 provides the buffer compositions and immobilized oligonucleotide concentrations for each reaction seen in FIG. 5, with columns 10-21 in Table 1 corresponding with columns 10-21 of FIG. 5, and rows B-F corresponding to row B-F of FIG. 5. F10 and F11 are negative controls using standard hybridization conditions, where no background signal was detected signifying both the validity of the negative control and the low non-specific binding nature of surfaces tested.

TABLE 1

Buffer compositions tested for hybridizing target nucleic acid with surface bound nucleic acid

| Graft concentration | | 1 uM | | | | | | | | 5.1 uM | | 46 uM | |
| --- | --- | --- | --- | --- | --- | --- | --- | --- | --- | --- | --- | --- | --- |
| | 9 | 10 | 11 | 12 | 13 | 14 | 15 | 16 | 17 | 18 | 19 | 20 | 21 |
| B | Cracked | 75% ACN + MES | 75% ACN + Phos | 2 × SSC | 25% ACN + 2 × SSC + 10% PEG | Std buf. + 5% PEG + 30% Form. | 30% PEG | Std | 50% ACN + 50% Std buf. | Std | Std | Std | Std |
| C | 1 uM 31-NH2-Cy3 | 50% ACN + MES | 50% ACN + Tris | 4 × SSC | 25% ACN + MES + 20% PEG + 10% Form. | Std buf. + 10% PEG + 5% Form. | 20% PEG + 2 × SSC | Std + 2 | Std + 2 | Tris + 1 × SSC | Tris + 1 × SSC | Std buff + 5% PEG + 30% Form. | Std buff + 5% PEG + 30% Form. |
| D | 1 uM 31-NH2-Cy3 | 25% ACN + MES + 2 × SSC | 25% ACN + Tris + 2 × SSC | 10 × SSC | 50% EtOH + 2 × SSC | Std buf. + 10% PEG + 10% Form. | 10% PEG + 2 × SSC + 5% Form. | Std + 4 | Std + 4 | 25% ACN + MES + 20% PEG + 10% Form. | 25% ACN + MES + 20% PEG + 10% Form. | Std buff + 10% PEG + 5% Form. | Std buff + 10% PEG + 5% Form. |
| E | 1 uM 31-NH2-Cy3 | MES + 1 × SSC | Tris + 1 × SSC | 20 × SSC | 50% EtOH + 2 × SSC + 10% PEG | Std buf. + 20% PEG + 10% Form. | 5% Form. + 2 × SSC | Std + 6 | Std + 6 | Std buf. + 20% PEG + 10% Form. | Std buf. + 20% PEG + 10% Form. | 10% PEG + 2 × SSC + 5% Form. | 10% PEG + 2 × SSC + 5% Form. |
| F | 10 nM 31-NH2-Cy3 | 10 nM 31-NH2-Cy3 | 10 nM 31-NH2-Cy3 | 10 × SSC + 10% Form. | Std | Std buf. + 10% Form. | 10% Form. + 2 × SSC | Std + 8 | Std + 8 | Std buf. + 10% Form. | Std buf. + 10% Form. | 10% Form. + 2 × SSC | 10% Form. + 2 × SSC |

"Graft" concentration refers to the concentration of surface bound oligos. Spot counts for each of the hybridization conditions were tabulated, whereby higher counts indicated more effective hybridization buffer formulations as shown in FIG. 6. Table 1 provides the buffer compositions and immobilized oligonucleotide concentrations for each reaction seen in FIG. 6, with columns 10-21 in Table 1 corresponding with columns 10-21 of FIG. 6, and rows B-F corresponding to row B-F of FIG. 6.

Amplifying the hybridized target nucleic acid with surface bound nucleic acid. Following hybridization, the target nucleic acids were amplified to quantify hybridization effectiveness. Rolling circle amplification (RCA) was performed using amplification mixes with Bst according to manufacturer's instructions (New England Biolabs®). These the amplified colonies of target nucleic acids were further amplified using a RCA/PCR amplification strategy, whereby PCR cycles were performed on the RCA multimer nanoball to improve the detection sensitivity of the assay and more stringently quantify hybridized library.

Figure 7:
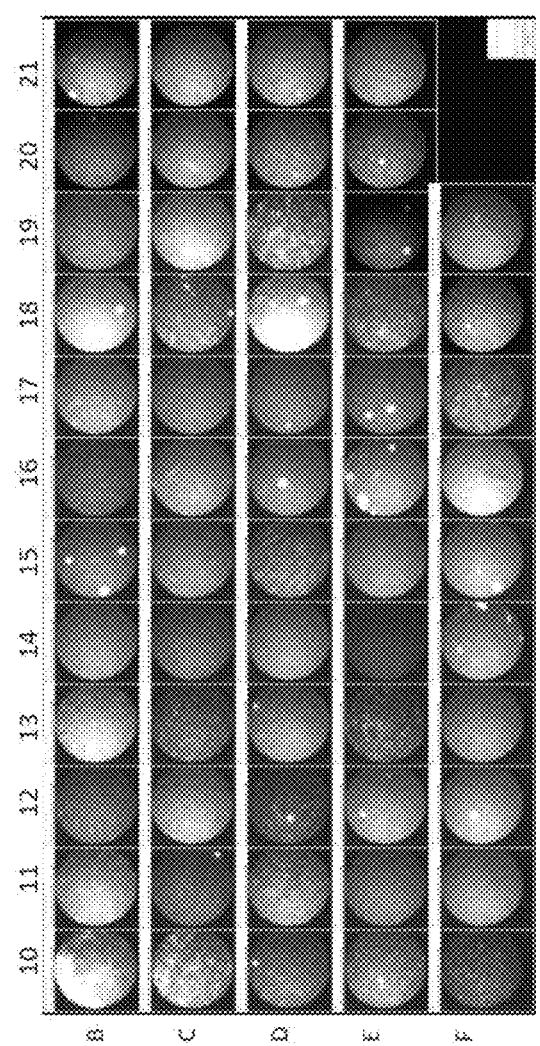
FIG. 7 shows the post nucleic acid surface amplification PCR images of the samples.

The resulting surface amplified products were again stained with intercalating DNA stains and imaged to verify hybridization specificity and effectiveness based on (See FIG. 7). Table 1 provides the buffer compositions and immobilized oligonucleotide concentrations for each reaction seen in FIG. 7, with columns 10-21 in Table 1 corresponding with columns 10-21 of FIG. 7, and rows B-F corresponding to row B-F of FIG. 7.

Analysis of Hybridization Buffers and conditions. Hybridization conditions were evaluated based on the correlation of maximum spot counts from FIG. 5, FIG. 6, and FIG. 7. Hybridization buffer C10, D18, and E21 showed the highest spot count, as compared to the negative controls provided in F10 and F11 in which water, instead of hybridization buffer, was used. in FIG. 6. This result was validated in FIG. 7 after amplification.

Example 8—Measuring Non-Specific Binding of Cyanine 3 Dye (Cy3)-Labeled Molecules In this example, the non-specific binding of cyanine 3 dye (Cy3)-labeled molecules was measured on the low non-specific binding surfaces disclosed herein. In independent non-specific binding assays, 1 uM labeled Cy3 dCTP (GE Amersham), 1 uM Cy5 dGTP dye (Jena Biosciences), 10 uM Aminoallyl-dUTP-ATTO-647N (Jena Biosciences), 10 uM Aminoallyl-dUTP-ATTO-Rho11 (Jena Biosciences), 10 uM Aminoallyl-dUTP-ATTO-Rho11 (Jena Biosciences), 10 uM cCTP-Cy3.5 (GE Amersham), and 10 uM 7-Propargylamino-7-deaza-dGTP-Cy3 (Jena Biosciences) were incubated individually on the low non-specific binding surfaces described in Example 7 (Glass substrates treated with Silane-PEG5K, Nanocs) at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged at single molecule resolution on an Olympus IX83 microscope (Olympus Corp., Center Valley, PA) with TIRF objective (100×, 1.4 NA, Olympus), a sCMOS camera (Zyla 4.2, Andor), an illumination source with excitation wavelengths of 532 nm or 635 nm. Dichroic mirrors were purchased from Semrock (IDEX Health & Science, LLC, Rochester, New York), e.g., 405, 488, 532, or 633 nm dichroic reflectors/beamsplitters, and band pass filters were chosen as 532 LP or 645 LP concordant with the appropriate excitation wavelength.

The imaging set-up enabled the visualization of single dye molecules bound to the substrates. Individual fluorescent spots were counted and the total spot numbers were divided by the respective area of the ROI. For example, with a 100× objective and Andor sCMOS camera, which has a pixel size of 6.5 microns, it is possible to calculate the area of a region of interest (ROI).

A low non-specific binding of the dye molecules above of less than or equal to about 0.50 molecules per $\mu m^2$ was observed. Some non-specific binding of the dye molecules of less than or equal to 0.25 molecules per $\mu m^2$ was observed.

Example 9—Nucleic Acid Sequence Reaction

A nucleic acid sequencing reaction is performed using the workflow provided in FIG. 4 using the disclosed hybridization compositions and methods from Example 6 and Example 7 on the surfaces used in Examples 6-9. In this non-limiting example, the processing times that are achieved are also provided in FIG. 4.

Many embodiments will be apparent to those of skill in the art upon reviewing the above description. By way of example, the invention has been described primarily with reference to the use of polymer-nucleotide conjugate, but it will be readily recognized by those of skill in the art that other types of particle-nucleotide conjugates could also be used. For example, in some embodiments it may be desirable to use particle-nucleotide conjugates which include quantum dot; a liposome; or an emulsion particle. Alternatively, the conjugation could be achieved by noncovalent bond such as hydrogen bond or other interactions. The scope of the invention should, therefore, be determined not with reference to the above description, but should instead be determined with reference to the appended claims, along with the full scope of equivalents to which such claims are entitled.

---

What is claimed:

1. A method for nucleic acid hybridization, the method comprising:
   (a) providing a surface comprising a hydrophilic polymer coating layer coupled thereto, wherein the hydrophilic polymer coating layer comprises a first nucleic acid molecule coupled thereto, and wherein the hydrophilic polymer coating layer has a water contact angle of less than 45 degrees; and
   (b) bringing the first nucleic acid molecule coupled to the hydrophilic polymer coating layer into contact with a hybridizing composition comprising (i) a second nucleic acid molecule at a concentration of one nanomolar or less and (ii) at least one organic solvent that is polar and aprotic, under conditions sufficient for the second nucleic acid molecule to hybridize to the first nucleic acid molecule coupled to the hydrophilic polymer coating layer in 30 minutes or less, wherein the method uses a reduced concentration of the second nucleic acid molecule and results in a shortened hybridization time as compared to a method that is not performed using the hybridizing composition and the surface.

2. The method of claim 1, wherein (b) is performed at a temperature that is from about 30 degrees Celsius to 70 degrees Celsius.

3. The method of claim 1, further comprising performing a nucleotide binding reaction on the surface between the first nucleic acid molecule and the second nucleic acid molecule.

4. The method of claim 3, wherein the pH buffer comprises 2-(N-morpholino)ethanesulfonic acid, acetonitrile, 3-(N-morpholino)propanesulfonic acid, methanol, or a combination thereof.

5. The method of claim 1, wherein the second nucleic acid molecule is present in the hybridizing composition at a concentration of 0.50 nanomolar or less.

6. The method of claim 1, wherein the second nucleic acid molecule is present in the hybridizing composition at a concentration of 250 picomolar or less.

7. The method of claim 1, wherein the second nucleic acid molecule is present in the hybridizing composition at a concentration of 100 picomolar or less.

8. The method of claim 1, wherein bringing the first nucleic acid molecule coupled to the hydrophilic polymer coating layer into contact with the hybridizing composition is performed for a time period of less than 30 minutes.

9. The method of claim 1, further comprising hybridizing the second nucleic acid molecule to the first nucleic molecule coupled to the hydrophilic polymer coating layer at a hybridization efficiency that is increased as compared to a comparable hybridization reaction performed for 120 minutes at 90 degrees Celsius for 5 minutes followed by cooling for 120 minutes to reach a final temperature of 37 degrees Celsius in a buffer comprising saline-sodium citrate.

10. The method of claim 1, further comprising hybridizing the second nucleic acid molecule to the first nucleic acid molecule with a hybridization stringency of at least 80%.

11. The method of claim 1, wherein the hydrophilic polymer coating layer exhibits a level of non-specific Cyanine 3 dye absorption of less than about 0.25 molecules per square micrometer.

12. The method of claim 1, wherein the hybridizing composition further comprises a pH buffer.

13. The method of claim 1, wherein the at least one organic solvent has a dielectric constant of no greater than about 115 as measured at 68 degrees Fahrenheit.

14. The method of claim 1, wherein the at least one organic solvent comprises at least one functional group selected from the group consisting of nitrile, lactone, sulfone, sulfite, and carbonate.

15. The method of claim 1, wherein the hybridizing composition further comprises formamide.

16. The method of claim 1, wherein the at least one organic solvent is miscible with water.

17. The method of claim 1, wherein a concentration of the at least one organic solvent in the hybridizing composition is at least about 5% by volume based on a total volume of the hybridizing composition.

18. The method of claim 1, wherein a concentration of the at least one organic solvent in the hybridizing composition is at least about 95% by volume based on a total volume of the hybridizing composition.

19. The method of claim 1, wherein the first nucleic acid molecule is coupled to the hydrophilic polymer coating layer through covalent bonding.

20. The method of claim 1, wherein the hybridizing composition further comprises a crowding agent.

21. The method of claim 20, wherein the crowding agent is selected from the group consisting of polyethylene glycol, dextran, hydroxypropyl methyl cellulose, hydroxyethyl methyl cellulose, hydroxybutyl methyl cellulose, hydroxypropyl cellulose, methyl cellulose, and hydroxyl methyl cellulose, and any combination thereof.

* * * * *

UNITED STATES PATENT AND TRADEMARK OFFICE
CERTIFICATE OF CORRECTION

| | | |
|---|---|---|
| PATENT NO. | : 12,313,627 B2 | Page 1 of 1 |
| APPLICATION NO. | : 18/431748 | |
| DATED | : May 27, 2025 | |
| INVENTOR(S) | : Arslan et al. | |

It is certified that error appears in the above-identified patent and that said Letters Patent is hereby corrected as shown below:

On the Title Page

Item (72), in Column 1, in "Inventors", Line 2, delete "Dieg," and insert -- Diego, --, therefor.

Signed and Sealed this
Thirteenth Day of January, 2026

John A. Squires
*Director of the United States Patent and Trademark Office*

SEQUENCE LISTING

```
Sequence total quantity: 2
SEQ ID NO: 1            moltype = DNA  length = 25
FEATURE                 Location/Qualifiers
source                  1..25
                        mol_type = other DNA
                        organism = synthetic construct
SEQUENCE: 1
accctgaaag tacgtgcatt acatg                                              25

SEQ ID NO: 2            moltype = DNA  length = 25
FEATURE                 Location/Qualifiers
source                  1..25
                        mol_type = other DNA
                        organism = synthetic construct
SEQUENCE: 2
atgtctatta cgtcacacta ttatg                                              25
```